(12) United States Patent
Jaitner et al.

(10) Patent No.: US 7,291,725 B2
(45) Date of Patent: Nov. 6, 2007

(54) SOS1 INHIBITORS

(75) Inventors: Birgit K. Jaitner, San Francisco, CA (US); Wendy J. Fantl, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 414 days.

(21) Appl. No.: 10/609,150

(22) Filed: Jun. 25, 2003

(65) Prior Publication Data

US 2005/0070490 A1 Mar. 31, 2005

Related U.S. Application Data

(60) Provisional application No. 60/391,993, filed on Jun. 26, 2002.

(51) Int. Cl.
*A61K 31/70* (2006.01)
*C07H 21/02* (2006.01)
*C07H 21/04* (2006.01)
*C12N 5/00* (2006.01)
*C12Q 1/68* (2006.01)

(52) U.S. Cl. .................. 536/24.5; 536/23.1; 536/24.1; 435/6; 514/44

(58) Field of Classification Search ...................... None
See application file for complete search history.

(56) References Cited

U.S. PATENT DOCUMENTS 5,656,595 A * 8/1997 Schweighoffer et al. ...... 514/12
6,455,307 B1 * 9/2002 McKay et al. .............. 435/375

FOREIGN PATENT DOCUMENTS

WO WO 93/21314 10/1993

OTHER PUBLICATIONS

Hart, T.C., *A Mutation in the SOS1 Gene Causes Hereditary Gingival Fibromatosis Type 1*, Am. J. Hum. Genet. 70:943-954, 2002.
Nyhus, J.K., *Direct in vivo Transfection of Antisense Fas-ligand Reduces Tumor Growth and Invasion*, Gene Therapy 8:209-214, 2001.
Qian, X. et al., *The Sos1 and Sos2 Ras-specific Exchange Factors: Differences in Placental Expression and Signaling Properties*, The EMBO Journal 19:642-654, 2000.
Sibilia, M. et al., *The EGF Receptor Provides an Essential Survival Signal for SOS-Dependent Skin Tumor Development*, CELL 102:211-220, 2000.
Branch, A.D., *A Good Antisense Molecule is Hard to Find*, TIBS 23:45-50, 1998.
Anazodo, M.I. et al., *Relative Levels of Inhibition of p24 Gene Expression by Different 20-mer antisense Oligonucleotide Sequences Targeting Nucleotides +1129 to +1268 of the HIV-1 gag Genome: an Analysis of Nechanism*, Biochem. Biophys. Res Commun. 229:305-309, 1996.
Hirota, Y. et al., *p53 Antisense Oligonucleotide Inhibits Growth of Human Colon Tumor and Normal Cell Lines*, Jpn. J. Cancer Res. 87:735-742, 1996.
Giles, R.V. et al., *Single Base Discrimination for Ribonuclease H-Dependent Antisense Effects Within Intact Human Leukemia Cells*, Nucleic Acids Research 23:954-961, 1995.
Gishizky, M.L., *Tyrosine Kinase Induced Mitogenesis. Breaking the Link with Cancer*, in Annual Reports in Medicinal Chemistry 30:247-253 (Academic Press, Inc., 1995).
Pandey, P. et al., *Association of the DF3/Muc1 Breast Cancer Antigen with Grb2 and the Sos/Ras Exchange Protein*, Can Res. 55:4000-4003, 1995.
Witty, J.P. et al., Modulation of Matrolysin Levels in Colon Carcinoma Cell Lines Affects Tumorigenicity in vivo, Can. Res. 54:4805-4812, 1994.
Haselhoff, J. et al., *Simple RNA enzymes with New and Highly Specific Endoribonuclease Activities*, NATURE 334:585-591, 1988.
Walbot, V. et al., *Plant Development and Ribozymes for Pathogens*, NATURE 334:196-197, 1988.
Forster, A.C. et al., *Self-Cleavage of Plus and Minus RNAs of a Virusoid and a Structural Model for the Active Sites*, CELL 49:211-220, 1987.
Uhlenbeck, O.C., *A Small Catalytic Oligoribonucleotide*, NATURE 328:596-600, 1987.
Weintraub et al., *Antisense RNA and DNA: Molecules That Bind With Specific Messenger RNA's Can Selectively Turn Off Genes. Eventually Certain Diseases May Be Treated Wtih Them; Today Antisense Molecules Are Valuable Research Tools*, Scientific American, 40-45, 1990.
Chin, Andrew, CD-ROM document, entitled "On the Preparation and Utilization of Isolated and Purified Oligonucleotides," including copy of letter, dated May 12, 2005 from Andrew Chin.

* cited by examiner

*Primary Examiner*—Sean McGarry
(74) *Attorney, Agent, or Firm*—Jane E. R. Potter; Susan L. Abrahamson; Alisa A. Harbin

(57) ABSTRACT

Inhibitors of human Sos1, including antisense oligonucleotides, methods, and compositions specific for human Sos1, are provided. Methods of using the compositions for modulating Sos1 expression and for regulating cell growth, particularly tumor cell growth, are also provided.

2 Claims, 11 Drawing Sheets

```
ATGCAGCAGGCGCCGCAGCCTTACGAGTTCTTCAGCGAGGAGAACAGTCCGAAATGGCGGGGACTGTTGG
TCTCGGCCCTGCGGAAGGTTCAGGTTCAAGTGCATCCCACTCTCTCAGCTAATGAAGAGTCTCTCTATTA
TATTGAAGAGCTGATTTTTCAGCTGCTTAATAAATTATGCATGGCCCAGCCAAGGACTGTTCAAGATGTA
GAGGAGCGAGTTCAGAAGACCTTTCCTCACCCAATTGATAAATGGGCCATTGCTGATGCACAATCTGCTA
TAGAAAAAACGAAAACGAAGAAATCCTCTTTTACTGCCTGTGGACAAAATCCATCCTTCGTTGAAGGAAGT
ATTAGGGTACAAAGTGGACTACCATGTATCCCTATATATTGTGGCTGTACTAGAGTATATCTCAGCTGAT
ATTTTAAAATTGGCTGGTAATTATGTTTTTAATATCCGGCATTATGAAATATCTCAGCAGGACATTAAAG
TGTCAATGTGTGCGGATAAGGTTTTGATGGACATGTTTGATCAGGATGACATAGGTTTGGTTTCTCTCTG
TGAAGATGAACCCTGTTCTTCTGGTGAATTAAACTACTATGATCTTGTCAGAACTGAAATCGCAGAAGAA
AGACAGTATCTACGGGAATTAAATATGATCATAAAAGTGTTTCGAGAAGCCTTTCTTTCTGATAGAAAGC
TGTTTAAACCTTCTGTATACGAAAAGATTTTTAGTAACATTTCAGATATACATGAATTGACTGTGAAACT
TTTAGGTTTGATTGAAGACACAGTTGAAATGACTGATGAAAGCAGTCCTCATCCCTTAGCTGGCAGCTGT
TTTGAAGATTTGGCAGAAGAGCAAGCATTTGATCCTTATGAAACATTATCACAGGACATTCTTTCACCAG
AGTTTCATGAACATTTCAATAAATTGATGGCCAGACCTGCAGTTGCTCTACACTTTCAGTCCATTGCTGA
TGGTTTTAAAGAGGCAGTTCGTTATGTCCTTCCACGTCTTATGCTGGTGCCAGTGTATCACTGTTGGCAC
TACTTTGAGTTACTAAAGCAATTGAAAGCATGTAGTGAAGAACAAGAAGACAGAGAATGTTTGAACCAAG
CTATTACTGCTCTCATGAATCACCAAGGTAGCATGGACCGAATTTACAAGCAGTATTCACCTAGACGTCG
ACCTGGAGATCCTGTTTGCCCTTTTTATAGTCACCAATTAAGAAGCAAACACCTGGCTATCAAAAAAATG
AATGAAATTCAGAAAAATATCGATGGATGGGAAGGCAAAGATATTGGACAGTGTTGTAATGAATTCATTA
TGGAGGGACCATTGACAAGAATCGGTGCCAAACATGAACGGCATATTTTTCTGTTTGATGGCTTAATGAT
CAGTTGTAAACCTAATCATGGCCAGACTCGGCTTCCAGGTTACACTAGTGCAGAATACAGGTTAAAAGAA
AAATTTGTCATGAGGAAAATACAAATTTGTGATAAAGAAGATACTTGTGAGCACAAGCATGCATTTGAAT
TAGTATCCAAAGATGAGAACAGCATAATATTTGCTGCTAAGTCTGCTGAAGAAAAAAACAACTGGATGGC
AGCCCTTATTTCTCTTCATTATCGTAGTACTCTAGATCGAATGTTAGATTCAGTATTATTGAAAGAAGAA
AATGAGCAACCACTGAGATTACCAAGTCCTGAAGTATATCGTTTTGTAGTAAAAGACTCTGAGGAAAACA
TTGTTTTTGAAGACAACTTGCAAAGTAGAAGTGGCATCCCCATTATTAAAGGAGGAACTGTAGTGAAATT
AATTGAAAGGTTAACATATCATATGTATGCAGATCCCAATTTTGTTCGTACTTTTCTTACCACATATCGT
TCATTTTGTAAACCACAGGAATTGCTGAGCTTACTGATTGAACGGTTTGAAATTCCAGAGCCAGAACCTA
CTGACGCAGACAAATTGGCAATAGAGAAAGGCGAGCAGCCAATCAGTGCAGACCTTAAAAGATTTCGCAA
GGAATATGTCCAACCAGTACAACTTAGGGTACTTAATGTATTCCGCCATTGGGTTGACCATCATTATTAT
GACTTTGAAAGAGACCTGGAATTGCTGGAAAGACTAGAATCCTTCATTTCAAGTGTAAGAGGGAAAGCTA
TGAAAAAATGGGTAGAGTCAATTGCTAAGATCATCAGGAGGAAGAAGCAAGCTCAGGCAAATGGAGTAAG
CCATAATATTACCTTTGAAAGTCCACCTCCACCAATTGAATGGCATATCAGCAAACCAGGACAGTTTGAA
ACATTTGATCTCATGACACTTGATCCAATAGAAATTGCACGTCAGCTGACACTTTTGGAGTCTGATCTTT
ACAGGAAAGTTCAACCGTCTGAACTTGTAGGGAGTGTGTGGACCAAAGAAGATAAAGAAATAAATTCTCC
AAATTTATTAAAAATGATTCGCCATACCACAAATCTCACCCTCTGGTTTGAAAAATGCATTGTGGAAGCA
GAAAATTTTGAAGAACGGGTGGCAGTACTAAGTAGAATTATAGAAATTCTGCAAGTTTTTCAAGATTTGA
ATAATTTCAATGGCGTATTGGAGATAGTCAGTGCAGTAAATTCAGTGTCAGTATACAGACTAGACCATAC
CTTTGAGGCACTGCAGGAAAGGAAAAGGAAAATTTTGGACGAAGCTGTGGAATTAAGTCAAGATCACTTT
```

*Fig. 1A*

```
AAAAAATACCTAGTAAAACTTAAGTCAATCAATCCACCTTGTGTGCCTTTTTTTGGAATATATTTAACAA
ATATTCTGAAGACCGAAGAAGGGAATAATGATTTTTTAAAAAGAAAGGGAAAAGATTTAATCAATTTCAG
TAAGAGGAGGAAAGTAGCTGAAATTACTGGAGAAATTCAGCAGTATCAGAATCAGCCTTACTGTTTACGG
ATAGAACCAGATATGAGGAGATTCTTTGAAAACCTTAACCCCATGGGAAGTGCATCTGAAAAAGAGTTTA
CAGATTATTTGTTCAACAAGTCACTAGAAATTGAACCTCGAAACTGCAAACAGCCACCTCGATTTCCTAG
GAAATCAACTTTTTCCTTAAAATCTCCTGGAATAAGGCCTAACACAGGCCGACATGGCTCTACCTCAGGT
ACTTTACGAGGTCACCCAACACCATTAGAAAGAGAACCATGTAAAATAAGCTTTAGTCGGATTGCTGAAA
CTGAGCTGGAATCAACAGTGTCAGCACCAACCTCTCCAAATACACCATCTACTCCACCAGTATCTGCTTC
TTCAGACCTTAGTGTATTTTTAGATGTGGATCTCAACAGCTCCTGTGGCAGCAATAGCATCTTTGCTCCA
GTGCTTTTGCCACATTCAAAGTCTTTCTTTAGTTCATGTGGTAGTTTACATAAACTAAGTGAAGAGCCCC
TGATTCCTCCTCCTCTTCCTCCTCGAAAAAAGTTTGATCATGATGCTTCAAATTCCAAGGGAAATATGAA
ATCTGATGATGATCCTCCTGCTATTCCACCGAGACAGCCTCCTCCTCCAAAGGTAAAACCCAGAGTTCCT
GTTCCTACTGGTGCATTTGATGGGCCTCTGCATAGTCCACCTCCGCCACCACCAAGAGATCCTCTTCCTG
ATACCCCTCCACCAGTTCCCCTTCGGCCTCCAGAACACTTTATAAACTGTCCATTTAATCTTCAGCCACC
TCCACTGGGGCATCTTCACAGAGATTCAGACTGGCTCAGAGACATTAGTACGTGTCCAAATTCGCCAAGC
ACTCCTCCTAGCACACCCTCTCCAAGGGTACCGCGTCGATGCTATGTGCTCAGTTCTAGTCAGAATAATC
TTGCTCATCCTCCAGCTCCCCCTGTTCCACCAAGGCAGAATTCAAGCCCTCATCTGCCAAAACTGCCACC
AAAGACTTACAAACGGGAGCTTTCGCACCCCCCATTGTACAGACTGCCTTTGCTAGAAAATGCAGAAACT
CCCCAATGA
```

*Fig. 1B*

```
Met Gln Gln Ala Pro Gln Pro Tyr Glu Phe Phe Ser Glu Glu Asn Ser
 1            5                  10                   15
Pro Lys Trp Arg Gly Leu Leu Val Ser Ala Leu Arg Lys Val Gln Val
            20                  25                  30
Gln Val His Pro Thr Leu Ser Ala Asn Glu Glu Ser Leu Tyr Tyr Ile
            35                  40                  45
Glu Glu Leu Ile Phe Gln Leu Asn Lys Leu Cys Met Ala Gln Pro
        50                  55              60
Arg Thr Val Gln Asp Val Glu Glu Arg Val Gln Lys Thr Phe Pro His
 65                  70                  75                  80
Pro Ile Asp Lys Trp Ala Ile Ala Asp Ala Gln Ser Ala Ile Glu Lys
                85                  90                  95
Arg Lys Arg Arg Asn Pro Leu Leu Leu Pro Val Asp Lys Ile His Pro
            100                 105                 110
Ser Leu Lys Glu Val Leu Gly Tyr Lys Val Asp Tyr His Val Ser Leu
            115                 120                 125
Tyr Ile Val Ala Val Leu Glu Tyr Ile Ser Ala Asp Ile Leu Lys Leu
 130                 135                 140
Ala Gly Asn Tyr Val Phe Asn Ile Arg His Tyr Glu Ile Ser Gln Gln
145                  150                 155                 160
Asp Ile Lys Val Ser Met Cys Ala Asp Lys Val Leu Met Asp Met Phe
                165                 170                 175
Asp Gln Asp Asp Ile Gly Leu Val Ser Leu Cys Glu Asp Glu Pro Cys
            180                 185                 190
Ser Ser Gly Glu Leu Asn Tyr Tyr Asp Leu Val Arg Thr Glu Ile Ala
            195                 200                 205
Glu Glu Arg Gln Tyr Leu Arg Glu Leu Asn Met Ile Ile Lys Val Phe
    210                 215                 220
Arg Glu Ala Phe Leu Ser Asp Arg Lys Leu Phe Lys Pro Ser Val Tyr
225                 230                 235                 240
Glu Lys Ile Phe Ser Asn Ile Ser Asp Ile His Glu Leu Thr Val Lys
                245                 250                 255
Leu Leu Gly Leu Ile Glu Asp Thr Val Glu Met Thr Asp Glu Ser Ser
            260                 265                 270
Pro His Pro Leu Ala Gly Ser Cys Phe Glu Asp Leu Ala Glu Glu Gln
        275                 280                 285
Ala Phe Asp Pro Tyr Glu Thr Leu Ser Gln Asp Ile Leu Ser Pro Glu
290                 295                 300
```

*Fig. 2A*

```
Phe His Glu His Phe Asn Lys Leu Met Ala Arg Pro Ala Val Ala Leu
305                 310                 315                 320
His Phe Gln Ser Ile Ala Asp Gly Phe Lys Glu Ala Val Arg Tyr Val
            325                 330                 335
Leu Pro Arg Leu Met Leu Val Pro Val Tyr His Cys Trp His Tyr Phe
            340                 345                 350
Glu Leu Leu Lys Gln Leu Lys Ala Cys Ser Glu Gln Glu Asp Arg
            355             360                 365
Glu Cys Leu Asn Gln Ala Ile Thr Ala Leu Met Asn His Gln Gly Ser
    370                 375                 380
Met Asp Arg Ile Tyr Lys Gln Tyr Ser Pro Arg Arg Arg Pro Gly Asp
385                 390                 395                 400
Pro Val Cys Pro Phe Tyr Ser His Gln Leu Arg Ser Lys His Leu Ala
                405                 410                 415
Ile Lys Lys Met Asn Glu Ile Gln Lys Asn Ile Asp Gly Trp Glu Gly
                420                 425                 430
Lys Asp Ile Gly Gln Cys Cys Asn Glu Phe Ile Met Glu Gly Pro Leu
            435                 440                 445
Thr Arg Ile Gly Ala Lys His Glu Arg His Ile Phe Leu Phe Asp Gly
        450                 455                 460
Leu Met Ile Ser Cys Lys Pro Asn His Gly Gln Thr Arg Leu Pro Gly
465                 470                 475                 480
Tyr Thr Ser Ala Glu Tyr Arg Leu Lys Glu Lys Phe Val Met Arg Lys
                485                 490                 495
Ile Gln Ile Cys Asp Lys Glu Asp Thr Cys Glu His Lys His Ala Phe
            500                 505                 510
Glu Leu Val Ser Lys Asp Glu Asn Ser Ile Ile Phe Ala Ala Lys Ser
        515                 520                 525
Ala Glu Glu Lys Asn Asn Trp Met Ala Ala Leu Ile Ser Leu His Tyr
    530                 535                 540
Arg Ser Thr Leu Asp Arg Met Leu Asp Ser Val Leu Leu Lys Glu Glu
545                 550                 555                 560
Asn Glu Gln Pro Leu Arg Leu Pro Ser Pro Glu Val Tyr Arg Phe Val
                565                 570                 575
Val Lys Asp Ser Glu Glu Asn Ile Val Phe Glu Asp Asn Leu Gln Ser
            580                 585                 590
Arg Ser Gly Ile Pro Ile Ile Lys Gly Gly Thr Val Val Lys Leu Ile
        595                 600                 605
Glu Arg Leu Thr Tyr His Met Tyr Ala Asp Pro Asn Phe Val Arg Thr
610                 615                 620
```

Fig. 2B

```
Phe Leu Thr Thr Tyr Arg Ser Phe Cys Lys Pro Gln Glu Leu Leu Ser
625                 630             635                 640
Leu Leu Ile Glu Arg Phe Glu Ile Pro Glu Pro Glu Pro Thr Asp Ala
            645                 650                 655
Asp Lys Leu Ala Ile Glu Lys Gly Glu Gln Pro Ile Ser Ala Asp Leu
            660                 665                 670
Lys Arg Phe Arg Lys Glu Tyr Val Gln Pro Val Gln Leu Arg Val Leu
        675                 680                 685
Asn Val Phe Arg His Trp Val Asp His His Tyr Tyr Asp Phe Glu Arg
    690                 695                 700
Asp Leu Glu Leu Leu Glu Arg Leu Glu Ser Phe Ile Ser Ser Val Arg
705                 710                 715                 720
Gly Lys Ala Met Lys Lys Trp Val Glu Ser Ile Ala Lys Ile Ile Arg
                725                 730                 735
Arg Lys Lys Gln Ala Gln Ala Asn Gly Val Ser His Asn Ile Thr Phe
            740                 745                 750
Glu Ser Pro Pro Pro Pro Ile Glu Trp His Ile Ser Lys Pro Gly Gln
            755                 760                 765
Phe Glu Thr Phe Asp Leu Met Thr Leu Asp Pro Ile Glu Ile Ala Arg
        770                 775                 780
Gln Leu Thr Leu Leu Glu Ser Asp Leu Tyr Arg Lys Val Gln Pro Ser
785                 790                 795                 800
Glu Leu Val Gly Ser Val Trp Thr Lys Glu Asp Lys Glu Ile Asn Ser
            805                 810                 815
Pro Asn Leu Leu Lys Met Ile Arg His Thr Thr Asn Leu Thr Leu Trp
            820                 825                 830
Phe Glu Lys Cys Ile Val Glu Ala Glu Asn Phe Glu Glu Arg Val Ala
        835                 840                 845
Val Leu Ser Arg Ile Ile Glu Ile Leu Gln Val Phe Gln Asp Leu Asn
850                 855                 860
Asn Phe Asn Gly Val Leu Glu Ile Val Ser Ala Val Asn Ser Val Ser
865                 870                 875                 880
Val Tyr Arg Leu Asp His Thr Phe Glu Ala Leu Gln Glu Arg Lys Arg
            885                 890                 895
Lys Ile Leu Asp Glu Ala Val Glu Leu Ser Gln Asp His Phe Lys Lys
            900                 905                 910
Tyr Leu Val Lys Leu Lys Ser Ile Asn Pro Pro Cys Val Pro Phe Phe
        915                 920                 925
Gly Ile Tyr Leu Thr Asn Ile Leu Lys Thr Glu Glu Gly Asn Asn Asp
930                 935                 940
```

*Fig. 2C*

```
APhe Leu Lys Arg Lys Gly Lys Asp Leu Ile Asn Phe Ser Lys Arg Arg
945                 950                 955                 960
Lys Val Ala Glu Ile Thr Gly Glu Ile Gln Gln Tyr Gln Asn Gln Pro
                965                 970                 975
Tyr Cys Leu Arg Ile Glu Pro Asp Met Arg Arg Phe Phe Glu Asn Leu
            980                 985                 990
Asn Pro Met Gly Ser Ala Ser Glu Lys Glu Phe Thr Asp Tyr Leu Phe
            995                 1000                1005
Asn Lys Ser Leu Glu Ile Glu Pro Arg Asn Cys Lys Gln Pro Pro Arg
            1010                1015                1020
Phe Pro Arg Lys Ser Thr Phe Ser Leu Lys Ser Pro Gly Ile Arg Pro
1025                1030                1035                1040
Asn Thr Gly Arg His Gly Ser Thr Ser Gly Thr Leu Arg Gly His Pro
                1045                1050                1055
Thr Pro Leu Glu Arg Glu Pro Cys Lys Ile Ser Phe Ser Arg Ile Ala
            1060                1065                1070
Glu Thr Glu Leu Glu Ser Thr Val Ser Ala Pro Thr Ser Pro Asn Thr
        1075                1080                1085
Pro Ser Thr Pro Pro Val Ser Ala Ser Ser Asp Leu Ser Val Phe Leu
        1090                1095                1100
Asp Val Asp Leu Asn Ser Ser Cys Gly Ser Asn Ser Ile Phe Ala Pro
1105                1110                1115                1120
Val Leu Leu Pro His Ser Lys Ser Phe Phe Ser Ser Cys Gly Ser Leu
                1125                1130                1135
His Lys Leu Ser Glu Glu Pro Leu Ile Pro Pro Pro Leu Pro Pro Arg
            1140                1145                1150
Lys Lys Phe Asp His Asp Ala Ser Asn Ser Lys Gly Asn Met Lys Ser
            1155                1160                1165
Asp Asp Asp Pro Pro Ala Ile Pro Pro Arg Gln Pro Pro Pro Pro Lys
            1170                1175                1180
Val Lys Pro Arg Val Pro Val Pro Thr Gly Ala Phe Asp Gly Pro Leu
1185                1190                1195                1200
His Ser Pro Pro Pro Pro Pro Pro Arg Asp Pro Leu Pro Asp Thr Pro
                1205                1210                1215
Pro Pro Val Pro Leu Arg Pro Pro Glu His Phe Ile Asn Cys Pro Phe
            1220                1225                1230
Asn Leu Gln Pro Pro Pro Leu Gly His Leu His Arg Asp Ser Asp Trp
            1235                1240                1245
Leu Arg Asp Ile Ser Thr Cys Pro Asn Ser Pro Ser Thr Pro Pro Ser
            1250                1255                1260
```

*Fig. 2D*

```
Thr Pro Ser Pro Arg Val Pro Arg Arg Cys Tyr Val Leu Ser Ser Ser
1265            1270            1275            1280
Gln Asn Asn Leu Ala His Pro Pro Ala Pro Pro Val Pro Pro Arg Gln
            1285            1290            1295
Asn Ser Ser Pro His Leu Pro Lys Leu Pro Pro Lys Thr Tyr Lys Arg
            1300            1305            1310
Glu Leu Ser His Pro Pro Leu Tyr Arg Leu Pro Leu Leu Glu Asn Ala
        1315            1320            1325
Glu Thr Pro Gln
    1330
```

*Fig. 2E*

SEQUENCE LISTING

```
<160> NUMBER OF SEQ ID NOS: 14

<210> SEQ ID NO 1
<211> LENGTH: 3999
<212> TYPE: DNA
<213> ORGANISM: Homo sapiens

<400> SEQUENCE: 1
atgcagcagg cgccgcagcc ttacgagttc ttcagcgagg agaacagtcc gaaatggcgg      60
ggactgttgg tctcggccct gcggaaggtt caggttcaag tgcatcccac tctctcagct     120
aatgaagagt ctctctatta tattgaagag ctgattttc agctgcttaa taaattatgc     180
```

-continued

```
atggcccagc caaggactgt tcaagatgta gaggagcgag ttcagaagac ctttcctcac    240
ccaattgata aatgggccat tgctgatgca caatctgcta tagaaaaacg aaaacgaaga    300
aatcctcttt tactgcctgt ggacaaaatc catccttcgt tgaaggaagt attagggtac    360
aaagtggact accatgtatc cctatatatt gtggctgtac tagagtatat ctcagctgat    420 atttaaaat tggctggtaa ttatgttttt aatatccggc attatgaaat atctcagcag    480
gacattaaag tgtcaatgtg tgcggataag gttttgatgg acatgtttga tcaggatgac    540
ataggtttgg tttctctctg tgaagatgaa ccctgttctt ctggtgaatt aaactactat    600
gatcttgtca gaactgaaat cgcagaagaa agacagtatc tacgggaatt aaatatgatc    660
ataaaagtgt ttcgagaagc cttctttct gatagaaagc tgtttaaacc ttctgtatac    720
gaaaagattt ttagtaacat ttcagatata catgaattga ctgtgaaact tttaggtttg    780
attgaagaca cagttgaaat gactgatgaa agcagtcctc atcccttagc tggcagctgt    840
tttgaagatt tggcagaaga gcaagcattt gatccttatg aaacattatc acaggacatt    900
cttccaccag agtttcatga acatttcaat aaattgatgg ccagacctgc agttgctcta    960
cactttcagt ccattgctga tggttttaaa gaggcagttc gttatgtcct tccacgtctt    1020
atgctggtgc cagtgtatca ctgttggcac tactttgagt tactaaagca attgaaagca    1080
tgtagtgaag aacaagaaga cagagaatgt ttgaaccaag ctattactgc tctcatgaat    1140
caccaaggta gcatggaccg aatttacaag cagtattcac ctagacgtcg acctggagat    1200
cctgtttgcc ctttttatag tcaccaatta agaagcaaac acctggctat caaaaaaatg    1260
aatgaaattc agaaaaatat cgatggatgg gaaggcaaag atattggaca gtgttgtaat    1320
gaattcatta tggagggacc attgacaaga atcggtgcca acatgaacg gcatattttt    1380 ctgtttgatg gcttaatgat cagttgtaaa cctaatcatg gccagactcg gcttccaggt    1440
tacactagtg cagaatacag gttaaaagaa aaatttgtca tgaggaaaat acaaatttgt    1500
gataaagaag atacttgtga gcacaagcat gcatttgaat tagtatccaa agatgagaac    1560
agcataatat ttgctgctaa gtctgctgaa gaaaaaaaca actggatggc agcccttatt    1620
tctcttcatt atcgtagtac tctagatcga atgttagatt cagtattatt gaagaagaa     1680 aatgagcaac cactgagatt accaagtcct gaagtatatc gttttgtagt aaaagactct    1740
gaggaaaaca ttgttttga agacaacttg caaagtagaa gtggcatccc cattattaaa    1800
ggaggaactg tagtgaaatt aattgaaagg ttaacatatc atatgtatgc agatcccaat    1860
tttgttcgta cttttcttac cacatatcgt tcatttgta aaccacagga attgctgagc    1920
ttactgattg aacggtttga aattccagag ccagaaccta ctgacgcaga caaattggca    1980
atagagaaag gcgagcagcc aatcagtgca gaccttaaaa gatttcgcaa ggaatatgtc    2040
caaccagtac aacttagggt acttaatgta ttccgccatt gggttgacca tcattattat    2100
gactttgaaa gagacctgga attgctggaa agactagaat ccttcatttc aagtgtaaga    2160
gggaaagcta tgaaaaaatg ggtagagtca attgctaaga tcatcaggag gaagaagcaa    2220
gctcaggcaa atggagtaag ccataatatt acctttgaaa gtccacctcc accaattgaa    2280
tggcatatca gcaaaccagg acagtttgaa acatttgatc tcatgacact tgatccaata    2340
gaaattgcac gtcagctgac acttttggag tctgatcttt acaggaaagt tcaaccgtct    2400
gaacttgtag ggagtgtgtg gaccaaagaa gataagaaa taaattctcc aaatttatta    2460
aaaatgattc gccataccac aaatctcacc ctctggtttg aaaaatgcat tgtggaagca    2520
gaaaattttg aagaacgggt ggcagtacta agtagaatta tagaaattct gcaagttttt    2580
```

```
caagatttga ataatttcaa tggcgtattg gagatagtca gtgcagtaaa ttcagtgtca    2640
gtatacagac tagaccatac ctttgaggca ctgcaggaaa ggaaaaggaa aattttggac    2700
gaagctgtgg aattaagtca agatcacttt aaaaaatacc tagtaaaact taagtcaatc    2760
aatccacctt gtgtgccttt ttttggaata tatttaacaa atattctgaa gaccgaagaa    2820
gggaataatg atttttttaaa aagaaaggga aaagatttaa tcaatttcag taagaggagg    2880
aaagtagctg aaattactgg agaaattcag cagtatcaga atcagcctta ctgtttacgg    2940
atagaaccag atatgaggag attctttgaa aaccttaacc ccatgggaag tgcatctgaa    3000
aaagagttta cagattattt gttcaacaag tcactagaaa ttgaacctcg aaactgcaaa    3060
cagccacctc gatttcctag gaaatcaact ttttccttaa aatctcctgg aataaggcct    3120
aacacaggcc gacatggctc tacctcaggt actttacgag gtcacccaac accattagaa    3180
agagaaccat gtaaaataag ctttagtcgg attgctgaaa ctgagctgga atcaacagtg    3240
tcagcaccaa cctctccaaa tacaccatct actccaccag tatctgcttc ttcagacctt    3300
agtgtatttt tagatgtgga tctcaacagc tcctgtggca gcaatagcat ctttgctcca    3360
gtgcttttgc cacattcaaa gtctttcttt agttcatgtg gtagtttaca taaactaagt    3420
gaagagcccc tgattcctcc tcctcttcct cctcgaaaaa agtttgatca tgatgcttca    3480
aattccaagg gaaatatgaa atctgatgat gatcctcctg ctattccacc gagacagcct    3540
cctcctccaa aggtaaaacc cagagttcct gttcctactg gtgcatttga tgggcctctg    3600
catagtccac ctccgccacc accaagagat cctcttcctg ataccctcc accagttccc    3660 cttcggcctc cagaacactt tataaactgt ccatttaatc ttcagccacc tccactgggg    3720
catcttcaca gagattcaga ctggctcaga gacattagta cgtgtccaaa ttcgccaagc    3780
actcctccta gcacaccctc tccaagggta ccgcgtcgat gctatgtgct cagttctagt    3840
cagaataatc ttgctcatcc tccagctccc cctgttccac caaggcagaa ttcaagccct    3900
catctgccaa aactgccacc aaagacttac aaacgggagc tttcgcaccc cccattgtac    3960
agactgcctt tgctagaaaa tgcagaaact ccccaatga                          3999

<210> SEQ ID NO 2
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 2
gagggtgaga tttgtggtat ggcga                                           25

<210> SEQ ID NO 3
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 3
tgaggaaagg tcttctgaac tcgct                                           25

<210> SEQ ID NO 4
<211> LENGTH: 25
<212> TYPE: DNA
<213> ORGANISM: Artificial Sequence
<220> FEATURE:
```

```
<223> OTHER INFORMATION: Antisense oligonucleotide

<400> SEQUENCE: 4
gcatgtggaa ggtagggagg caaga                                  25

<210> SEQ ID NO 5
<211> LENGTH: 23
<212> TYPE: DNA
<213> ORGANISM: Artificial Sequence
<220> FEATURE:
<223> OTHER INFORMATION: Antisense oligonucleotide

<400> SEQUENCE: 5
ccagctccat ggtgctcact gcg                                    23

<210> SEQ ID NO 6
<211> LENGTH: 25
<212> TYPE: DNA
<213> ORGANISM: Artificial Sequence
<220> FEATURE:
<223> OTHER INFORMATION: Reverse control oligonucleotide

<400> SEQUENCE: 6
agcggtatgg tgtttagagt gggag                                  25

<210> SEQ ID NO 7
<211> LENGTH: 25
<212> TYPE: DNA
<213> ORGANISM: Artificial Sequence
<220> FEATURE:
<223> OTHER INFORMATION: Reverse control oligonucleotide

<400> SEQUENCE: 7
tcgctcaagt cttctggaaa ggagt                                  25

<210> SEQ ID NO 8
<211> LENGTH: 25
<212> TYPE: DNA
<213> ORGANISM: Artificial Sequence
<220> FEATURE:
<223> OTHER INFORMATION: Reverse control oligonucleotide

<400> SEQUENCE: 8
agaacggagg gatggaaggt gtacg                                  25

<210> SEQ ID NO 9
<211> LENGTH: 23
<212> TYPE: DNA
<213> ORGANISM: Artificial Sequence
<220> FEATURE:
<223> OTHER INFORMATION: Reverse control oligonucleotide

<400> SEQUENCE: 9
gcgtcactcg tggtacctcg acc                                    23

<210> SEQ ID NO 10
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 10
tccagtaact cttgcgttcc catgg                                  25
```

```
<210> SEQ ID NO 11
<211> LENGTH: 25
<212> TYPE: DNA
<213> ORGANISM: Artificial Sequence
<220> FEATURE:
<223> OTHER INFORMATION: Reverse control oligonucleotide

<400> SEQUENCE: 11
ggtacccttg cgttctcaat gacct                                              25

<210> SEQ ID NO 12
<211> LENGTH: 25
<212> TYPE: DNA
<213> ORGANISM: Artificial Sequence
<220> FEATURE:
<223> OTHER INFORMATION: Antisense oligonucleotide

<400> SEQUENCE: 12
ccatagtgag gttgcatctg gtgcc                                              25

<210> SEQ ID NO 13
<211> LENGTH: 25
<212> TYPE: DNA
<213> ORGANISM: Artificial Sequence
<220> FEATURE:
<223> OTHER INFORMATION: Reverse control oligonucleotide

<400> SEQUENCE: 13
ccgtggtcta cgttggagtg atacc                                              25

<210> SEQ ID NO 14
<211> LENGTH: 1332
<212> TYPE: PRT
<213> ORGANISM: Homo sapiens

<400> SEQUENCE: 14
```

Met Gln Gln Ala Pro Gln Pro Tyr Glu Phe Phe Ser Glu Glu Asn Ser
 1               5                  10                  15

Pro Lys Trp Arg Gly Leu Leu Val Ser Ala Leu Arg Lys Val Gln Val
            20                  25                  30

Gln Val His Pro Thr Leu Ser Ala Asn Glu Glu Ser Leu Tyr Tyr Ile
        35                  40                  45

Glu Glu Leu Ile Phe Gln Leu Leu Asn Lys Leu Cys Met Ala Gln Pro
    50                  55                  60

Arg Thr Val Gln Asp Val Glu Glu Arg Val Gln Lys Thr Phe Pro His
65                  70                  75                  80

Pro Ile Asp Lys Trp Ala Ile Ala Asp Ala Gln Ser Ala Ile Glu Lys
                85                  90                  95

Arg Lys Arg Arg Asn Pro Leu Leu Leu Pro Val Asp Lys Ile His Pro
            100                 105                 110

Ser Leu Lys Glu Val Leu Gly Tyr Lys Val Asp Tyr His Val Ser Leu
        115                 120                 125

Tyr Ile Val Ala Val Leu Glu Tyr Ile Ser Ala Asp Ile Leu Lys Leu
    130                 135                 140

Ala Gly Asn Tyr Val Phe Asn Ile Arg His Tyr Glu Ile Ser Gln Gln
145                 150                 155                 160

Asp Ile Lys Val Ser Met Cys Ala Asp Lys Val Leu Met Asp Met Phe
                165                 170                 175

Asp Gln Asp Asp Ile Gly Leu Val Ser Leu Cys Glu Asp Glu Pro Cys
            180                 185                 190

-continued

```
Ser Ser Gly Glu Leu Asn Tyr Tyr Asp Leu Val Arg Thr Glu Ile Ala
        195                 200                 205

Glu Glu Arg Gln Tyr Leu Arg Glu Leu Asn Met Ile Ile Lys Val Phe
    210                 215                 220

Arg Glu Ala Phe Leu Ser Asp Arg Lys Leu Phe Lys Pro Ser Val Tyr
225                 230                 235                 240

Glu Lys Ile Phe Ser Asn Ile Ser Asp Ile His Glu Leu Thr Val Lys
                245                 250                 255

Leu Leu Gly Leu Ile Glu Asp Thr Val Glu Met Thr Asp Glu Ser Ser
            260                 265                 270

Pro His Pro Leu Ala Gly Ser Cys Phe Glu Asp Leu Ala Glu Glu Gln
        275                 280                 285

Ala Phe Asp Pro Tyr Glu Thr Leu Ser Gln Asp Ile Leu Ser Pro Glu
    290                 295                 300

Phe His Glu His Phe Asn Lys Leu Met Ala Arg Pro Ala Val Ala Leu
305                 310                 315                 320

His Phe Gln Ser Ile Ala Asp Gly Phe Lys Glu Ala Val Arg Tyr Val
                325                 330                 335

Leu Pro Arg Leu Met Leu Val Pro Val Tyr His Cys Trp His Tyr Phe
            340                 345                 350

Glu Leu Leu Lys Gln Leu Lys Ala Cys Ser Glu Glu Gln Glu Asp Arg
        355                 360                 365

Glu Cys Leu Asn Gln Ala Ile Thr Ala Leu Met Asn His Gln Gly Ser
    370                 375                 380

Met Asp Arg Ile Tyr Lys Gln Tyr Ser Pro Arg Arg Arg Pro Gly Asp
385                 390                 395                 400

Pro Val Cys Pro Phe Tyr Ser His Gln Leu Arg Ser Lys His Leu Ala
                405                 410                 415

Ile Lys Lys Met Asn Glu Ile Gln Lys Asn Ile Asp Gly Trp Glu Gly
            420                 425                 430

Lys Asp Ile Gly Gln Cys Cys Asn Glu Phe Ile Met Glu Gly Pro Leu
        435                 440                 445

Thr Arg Ile Gly Ala Lys His Glu Arg His Ile Phe Leu Phe Asp Gly
    450                 455                 460

Leu Met Ile Ser Cys Lys Pro Asn His Gly Gln Thr Arg Leu Pro Gly
465                 470                 475                 480

Tyr Thr Ser Ala Glu Tyr Arg Leu Lys Glu Lys Phe Val Met Arg Lys
                485                 490                 495

Ile Gln Ile Cys Asp Lys Glu Asp Thr Cys Glu His Lys His Ala Phe
            500                 505                 510

Glu Leu Val Ser Lys Asp Glu Asn Ser Ile Ile Phe Ala Ala Lys Ser
        515                 520                 525

Ala Glu Glu Lys Asn Asn Trp Met Ala Ala Leu Ile Ser Leu His Tyr
    530                 535                 540

Arg Ser Thr Leu Asp Arg Met Leu Asp Ser Val Leu Leu Lys Glu Glu
545                 550                 555                 560

Asn Glu Gln Pro Leu Arg Leu Pro Ser Pro Glu Val Tyr Arg Phe Val
                565                 570                 575

Val Lys Asp Ser Glu Glu Asn Ile Val Phe Glu Asp Asn Leu Gln Ser
            580                 585                 590

Arg Ser Gly Ile Pro Ile Ile Lys Gly Gly Thr Val Val Lys Leu Ile
        595                 600                 605

Glu Arg Leu Thr Tyr His Met Tyr Ala Asp Pro Asn Phe Val Arg Thr
```

-continued

```
                610                 615                 620
Phe Leu Thr Thr Tyr Arg Ser Phe Cys Lys Pro Gln Glu Leu Leu Ser
625                 630                 635                 640

Leu Leu Ile Glu Arg Phe Glu Ile Pro Glu Pro Glu Pro Thr Asp Ala
                645                 650                 655

Asp Lys Leu Ala Ile Glu Lys Gly Glu Gln Pro Ile Ser Ala Asp Leu
                660                 665                 670

Lys Arg Phe Arg Lys Glu Tyr Val Gln Pro Val Gln Leu Arg Val Leu
            675                 680                 685

Asn Val Phe Arg His Trp Val Asp His His Tyr Tyr Asp Phe Glu Arg
690                 695                 700

Asp Leu Glu Leu Leu Glu Arg Leu Glu Ser Phe Ile Ser Ser Val Arg
705                 710                 715                 720

Gly Lys Ala Met Lys Lys Trp Val Glu Ser Ile Ala Lys Ile Ile Arg
                725                 730                 735

Arg Lys Lys Gln Ala Gln Ala Asn Gly Val Ser His Asn Ile Thr Phe
                740                 745                 750

Glu Ser Pro Pro Pro Ile Glu Trp His Ile Ser Lys Pro Gly Gln
                755                 760                 765

Phe Glu Thr Phe Asp Leu Met Thr Leu Asp Pro Ile Glu Ile Ala Arg
                770                 775                 780

Gln Leu Thr Leu Leu Glu Ser Asp Leu Tyr Arg Lys Val Gln Pro Ser
785                 790                 795                 800

Glu Leu Val Gly Ser Val Trp Thr Lys Glu Asp Lys Glu Ile Asn Ser
                805                 810                 815

Pro Asn Leu Leu Lys Met Ile Arg His Thr Thr Asn Leu Thr Leu Trp
                820                 825                 830

Phe Glu Lys Cys Ile Val Glu Ala Glu Asn Phe Glu Glu Arg Val Ala
                835                 840                 845

Val Leu Ser Arg Ile Ile Glu Ile Leu Gln Val Phe Gln Asp Leu Asn
                850                 855                 860

Asn Phe Asn Gly Val Leu Glu Ile Val Ser Ala Val Asn Ser Val Ser
865                 870                 875                 880

Val Tyr Arg Leu Asp His Thr Phe Glu Ala Leu Gln Glu Arg Lys Arg
                885                 890                 895

Lys Ile Leu Asp Glu Ala Val Glu Leu Ser Gln Asp His Phe Lys Lys
                900                 905                 910

Tyr Leu Val Lys Leu Lys Ser Ile Asn Pro Pro Cys Val Pro Phe Phe
            915                 920                 925

Gly Ile Tyr Leu Thr Asn Ile Leu Lys Thr Glu Glu Gly Asn Asn Asp
930                 935                 940

Phe Leu Lys Arg Lys Gly Lys Asp Leu Ile Asn Phe Ser Lys Arg Arg
945                 950                 955                 960

Lys Val Ala Glu Ile Thr Gly Glu Ile Gln Gln Tyr Gln Asn Gln Pro
                965                 970                 975

Tyr Cys Leu Arg Ile Glu Pro Asp Met Arg Arg Phe Phe Glu Asn Leu
                980                 985                 990

Asn Pro Met Gly Ser Ala Ser Glu Lys Glu Phe Thr Asp Tyr Leu Phe
                995                 1000                1005

Asn Lys Ser Leu Glu Ile Glu Pro Arg Asn Cys Lys Gln Pro Pro Arg
                1010                1015                1020

Phe Pro Arg Lys Ser Thr Phe Ser Leu Lys Ser Pro Gly Ile Arg Pro
1025                1030                1035                1040
```

```
Asn Thr Gly Arg His Gly Ser Thr Ser Gly Thr Leu Arg Gly His Pro
            1045                1050                1055

Thr Pro Leu Glu Arg Glu Pro Cys Lys Ile Ser Phe Ser Arg Ile Ala
            1060                1065                1070

Glu Thr Glu Leu Glu Ser Thr Val Ser Ala Pro Thr Ser Pro Asn Thr
            1075                1080                1085

Pro Ser Thr Pro Pro Val Ser Ala Ser Ser Asp Leu Ser Val Phe Leu
            1090                1095                1100

Asp Val Asp Leu Asn Ser Ser Cys Gly Ser Asn Ser Ile Phe Ala Pro
1105                1110                1115                1120

Val Leu Leu Pro His Ser Lys Ser Phe Phe Ser Ser Cys Gly Ser Leu
            1125                1130                1135

His Lys Leu Ser Glu Glu Pro Leu Ile Pro Pro Pro Leu Pro Pro Arg
            1140                1145                1150

Lys Lys Phe Asp His Asp Ala Ser Asn Ser Lys Gly Asn Met Lys Ser
            1155                1160                1165

Asp Asp Asp Pro Pro Ala Ile Pro Pro Arg Gln Pro Pro Pro Pro Lys
1170                1175                1180

Val Lys Pro Arg Val Pro Val Pro Thr Gly Ala Phe Asp Gly Pro Leu
1185                1190                1195                1200

His Ser Pro Pro Pro Pro Pro Arg Asp Pro Leu Pro Asp Thr Pro
            1205                1210                1215

Pro Pro Val Pro Leu Arg Pro Pro Glu His Phe Ile Asn Cys Pro Phe
            1220                1225                1230

Asn Leu Gln Pro Pro Pro Leu Gly His Leu His Arg Asp Ser Asp Trp
            1235                1240                1245

Leu Arg Asp Ile Ser Thr Cys Pro Asn Ser Pro Ser Thr Pro Pro Ser
            1250                1255                1260

Thr Pro Ser Pro Arg Val Pro Arg Arg Cys Tyr Val Leu Ser Ser Ser
1265                1270                1275                1280

Gln Asn Asn Leu Ala His Pro Pro Ala Pro Pro Val Pro Pro Arg Gln
            1285                1290                1295

Asn Ser Ser Pro His Leu Pro Lys Leu Pro Pro Lys Thr Tyr Lys Arg
            1300                1305                1310

Glu Leu Ser His Pro Pro Leu Tyr Arg Leu Pro Leu Leu Glu Asn Ala
            1315                1320                1325

Glu Thr Pro Gln
    1330
```

SOS1 INHIBITORS

BACKGROUND OF THE INVENTION

1. Field of the Invention

The present invention provides methods and compositions for modulating the expression of Sos1, and antisense and ribozyme compounds specifically hybridizable with Sos1.

2. Description of the Related Art

The deregulation of receptor tyrosine kinases (RTKs) or intracellular tyrosine kinases coupled to Ras activation has been involved in the development of a number of tumors, such as breast, ovarian cancer and leukemia (Pandey et al., *Cancer Res.* 55:4000-03, 1995; Gishizky, M., *Annu. Rep. Med. Chem.* 30:247-53, 1995).

Activated RTKs recruit the adaptor protein Grb2 and the guanine nucleotide exchange factor Sos1 to the plasma membrane. Here, Sos1 stimulates the nucleotide exchange on Ras GDP to Ras GTP which leads to a conformational change and activation of Ras. Ras GTP activates several known downstream signaling pathways.

As Sos1 plays a crucial role in the coupling of RTKs and also intracellular tyrosine kinases to Ras activation, there is a need in the art for methods and compositions capable of inhibiting Sos1 activity.

BRIEF SUMMARY OF THE INVENTION

The present invention provides, in one embodiment, inhibitors of Sos1. Inventive inhibitors include, but are not limited to, antisense molecules, ribozymes, RNAi, antibodies or antibody fragments, proteins or polypeptides as well as small molecules. Exemplary antisense molecules comprise at least 10, 15 or 20 consecutive nucleotides of, or that hybridize under stringent conditions to the polynucleotide of SEQ ID NO: 1. More preferred are antisense molecules that comprise at least 25 consecutive nucleotides of, or that hybridize under stringent conditions to the sequence of SEQ ID NO: 1. Representative antisense molecules are provided herein as SEQ ID NOs:2 and 3.

In further embodiments, compositions are provided that comprise one or more Sos1 inhibitors in a pharmaceutically acceptable carrier.

Additional embodiments provide methods of decreasing Sos1 gene expression or biological activity.

The invention provides an antisense oligonucleotide comprising at least one modified internucleoside linkage.

The invention further provides an antisense oligonucleotide having a phosphorothioate linkage.

The invention still further provides an antisense oligonucleotide comprising at least one modified sugar moiety.

The invention also provides an antisense oligonucleotide comprising at least one modified sugar moiety which is a 2'-O-methyl sugar moiety.

The invention further provides an antisense oligonucleotide comprising at least one modified nucleobase.

The invention still further provides an antisense oligonucleotide having a modified nucleobase wherein the modified nucleobase is 5-methylcytosine.

The invention also provides an antisense compound wherein the antisense compound is a chimeric oligonucleotide.

The invention provides a method of inhibiting the expression of human Sos1 in human cells or tissues comprising contacting the cells or tissues in vivo with an antisense compound or a ribozyme of 8 to 35 nucleotides in length targeted to a nucleic acid molecule encoding human Sos1 so that expression of human Sos1 is inhibited.

The invention further provides a method of modulating growth of cancer cells comprising contacting the cancer cells in vivo with an antisense compound or ribozyme of 8 to 35 nucleotides in length targeted to a nucleic acid molecule encoding human Sos1 so that expression of human Sos1 is inhibited.

The invention still further provides for identifying target regions of Sos1 polynucleotides. The invention also provides labeled probes for identifying Sos1 polynucleotides by in situ hybridization.

The invention provides for the use of an Sos1 inhibitor according to the invention to prepare a medicament for modulating cell proliferation.

The invention also provides a pharmaceutical composition for inhibiting expression of the Sos1, comprising an antisense oligonucleotide according to the invention in a mixture with a physiologically acceptable carrier or diluent.

The invention further provides a ribozyme capable of specifically cleaving Sos1 RNA, and a pharmaceutical composition comprising the ribozyme.

The invention also provides small molecule inhibitors of Sos1 wherein the inhibitors are capable of reducing the activity of Sos 1 or of reducing or preventing the expression of Sos1 mRNA.

The invention therefore provides an isolated Sos1 inhibitor selected from the group consisting of an antisense oligonucleotide, a ribozyme, a protein, a polypeptide, an antibody, and a small molecule.

In a specific embodiment, the isolated Sos1 inhibitor is an antisense molecule.

In a more specific embodiment, the isolated Sos1 inhibitor antisense molecule or the complement thereof comprises at least 10 consecutive nucleic acids of the sequence of SEQ ID NO: 1.

In another specific embodiment, the isolated Sos1 inhibitor antisense molecule or the complement thereof hybridizes under high stringency conditions to the sequence of SEQ ID NO: 1.

In specific embodiments, the isolated Sos1 inhibitor antisense molecule comprises a nucleic acid sequence selected from the group consisting of SEQ ID NOs:2 and 3.

In another embodiment, the isolated Sos1 inhibitor is a ribozyme, and in yet other embodiments, the isolated Sos1 inhibitor is selected from the group consisting of an antibody and an antibody fragment.

The invention further provides a composition comprising a therapeutically effective amount of a Sos1 inhibitor in a pharmaceutically acceptable carrier.

In certain embodiments, the composition comprises two or more Sos1 inhibitors in the composition, and the Sos1 inhibitor is an antisense molecule.

In specific embodiments of the composition, the antisense molecule or the complement thereof comprises at least 10 consecutive nucleic acids of the sequence of SEQ ID NO: 1, and in more specific embodiments of the composition, the antisense molecule comprises a nucleic acid sequence selected from the group consisting of SEQ ID NOs:2 and 3.

The invention yet further provides a method of inhibiting the expression of Sos1 in a mammalian cell, comprising administering to said cell an Sos1 inhibitor selected from the group consisting of an antisense oligonucleotide, a ribozyme, a protein, a polypeptide, an antibody, and a small molecule.

In certain embodiments of this method, the Sos1 inhibitor is an antisense molecule.

The invention still further provides a method of inhibiting the expression of Sos1 gene expression in a subject, comprising administering to said subject, in a pharmaceutically effective vehicle, an amount of an antisense oligonucleotide which is effective to specifically hybridize to all or part of a selected target nucleic acid sequence derived from said Sos1 gene.

In certain embodiments of this method, the antisense oligonucleotide is selected from the group consisting of SEQ ID NOs:2 and 3.

The invention also provides a method of treating neoplastic disease, comprising administering to a mammalian cell an Sos1 inhibitor selected from group consisting of an antisense oligonucleotide, a ribozyme, a protein, a polypeptide, an antibody, and a small molecule such that the neoplastic disease is reduced in severity.

Other embodiments provide an antisense compound of 8 to 35 nucleotides in length targeted to a nucleic acid molecule encoding human Sos1, wherein the antisense compound inhibits the expression of human Sos 1, and an isolated polynucleotide with a sequence comprising a transcriptional initiation region and a sequence encoding an antisense oligonucleotide at least 8 nucleotides or nucleotide analogues and not longer than 35 nucleotides in length comprising a sequence selected from the group consisting of SEQ ID NOs:2 and 3.

Also provided is a recombinant vector comprising a polynucleotide with a sequence comprising a transcriptional initiation region and a sequence encoding an antisense oligonucleotide at least 8 nucleotides or nucleotide analogues and not longer than 35 nucleotides in length comprising a sequence selected from the group consisting of SEQ ID NOs:2 and 3.

BRIEF DESCRIPTION OF THE DRAWINGS

FIG. 1 is a Sos1 polynucleotide (SEQ ID NO: 1).

FIG. 2 is a Sos1 polypeptide (SEQ ID NO:14).

DETAILED DESCRIPTION OF THE INVENTION

Introduction

Figure 3A:
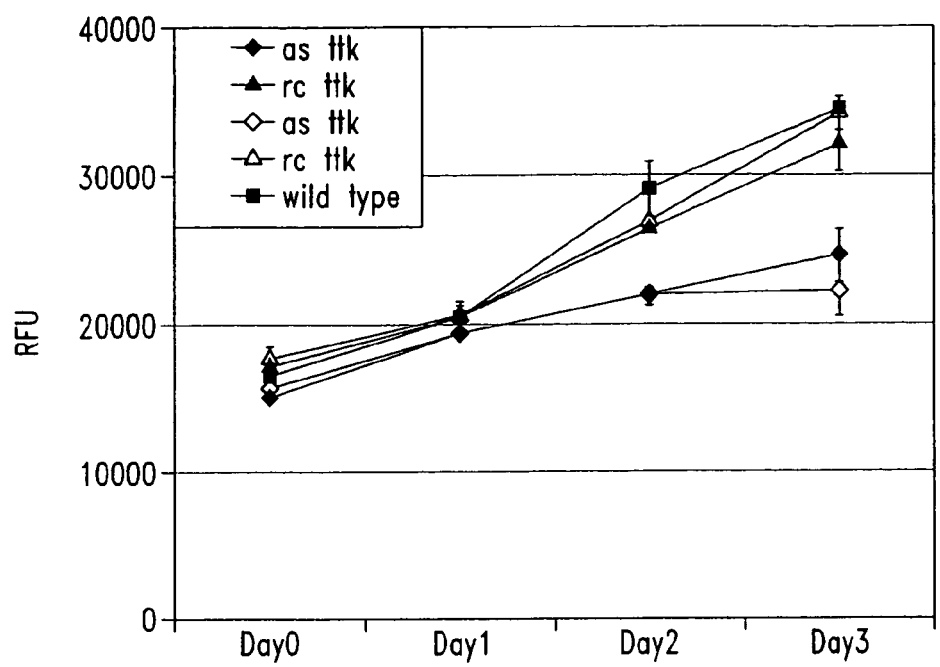
FIG. 3 shows the results of a proliferation assay of SW620 cells transfected with the following oligonucleotides: (3A) ttk antisense and reverse control (SEQ ID NO:10 and 11); (3B) kras antisense and reverse control (SEQ ID NO:4 and 8); (3C) Sos1 (CHIR153-2) antisense and reverse control (SEQ ID NO:2 and 6); and (3D) Sos1 (CHIR153-4) antisense and control (SEQ ID NO:3 and 7).

The invention relates to the use of inhibitors, preferably oligonucleotides, such as antisense molecules or ribozymes, to target and modulate the expression of polynucleotides comprising an Sos1 nucleotide sequence. Preventing the Ras specific nucleotide exchange activity of Sos1 should lead to growth arrest of proliferative cells.

In mammals, three types of Ras-specific guanine nucleotide exchange factors have been identified. One of these groups contains the Sos1 and Sos2 proteins, which have been implicated in signals induced by activated protein tyrosine kinases. These kinases are coupled to Sos through adaptor proteins. Upon PTK activation, the Grb2/Sos complex is recruited to the plasma membrane, which leads to the exchange of the nucleotide on plasma membrane localized Ras. Complex formation with PTKs occurs either by binding to the SH2 domain of the adaptor protein Grb2, or by binding a second adaptor protein that in turn simultaneously binds to the SH2 domain of Grb2 and to the activated tyrosine protein kinase.

During mammalian development, sos1 appears to play a crucial role, as homozygous null animals do not survive mid-gestation. The expression of Sos2 does not appear to compensate for this defect, suggesting that the roles of sos1 and sos2 differ during development. Qian et al., *EMBO Journal* 19:642-54, 2000, suggest that Sos1 can participate in both short-term and long-term signals, thereby playing an important role in Ras-related signaling. A relationship between Sos1 function and cancer has been shown. For example, Pandey et al., *Cancer Res.* 55:4000-03, 1995, found that the DF3MUC1 mucin-like glycoprotein is overexpressed in human breast carcinomas. When this glycoprotein is phosphorylated via tyrosine phosphorylation, Grb2 is bound, and the resulting DF3/Grb2 complex associates with Sos. In turn, the DF3/Grb2/Sos complex formation indicates that DF3 could play a role in intracellular signaling, as the Sos/Grb2 interaction is associated with Ras at the cell membrane.

Hart et al. (*Am. J. Human Genet.* 70:943-954, 2002) identified a mutation in the Sos1 gene of individuals with hereditary gingival fibromatosis. This disease is a rare, autosomal dominant form of gingival overgrowth. Affected individuals have a benign, slowly progressive, nonhemorrahagic, fibrous enlargement of the oral masticatory mucosa. One dominant form has been mapped to 2p21. Sibilia et al., (*Cell* 102:211-220, 2001) reported that a transgenic mouse construct with a comparable Sos1 mutation was found to produce a phenotype with skin hypertrophy.

In an extensive family with hereditary gingival fibromatosis, it was demonstrated that the disorder was caused by insertion of cytosine between nucleotides 126142 and 126143 in codon 1083 of the Sos1 gene. Hart, et al., *Am. J. Hum. Genet.* 70:943-954, 2002. The insertion mutation was reported to introduce a frameshift and create a premature stop codon, abolishing four functionally important proline-rich SH3 binding domains normally present in the carboxyl-terminal region of the Sos1 protein. In the cDNA sequence, the insertion was between nucleotides 3248 and 3249. The mutation yielded a chimeric 1,105-amino acid protein that consisted of 1,083 Sos1 N-terminal amino acids in a normal sequence, followed by 22 replaced amino acids and a premature stop codon at codon 1106.

Sos1 (−/−) cells can be readily transformed by activated Ras but are resistant to transformation by v-src or overexpressed EGF-Rs (Qian et al., *EMBO J.* 19:642, 2000). Because of the crucial role of Sos1 in nucleotide exchange and thereby activation of Ras, it was of interest to determine whether Sos 1 expression can be affected in cancer cells, and if manipulation of Sos1 expression plays a role in tumor cell growth and/or survival. These studies were carried out using antisense inhibitors of Sos1, as described in detail herein.

The invention relates to antisense oligonucleotides specific for Sos1, which lead to the reduction of Sos1 mRNA levels in the human cancer cell lines SW620 (colon) and BT474 (breast). Preferred Sos1 antisense oligonucleotide sequences are:

(CHIR-153-2)    5'GAGGGTGAGATTTGTGGTATGGCGA3'    (SEQ ID NO:2)

(CHIR-153-4)    5'TGAGGAAAGGTCTTCTGAACTCGCT3'    (SEQ ID NO:3)

The corresponding reverse control of oligonucleotide sequences are SEQ ID NO:6 and 7. These antisense oligonucleotides may revert the transformed phenotype of cancer cell lines with respect to focus formation, decrease in proliferation, and stimulation of apoptosis. Because inhibition of nucleotide exchange on Ras may revert the phenotype of RTK-transformed cell lines, Sos1 is a putative therapeutic target for Sos1 antisense or a small molecule.

Two antisense oligonucleotides that are capable of hybridizing with Sos1 polynucleotides led to a reduction in Sos1 mRNA levels when transfected into SW620 cells. SEQ ID NO:2 caused a 79.8% reduction and SEQ ID NO:3 caused an 83% reduction. Antisense oligos specific for akt1 and kras were used as controls and caused 94.2% and 78.9% reduction of the respective mRNA levels.

These antisense oligonucleotides were also transfected into BT474 cells, a human breast carcinoma cell line that overexpresses Her2/neu. SEQ ID NO:2 caused a 69.2% reduction in Sos1 mRNA level, while Kras antisense caused a 79.3% reduction in kras, and Her2/neu antisense caused a 60.7% reduction in Her2/neu mRNA level.

Although antisense oligonucleotides specific for Sos1 decreased Sos1 mRNA levels in both cell lines, proliferation was only affected in BT474 cells. SEQ ID NO:2 and 3 had no effect on proliferation of SW620 cells, whereas SEQ ID NO: 2 significantly decreased BT474 proliferation over 4 days following transfection.

Oligonucleotides for Targeting Sos1 Polynucleotides

According to the present invention, oligonucleotide molecules capable of hybridizing with Sos1 polynucleotides inhibited the proliferation of a human breast cancer cell line, BT474. This cell line is a standard model for breast cancer cell proliferation and growth in vivo, and the results support in vivo use of the Sos1 antisense molecules to ameliorate breast cancer in humans and other mammals. The SW620 cell line is an established model system for colon cancer.

The present invention relates to antisense oligonucleotides directed to Sos1 polynucleotides. Transfecting SW620 cells with a plasmid encoding antisense FasL cDNA suggests that impairing FasL translation can inhibit tumor progression (Nyhus et al., *Gene Ther.* 8:209-14, 2001). p53 antisense oligonucleotides inhibited the growth of SW620 (Hirota et al., *Jpn. J Cancer Res.* 87:635-42, 1996). Reducing matrilysin levels in SW620 cells through antisense treatment has been suggested as a method for reducing tumorigenicity and progression of colorectal tumors (Witty et al., *Cancer Res.* 54:4805-12, 1994). The present invention adds to this knowledge about treating cancer cells by disclosing for the first time that antisense oligonucleotides directed against Sos1 are suitable agents for treating breast cancer.

Included within the scope of the invention are oligonucleotides capable of hybridizing with Sos1 DNA or RNA, referred to as the target polynucleotide. An oligonucleotide need not be 100% complementary to the target polynucleotide, as long as specific hybridization is achieved. The degree of hybridization to be achieved is that which interferes with the normal function of the target polynucleotide, be it transcription, translation, pairing with a complementary sequence, or binding with another biological component such as a protein. An antisense oligonucleotide can interfere with DNA replication and transcription, and it can interfere with RNA translocation, translation, splicing, and catalytic activity.

The invention includes within its scope any oligonucleotide of about 8 to about 35 nucleotides in length, including variations as described herein, wherein the oligonucleotide hybridizes to a Sos1 polynucleotide, including DNA or mRNA, such that an effect on the normal function of the polynucleotide is achieved. The oligonucleotide can be 8, 10, 15, 17, 18, 20, 22, 25, 28, 30, 32 or 35 nucleotides in length. The nucleotide sequence of Sos1 is shown in FIG. 1 (SEQ ID NO: 1). Preferred antisense oligonucleotides include:

(CHIR-153-2)    5'GAGGGTGAGATTTGTGGTATGGCGA3'    (SEQ ID NO:2)

(CHIR-153-4)    5'TGAGGAAAGGTCTTCTGAACTCGCT3'    (SEQ ID NO:3)

The antitumor use of the oligonucleotides disclosed herein is based on the discovery that Sos1 antisense oligonucleotides can reduce Sos1 mRNA levels in tumor cells, and can inhibit proliferation of tumor cells. To measure the effect on mRNA, tumor cells were incubated with a transfection mixture of an oligonucleotide and a carrier, specifically a lipitoid or cholesteroid, although other carriers can be used as is known in the art. The transfection mixture was left on the cells during the whole experiment.

Total RNA was extracted from the cells, reverse transcribed, and amplified as described in the Examples. Transfection of the cells with any one of the antisense oligonucleotides (SEQ ID NOs:2 and 3) reduced the Sos1 mRNA levels relative to β-actin.

Examples of preferred antisense compounds useful in the invention are based on SEQ ID NOs:2 and 3, and include oligonucleotides containing modified backbones or non-natural internucleoside linkages. Oligonucleotides having modified backbones include those retaining a phosphorus atom in the backbone, and those that do not have a phosphorus atom in the backbone. Preferred modified oligonucleotide backbones include phosphorothioates, chiral phosphorothioates, phosphotriesters, aminoalkylphosphotriesters, methyl and other alkyl phosphonates including 3'-alkylene phosphonates and chiral phosphonates, phosphinates, phosphoroamidates including 3'-amino phosphoroamidate and aminoalkylphosphoroamidates, thiophosphoroamidates, thioalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts, and free acid forms are also included.

Examples of 20-mer oligonucleotides include the following oligonucleotides, indicated by polynucleotide positions with reference to SEQ ID NO: 1: 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100, 82-101, 83-102, 84-103, 85-104, 86-105, 87-106, 88-107, 89-108, 90-109, 91-110, 92-111, 93-112, 94-113, 95-114, 96-115, 97-116, 98-117, 99-118, 100-119, 101-120, 102-121, 103-122, 104-123, 105-124, 106-125, 107-126, 108-127, 109-128, 110-129, 111-130, 112-131, 113-132, 114-133, 115-134, 116-135, 117-136, 118-137, 119-138, 120-139, 121-140, 122-141, 123-142, 124-143, 125-144, 126-145, 127-146, 128-147, 129-148, 130-149, 131-150, 132-151, 133-152, 134-153, 135-154, 136-155, 137-156, 138-157, 139-158, 140-159, 141-160, 142-161, 143-162, 144-163, 145-164, 146-165, 147-166, 148-167, 149-168, 150-169, 151-170, 152-171, 153-172, 154-173, 155-174, 156-175, 157-176, 158-177, 159-178, 160-179, 161-180, 162-181, 163-182, 164-183, 165-184, 166-185, 167-186, 168-187, 169-188, 170-189, 171-190, 172-191, 173-192, 174-193, 175-194, 176-195, 177-196, 178-197, 179-198, 180-199, 181-200, 182-201, 183-202, 184-203, 185-204, 186-205, 187-206, 188-207, 189-208, 190-209, 191-210, 192-211, 193-212, 194-213, 195-214, 196-215, 197-216, 198-217, 199-218, 200-219, 201-220, 202-221, 203-222, 204-223, 205-224, 206-225, 207-226, 208-227, 209-228, 210-229, 211-230, 212-231, 213-232, 214-233, 215-234, 216-235, 217-236, 218-237, 219-238, 220-239, 221-240, 222-241, 223-242, 224-243, 225-244, 226-245, 227-246, 228-247, 229-248, 230-249, 231-250, 232-251, 233-252, 234-253, 235-254, 236-255, 237-256, 238-257, 239-258, 240-259, 241-260, 242-261, 243-262, 244-263, 245-264, 246-265, 247-266, 248-267, 249-268, 250-269, 251-270, 252-271, 253-272, 254-273, 255-274, 256-275, 257-276, 258-277, 259-278, 260-279, 261-280, 262-281, 263-282, 264-283, 265-284, 266-285, 267-286, 268-287, 269-288, 270-289, 271-290, 272-291, 273-292, 274-293, 275-294, 276-295, 277-296, 278-297, 279-298, 280-299, 281-300, 282-301, 283-302, 284-303, 285-304, 286-305, 287-306, 288-307, 289-308, 290-309, 291-310, 292-311, 293-312, 294-313, 295-314, 296-315, 297-316, 298-317, 299-318, 300-319, 301-320, 302-321, 303-322, 304-323, 305-324, 306-325, 307-326, 308-327, 309-328, 310-329, 311-330, 312-331, 313-332, 314-333, 315-334, 316-335, 317-336, 318-337, 319-338, 320-339, 321-340, 322-341, 323-342, 324-343, 325-344, 326-345, 327-346, 328-347, 329-348, 330-349, 331-350, 332-351, 333-352, 334-353, 335-354, 336-355, 337-356, 338-357, 339-358, 340-359, 341-360, 342-361, 343-362, 344-363, 345-364, 346-365, 347-366, 348-367, 349-368, 350-369, 351-370, 352-371, 353-372, 354-373, 355-374, 356-375, 357-376, 358-377, 359-378, 360-379, 361-380, 362-381, 363-382, 364-383, 365-384, 366-385, 367-386, 368-387, 369-388, 370-389, 371-390, 372-391, 373-392, 374-393, 375-394, 376-395, 377-396, 378-397, 379-398, 380-399, 381-400, 382-401, 383-402, 384-403, 385-404, 386-405, 387-406, 388-407, 389-408, 390-409, 391-410, 392-411, 393-412, 394-413, 395-414, 396-415, 397-416, 398-417, 399-418, 400-419, 401-420, 402-421, 403-422, 404-423, 405-424, 406-425, 407-426, 408-427, 409-428, 410-429, 411-430, 412-431, 413432, 414-433, 415-434, 416-435, 417-436, 418-437, 419-438, 420-439, 421-440, 422-441, 423-442, 424-443, 425-444, 426-445, 427-446, 428-447, 429-448, 430-449, 431-450, 432-451, 433-452, 434-453, 435-454, 436-455, 437-456, 438-457, 439-458, 440-459, 441-460, 442-461, 443-462, 444-463, 445-464, 446-465, 447-466, 448-467, 449-468, 450-469, 451-470, 452-471, 453-472, 454-473, 455-474, 456-475, 457-476, 458-477, 459-478, 460-479, 461-480, 462-481, 463-482, 464-483, 465-484, 466-485, 467-486, 468-487, 469-488, 470-489, 471-490, 472-491, 473-492, 474-493, 475-494, 476-495, 477-496, 478-497, 479-498, 480-499, 481-500, 482-501, 483-502, 484-503, 485-504, 486-505, 487-506, 488-507, 489-508, 490-509, 491-510, 492-511, 493-512, 494-513, 495-514, 496-515, 497-516, 498-517, 499-518, 500-519, 501-520, 502-521, 503-522, 504-523, 505-524, 506-525, 507-526, 508-527, 509-528, 510-529, 511-530, 512-531, 513-532, 514-533, 515-534, 516-535, 517-536, 518-537, 519-538, 520-539, 521-540, 522-541, 523-542, 524-543, 525-544, 526-545, 527-546, 528-547, 529-548, 530-549, 531-550, 532-551, 533-552, 534-553, 535-554, 536-555, 537-556, 538-557, 539-558, 540-559, 541-560, 542-561, 543-562, 544-563, 545-564, 546-565, 547-566, 548-567, 549-568, 550-569, 551-570, 552-571, 553-572, 554-573, 555-574, 556-575, 557-576, 558-577, 559-578, 560-579, 561-580, 562-581, 563-582, 564-583, 565-584, 566-585, 567-586, 568-587, 569-588, 570-589, 571-590, 572-591, 573-592, 574-593, 575-594, 576-595, 577-596, 578-597, 579-598, 580-599, 581-600, 582-601, 583-602, 584-603, 585-604, 586-605, 587-606, 588-607, 589-608, 590-609, 591-610, 592-611, 593-612, 594-613, 595-614, 596-615, 597-616, 598-617, 599-618, 600-619, 601-620, 602-621, 603-622, 604-623, 605-624, 606-625, 607-626, 608-627, 609-628, 610-629, 611-630, 612-631, 613-632, 614-633, 615-634, 616-635, 617-636, 618-637, 619-638, 620-639, 621-640, 622-641, 623-642, 624-643, 625-644, 626-645, 627-646, 628-647, 629-648, 630-649, 631-650, 632-651, 633-652, 634-653, 635-654, 636-655, 637-656, 638-657, 639-658, 640-659, 641-660, 642-661, 643-662, 644-663, 645-664, 646-665, 647-666, 648-667, 649-668, 650-669, 651-670, 652-671, 653-672, 654-673, 655-674, 656-675, 657-676, 658-677, 659-678, 660-679, 661-680, 662-681, 663-682, 664-683, 665-684, 666-685, 667-686, 668-687, 669-688, 670-689, 671-690, 672-691, 673-692, 674-693, 675-694, 676-695, 677-696, 678-697, 679-698, 680-699, 681-700, 682-701, 683-702, 684-703, 685-704, 686-705, 687-706, 688-707, 689-708, 690-709, 691-710, 692-711, 693-712, 694-713, 695-714, 696-715, 697-716, 698-717, 699-718, 700-719, 701-720, 702-721, 703-722, 704-723, 705-724, 706-725, 707-726, 708-727, 709-728, 710-729, 711-730, 712-731, 713-732, 714-733, 715-734, 716-735, 717-736, 718-737, 719-738, 720-739, 721-740, 722-741, 723-742, 724-743, 725-744, 726-745, 727-746, 728-747, 729-748, 730-749, 731-750, 732-751, 733-752, 734-753, 735-754, 736-755, 737-756, 738-757, 739-758, 740-759, 741-760, 742-761, 743-762, 744-763, 745-764, 746-765, 747-766, 748-767, 749-768, 750-769, 751-770, 752-771, 753-772, 754-773, 755-774, 756-775, 757-776, 758-777, 759-778, 760-779, 761-780, 762-781, 763-782, 764-783, 765-784, 766-785, 767-786, 768-787, 769-788, 770-789, 771-790, 772-791, 773-792, 774-793, 775-794, 776-795, 777-796, 778-797, 779-798, 780-799, 781-800, 782-801, 783-802, 784-803, 785-804, 786-805, 787-806, 788-807, 789-808, 790-809, 791-810, 792-811, 793-812, 794-813, 795-814, 796-815, 797-816, 798-817, 799-818, 800-819, 801-820, 802-821, 803-822, 804-823, 805-824, 806-825, 807-826, 808-827, 809-828, 810-829, 811-830, 812-831, 813-832, 814-833, 815-834, 816-835, 817-836, 818-837, 819-838, 820-839, 821-840, 822-841, 823-842, 824-843, 825-844, 826-845, 827-846, 828-847, 829-848, 830-849, 831-850, 832-851, 833-852, 834-853, 835-854, 836-855, 837-856, 838-857, 839-858, 840-859, 841-860, 842-861, 843-862, 844-863, 845-864, 846-865, 847-866, 848-867, 849-868, 850-869, 851-870, 852-871, 853-872, 854-873, 855-874, 856-875, 857-876, 858-877, 859-878, 860-879, 861-880, 862-881, 863-882, 864-883, 865-884, 866-885, 867-886, 868-887, 869-888, 870-889, 871-890, 872-891, 873-892, 874-893, 875-894, 876-895, 877-896, 878-897, 879-

898, 880-899, 881-900, 882-901, 883-902, 884-903, 885-904, 886-905, 887-906, 888-907, 889-908, 890-909, 891-910, 892-911, 893-912, 894-913, 895-914, 896-915, 897-916, 898-917, 899-918, 900-919, 901-920, 902-921, 903-922, 904-923, 905-924, 906-925, 907-926, 908-927, 909-928, 910-929, 911-930, 912-931, 913-932, 914-933, 915-934, 916-935, 917-936, 918-937, 919-938, 920-939, 921-940, 922-941, 923-942, 924-943, 925-944, 926-945, 927-946, 928-947, 929-948, 930-949, 931-950, 932-951, 933-952, 934-953, 935-954, 936-955, 937-956, 938-957, 939-958, 940-959, 941-960, 942-961, 943-962, 944-963, 945-964, 946-965, 947-966, 948-967, 949-968, 950-969, 951-970, 952-971, 953-972, 954-973, 955-974, 956-975, 957-976, 958-977, 959-978, 960-979, 961-980, 962-981, 963-982, 964-983, 965-984, 966-985, 967-986, 968-987, 969-988, 970-989, 971-990, 972-991, 973-992, 974-993, 975-994, 976-995, 977-996, 978-997, 979-998, 980-999, 981-1000, 982-1001, 983-1002, 984-1003, 985-1004, 986-1005, 987-1006, 988-1007, 989-1008, 990-1009, 991-1010, 992-1011, 993-1012, 994-1013, 995-1014, 996-1015, 997-1016, 998-1017, 999-1018, 1000-1019, 1001-1020, 1002-1021, 1003-1022, 1004-1023, 1005-1024, 1006-1025, 1007-1026, 1008-1027, 1009-1028, 1010-1029, 1011-1030, 1012-1031, 1013-1032, 1014-1033, 1015-1034, 1016-1035, 1017-1036, 1018-1037, 1019-1038, 1020-1039, 1021-1040, 1022-1041, 1023-1042, 1024-1043, 1025-1044, 1026-1045, 1027-1046, 1028-1047, 1029-1048, 1030-1049, 1031-1050, 1032-1051, 1033-1052, 1034-1053, 1035-1054, 1036-1055, 1037-1056, 1038-1057, 1039-1058, 1040-1059, 1041-1060, 1042-1061, 1043-1062, 1044-1063, 1045-1064, 1046-1065, 1047-1066, 1048-1067, 1049-1068, 1050-1069, 1051-1070, 1052-1071, 1053-1072, 1054-1073, 1055-1074, 1056-1075, 1057-1076, 1058-1077, 1059-1078, 1060-1079, 1061-1080, 1062-1081, 1063-1082, 1064-1083, 1065-1084, 1066-1085, 1067-1086, 1068-1087, 1069-1088, 1070-1089, 1071-1090, 1072-1091, 1073-1092, 1074-1093, 1075-1094, 1076-1095, 1077-1096, 1078-1097, 1079-1098, 1080-1099, 1081-1100, 1082-1101, 1083-1102, 1084-1103, 1085-1104, 1086-1105, 1087-1106, 1088-1107, 1089-1108, 1090-1109, 1091-1110, 1092-1111, 1093-1112, 1094-1113, 1095-1114, 1096-1115, 1097-1116, 1098-1117, 1099-1118, 1100-1119, 1101-1120, 1102-1121, 1103-1122, 1104-1123, 1105-1124, 1106-1125, 1107-1126, 1108-1127, 1109-1128, 1110-1129, 1111-1130, 1112-1131, 1113-1132, 1114-1133, 1115-1134, 1116-1135, 1117-1136, 1118-1137, 1119-1138, 1120-1139, 1121-1140, 1122-1141, 1123-1142, 1124-1143, 1125-1144, 1126-1145, 1127-1146, 1128-1147, 1129-1148, 1130-1149, 1131-1150, 1132-1151, 1133-1152, 1134-1153, 1135-1154, 1136-1155, 1137-1156, 1138-1157, 1139-1158, 1140-1159, 1141-1160, 1142-1161, 1143-1162, 1144-1163, 1145-1164, 1146-1165, 1147-1166, 1148-1167, 1149-1168, 1150-1169, 1151-1170, 1152-1171, 1153-1172, 1154-1173, 1155-1174, 1156-1175, 1157-1176, 1158-1177, 1159-1178, 1160-1179, 1161-1180, 1162-1181, 1163-1182, 1164-1183, 1165-1184, 1166-1185, 1167-1186, 1168-1187, 1169-1188, 1170-1189, 1171-1190, 1172-1191, 1173-1192, 1174-1193, 1175-1194, 1176-1195, 1177-1196, 1178-1197, 1179-1198, 1180-1199, 1181-1200, 1182-1201, 1183-1202, 1184-1203, 1185-1204, 1186-1205, 1187-1206, 1188-1207, 1189-1208, 1190-1209, 1191-1210, 1192-1211, 1193-1212, 1194-1213, 1195-1214, 1196-1215, 1197-1216, 1198-1217, 1199-1218, 1200-1219, 1201-1220, 1202-1221, 1203-1222, 1204-1223, 1205-1224, 1206-1225, 1207-1226, 1208-1227, 1209-1228, 1210-1229, 1211-1230, 1212-1231, 1213-1232, 1214-1233, 1215-1234, 1216-1235, 1217-1236, 1218-1237, 1219-1238, 1220-1239, 1221-1240, 1222-1241, 1223-1242, 1224-1243, 1225-1244, 1226-1245, 1227-1246, 1228-1247, 1229-1248, 1230-1249, 1231-1250, 1232-1251, 1233-1252, 1234-1253, 1235-1254, 1236-1255, 1237-1256, 1238-1257, 1239-1258, 1240-1259, 1241-1260, 1242-1261, 1243-1262, 1244-1263, 1245-1264, 1246-1265, 1247-1266, 1248-1267, 1249-1268, 1250-1269, 1251-1270, 1252-1271, 1253-1272, 1254-1273, 1255-1274, 1256-1275, 1257-1276, 1258-1277, 1259-1278, 1260-1279, 1261-1280, 1262-1281, 1263-1282, 1264-1283, 1265-1284, 1266-1285, 1267-1286, 1268-1287, 1269-1288, 1270-1289, 1271-1290, 1272-1291, 1273-1292, 1274-1293, 1275-1294, 1276-1295, 1277-1296, 1278-1297, 1279-1298, 1280-1299, 1281-1300, 1282-1301, 1283-1302, 1284-1303, 1285-1304, 1286-1305, 1287-1306, 1288-1307, 1289-1308, 1290-1309, 1291-1310, 1292-1311, 1293-1312, 1294-1313, 1295-1314, 1296-1315, 1297-1316, 1298-1317, 1299-1318, 1300-1319, 1301-1320, 1302-1321, 1303-1322, 1304-1323, 1305-1324, 1306-1325, 1307-1326, 1308-1327, 1309-1328, 1310-1329, 1311-1330, 1312-1331, 1313-1332, 1314-1333, 1315-1334, 1316-1335, 1317-1336, 1318-1337, 1319-1338, 1320-1339, 1321-1340, 1322-1341, 1323-1342, 1324-1343, 1325-1344, 1326-1345, 1327-1346, 1328-1347, 1329-1348, 1330-1349, 1331-1350, 1332-1351, 1333-1352, 1334-1353, 1335-1354, 1336-1355, 1337-1356, 1338-1357, 1339-1358, 1340-1359, 1341-1360, 1342-1361, 1343-1362, 1344-1363, 1345-1364, 1346-1365, 1347-1366, 1348-1367, 1349-1368, 1350-1369, 1351-1370, 1352-1371, 1353-1372, 1354-1373, 1355-1374, 1356-1375, 1357-1376, 1358-1377, 1359-1378, 1360-1379, 1361-1380, 1362-1381, 1363-1382, 1364-1383, 1365-1384, 1366-1385, 1367-1386, 1368-1387, 1369-1388, 1370-1389, 1371-1390, 1372-1391, 1373-1392, 1374-1393, 1375-1394, 1376-1395, 1377-1396, 1378-1397, 1379-1398, 1380-1399, 1381-1400, 1382-1401, 1383-1402, 1384-1403, 1385-1404, 1386-1405, 1387-1406, 1388-1407, 1389-1408, 1390-1409, 1391-1410, 1392-1411, 1393-1412, 1394-1413, 1395-1414, 1396-1415, 1397-1416, 1398-1417, 1399-1418, 1400-1419, 1401-1420, 1402-1421, 1403-1422, 1404-1423, 1405-1424, 1406-1425, 1407-1426, 1408-1427, 1409-1428, 1410-1429, 1411-1430, 1412-1431, 1413-1432, 1414-1433, 1415-1434, 1416-1435, 1417-1436, 1418-1437, 1419-1438, 1420-1439, 1421-1440, 1422-1441, 1423-1442, 1424-1443, 1425-1444, 1426-1445, 1427-1446, 1428-1447, 1429-1448, 1430-1449, 1431-1450, 1432-1451, 1433-1452, 1434-1453, 1435-1454, 1436-1455, 1437-1456, 1438-1457, 1439-1458, 1440-1459, 1441-1460, 1442-1461, 1443-1462, 1444-1463, 1445-1464, 1446-1465, 1447-1466, 1448-1467, 1449-1468, 1450-1469, 1451-1470, 1452-1471, 1453-1472, 1454-1473, 1455-1474, 1456-1475, 1457-1476, 1458-1477, 1459-1478, 1460-1479, 1461-1480, 1462-1481, 1463-1482, 1464-1483, 1465-1484, 1466-1485, 1467-1486, 1468-1487, 1469-1488, 1470-1489, 1471-1490, 1472-1491, 1473-1492, 1474-1493, 1475-1494, 1476-1495, 1477-1496, 1478-1497, 1479-1498, 1480-1499, 1481-1500, 1482-1501, 1483-1502, 1484-1503, 1485-1504, 1486-1505, 1487-1506, 1488-1507, 1489-1508, 1490-1509, 1491-1510, 1492-1511, 1493-1512, 1494-1513, 1495-1514, 1496-1515, 1497-1516, 1498-1517, 1499-1518, 1500-1519, 1501-1520, 1502-1521, 1503-1522, 1504-1523, 1505-1524, 1506-1525, 1507-1526, 1508-1527, 1509-1528, 1510-1529, 1511-1530, 1512-1531, 1513-1532, 1514-1533, 1515-1534, 1516-1535, 1517-1536, 1518-1537, 1519-1538, 1520-1539, 1521-1540, 1522-1541, 1523-1542, 1524-1543, 1525-1544, 1526-1545, 1527-1546, 1528-1547, 1529-1548, 1530-1549, 1531-1550, 1532-1551, 1533-1552, 1534-1553, 1535-1554, 1536-1555, 1537-1556, 1538-1557, 1539-1558, 1540-1559, 1541-1560, 1542-1561, 1543-1562, 1544-1563, 1545-1564, 1546-1565, 1547-1566, 1548-1567, 1549-1568, 1550-1569, 1551-1570, 1552-1571, 1553-1572, 1554-1573, 1555-1574, 1556-1575, 1557-1576, 1558-1577, 1559-1578, 1560-1579, 1561-1580, 1562-1581, 1563-1582, 1564-1583, 1565-1584, 1566-1585, 1567-1586, 1568-1587, 1569-1588, 1570-1589, 1571-1590, 1572-1591, 1573-1592, 1574-1593, 1575-1594, 1576-1595, 1577-1596, 1578-1597, 1579-1598, 1580-1599, 1581-1600, 1582-1601, 1583-1602, 1584-1603, 1585-1604, 1586-1605, 1587-1606, 1588-1607, 1589-1608, 1590-1609, 1591-1610, 1592-1611, 1593-1612, 1594-1613, 1595-1614, 1596-1615, 1597-1616, 1598-1617, 1599-1618, 1600-1619, 1601-1620, 1602-1621, 1603-1622, 1604-1623, 1605-1624, 1606-1625, 1607-1626, 1608-1627, 1609-1628, 1610-1629, 1611-1630, 1612-1631, 1613-1632, 1614-1633, 1615-1634, 1616-1635, 1617-1636, 1618-1637, 1619-1638, 1620-1639, 1621-1640, 1622-1641, 1623-1642, 1624-1643, 1625-1644, 1626-1645, 1627-1646, 1628-1647, 1629-1648, 1630-1649, 1631-1650, 1632-1651, 1633-1652, 1634-1653, 1635-1654, 1636-1655, 1637-1656, 1638-1657, 1639-1658, 1640-1659, 1641-1660, 1642-1661, 1643-1662, 1644-1663, 1645-1664, 1646-1665, 1647-1666, 1648-1667, 1649-1668, 1650-1669, 1651-1670, 1652-1671, 1653-1672, 1654-1673, 1655-1674, 1656-1675, 1657-1676, 1658-1677, 1659-1678, 1660-1679, 1661-1680, 1662-1681, 1663-1682, 1664-1683, 1665-1684, 1666-1685, 1667-1686, 1668-1687, 1669-1688, 1670-1689, 1671-1690, 1672-1691, 1673-1692, 1674-1693, 1675-1694, 1676-1695, 1677-1696, 1678-1697, 1679-1698, 1680-1699, 1681-1700, 1682-1701, 1683-1702, 1684-1703, 1685-1704, 1686-1705, 1687-1706, 1688-1707, 1689-1708, 1690-1709, 1691-1710, 1692-1711, 1693-1712, 1694-1713, 1695-1714, 1696-1715, 1697-1716, 1698-1717, 1699-1718, 1700-1719, 1701-1720, 1702-1721, 1703-1722, 1704-1723, 1705-1724, 1706-1725, 1707-1726, 1708-1727, 1709-1728, 1710-1729, 1711-1730, 1712-1731, 1713-1732, 1714-1733, 1715-1734, 1716-1735, 1717-1736, 1718-1737, 1719-1738, 1720-1739, 1721-1740, 1722-1741, 1723-1742, 1724-1743, 1725-1744, 1726-1745, 1727-1746, 1728-1747, 1729-1748, 1730-1749, 1731-1750, 1732-1751, 1733-1752, 1734-1753, 1735-1754, 1736-1755, 1737-1756, 1738-1757, 1739-1758, 1740-1759, 1741-1760, 1742-1761, 1743-1762, 1744-1763, 1745-1764, 1746-1765, 1747-1766, 1748-1767, 1749-1768, 1750-1769, 1751-1770, 1752-1771, 1753-1772, 1754-1773, 1755-1774, 1756-1775, 1757-1776, 1758-1777, 1759-1778, 1760-1779, 1761-1780, 1762-1781, 1763-1782, 1764-1783, 1765-1784, 1766-1785, 1767-1786, 1768-1787, 1769-1788, 1770-1789, 1771-1790, 1772-1791, 1773-1792, 1774-1793, 1775-1794, 1776-1795, 1777-1796, 1778-1797, 1779-1798, 1780-1799, 1781-1800, 1782-1801, 1783-1802, 1784-1803, 1785-1804, 1786-1805, 1787-1806, 1788-1807, 1789-1808, 1790-1809, 1791-1810, 1792-1811, 1793-1812, 1794-1813, 1795-1814, 1796-1815, 1797-1816, 1798-1817, 1799-1818, 1800-1819, 1801-1820, 1802-1821, 1803-1822, 1804-1823, 1805-1824, 1806-1825, 1807-1826, 1808-1827, 1809-1828, 1810-1829, 1811-1830, 1812-1831, 1813-1832, 1814-1833, 1815-1834, 1816-1835, 1817-1836, 1818-1837, 1819-1838, 1820-1839, 1821-1840, 1822-1841, 1823-1842, 1824-1843, 1825-1844, 1826-1845, 1827-1846, 1828-1847, 1829-1848, 1830-1849, 1831-1850, 1832-1851, 1833-1852, 1834-1853, 1835-1854, 1836-1855, 1837-1856, 1838-1857, 1839-1858, 1840-1859, 1841-1860, 1842-1861, 1843-1862, 1844-1863, 1845-1864, 1846-1865, 1847-1866, 1848-1867, 1849-1868, 1850-1869, 1851-1870, 1852-1871, 1853-1872, 1854-1873, 1855-1874, 1856-1875, 1857-1876, 1858-1877, 1859-1878, 1860-1879, 1861-1880, 1862-1881, 1863-1882, 1864-1883, 1865-1884, 1866-1885, 1867-1886, 1868-1887, 1869-1888, 1870-1889, 1871-1890, 1872-1891, 1873-1892, 1874-1893, 1875-1894, 1876-1895, 1877-1896, 1878-1897, 1879-1898, 1880-1899, 1881-1900, 1882-1901, 1883-1902, 1884-1903, 1885-1904, 1886-1905, 1887-1906, 1888-1907, 1889-1908, 1890-1909, 1891-1910, 1892-1911, 1893-1912, 1894-1913, 1895-1914, 1896-1915, 1897-1916, 1898-1917, 1899-1918, 1900-1919, 1901-1920, 1902-1921, 1903-1922, 1904-1923, 1905-1924, 1906-1925, 1907-1926, 1908-1927, 1909-1928, 1910-1929, 1911-1930, 1912-1931, 1913-1932, 1914-1933, 1915-1934, 1916-1935, 1917-1936, 1918-1937, 1919-1938, 1920-1939, 1921-1940, 1922-1941, 1923-1942, 1924-1943, 1925-1944, 1926-1945, 1927-1946, 1928-1947, 1929-1948, 1930-1949, 1931-1950, 1932-1951, 1933-1952, 1934-1953, 1935-1954, 1936-1955, 1937-1956, 1938-1957, 1939-1958, 1940-1959, 1941-1960, 1942-1961, 1943-1962, 1944-1963, 1945-1964, 1946-1965, 1947-1966, 1948-1967, 1949-1968, 1950-1969, 1951-1970, 1952-1971, 1953-1972, 1954-1973, 1955-1974, 1956-1975, 1957-1976, 1958-1977, 1959-1978, 1960-1979, 1961-1980, 1962-1981, 1963-1982, 1964-1983, 1965-1984, 1966-1985, 1967-1986, 1968-1987, 1969-1988, 1970-1989, 1971-1990, 1972-1991, 1973-1992, 1974-1993, 1975-1994, 1976-1995, 1977-1996, 1978-1997, 1979-1998, 1980-1999, 1981-2000, 1982-2001, 1983-2002, 1984-2003, 1985-2004, 1986-2005, 1987-2006, 1988-2007, 1989-2008, 1990-2009, 1991-2010, 1992-2011, 1993-2012, 1994-2013, 1995-2014, 1996-2015, 1997-2016, 1998-2017, 1999-2018, 2000-2019, 2001-2020, 2002-2021, 2003-2022, 2004-2023, 2005-2024, 2006-2025, 2007-2026, 2008-2027, 2009-2028, 2010-2029, 2011-2030, 2012-2031, 2013-2032, 2014-2033, 2015-2034, 2016-2035, 2017-2036, 2018-2037, 2019-2038, 2020-2039, 2021-2040, 2022-2041, 2023-2042, 2024-2043, 2025-2044, 2026-2045, 2027-2046, 2028-2047, 2029-2048, 2030-2049, 2031-2050, 2032-2051, 2033-2052, 2034-2053, 2035-2054, 2036-2055, 2037-2056, 2038-2057, 2039-2058, 2040-2059, 2041-2060, 2042-2061, 2043-2062, 2044-2063, 2045-2064, 2046-2065, 2047-2066, 2048-2067, 2049-2068, 2050-2069, 2051-2070, 2052-2071, 2053-2072, 2054-2073, 2055-2074, 2056-2075, 2057-2076, 2058-2077, 2059-2078, 2060-2079, 2061-2080, 2062-2081, 2063-2082, 2064-2083, 2065-2084, 2066-2085, 2067-2086, 2068-2087, 2069-2088, 2070-2089, 2071-2090, 2072-2091, 2073-2092, 2074-2093, 2075-2094, 2076-2095, 2077-2096, 2078-2097, 2079-2098, 2080-2099, 2081-2100, 2082-2101, 2083-2102, 2084-2103, 2085-2104, 2086-2105, 2087-2106, 2088-2107, 2089-2108, 2090-2109, 2091-2110, 2092-2111, 2093-2112, 2094-2113, 2095-2114, 2096-2115, 2097-2116, 2098-2117, 2099-2118, 2100-2119, 2101-2120, 2102-2121, 2103-2122, 2104-2123, 2105-2124, 2106-2125, 2107-2126, 2108-2127, 2109-2128, 2110-2129, 2111-2130, 2112-2131, 2113-2132, 2114-2133, 2115-2134, 2116-2135, 2117-2136, 2118-2137, 2119-2138, 2120-2139, 2121-2140, 2122-2141, 2123-2142, 2124-2143, 2125-2144, 2126-2145, 2127-2146, 2128-2147, 2129-2148, 2130-2149, 2131-2150, 2132-2151, 2133-2152, 2134-2153, 2135-2154, 2136-2155, 2137-2156, 2138-2157, 2139-2158, 2140-2159, 2141-2160, 2142-2161, 2143-2162, 2144-2163, 2145-2164, 2146-2165, 2147-2166, 2148-2167, 2149-2168, 2150-2169, 2151-2170, 2152-2171, 2153-2172, 2154-2173, 2155-2174, 2156-2175, 2157-2176, 2158-2177, 2159-2178, 2160-2179, 2161-2180, 2162-2181, 2163-2182, 2164-2183, 2165-2184, 2166-2185, 2167-2186, 2168-2187, 2169-2188, 2170-2189, 2171-2190, 2172-2191, 2173-2192, 2174-2193, 2175-2194, 2176-2195, 2177-2196, 2178-2197, 2179-2198, 2180-2199, 2181-2200, 2182-2201, 2183-2202, 2184-2203, 2185-2204, 2186-2205, 2187-2206, 2188-2207, 2189-2208, 2190-2209, 2191-2210, 2192-2211, 2193-2212, 2194-2213, 2195-2214, 2196-2215, 2197-2216, 2198-2217, 2199-2218, 2200-2219, 2201-2220, 2202-2221, 2203-2222, 2204-2223, 2205-2224, 2206-2225, 2207-2226, 2208-2227, 2209-2228, 2210-2229, 2211-2230, 2212-2231, 2213-2232, 2214-2233, 2215-2234, 2216-2235, 2217-2236, 2218-2237, 2219-2238, 2220-2239, 2221-2240, 2222-2241, 2223-2242, 2224-2243, 2225-2244, 2226-2245, 2227-2246, 2228-2247, 2229-2248, 2230-2249, 2231-2250, 2232-2251, 2233-2252, 2234-2253, 2235-2254, 2236-2255, 2237-2256, 2238-2257, 2239-2258, 2240-2259, 2241-2260, 2242-2261,
2243-2262, 2244-2263, 2245-2264, 2246-2265, 2247-2266,
2248-2267, 2249-2268, 2250-2269, 2251-2270, 2252-2271,
2253-2272, 2254-2273, 2255-2274, 2256-2275, 2257-2276,
2258-2277, 2259-2278, 2260-2279, 2261-2280, 2262-2281,
2263-2282, 2264-2283, 2265-2284, 2266-2285, 2267-2286,
2268-2287, 2269-2288, 2270-2289, 2271-2290, 2272-2291,
2273-2292, 2274-2293, 2275-2294, 2276-2295, 2277-2296,
2278-2297, 2279-2298, 2280-2299, 2281-2300, 2282-2301,
2283-2302, 2284-2303, 2285-2304, 2286-2305, 2287-2306,
2288-2307, 2289-2308, 2290-2309, 2291-2310, 2292-2311,
2293-2312, 2294-2313, 2295-2314, 2296-2315, 2297-2316,
2298-2317, 2299-2318, 2300-2319, 2301-2320, 2302-2321,
2303-2322, 2304-2323, 2305-2324, 2306-2325, 2307-2326,
2308-2327, 2309-2328, 2310-2329, 2311-2330, 2312-2331,
2313-2332, 2314-2333, 2315-2334, 2316-2335, 2317-2336,
2318-2337, 2319-2338, 2320-2339, 2321-2340, 2322-2341,
2323-2342, 2324-2343, 2325-2344, 2326-2345, 2327-2346,
2328-2347, 2329-2348, 2330-2349, 2331-2350, 2332-2351,
2333-2352, 2334-2353, 2335-2354, 2336-2355, 2337-2356,
2338-2357, 2339-2358, 2340-2359, 2341-2360, 2342-2361,
2343-2362, 2344-2363, 2345-2364, 2346-2365, 2347-2366,
2348-2367, 2349-2368, 2350-2369, 2351-2370, 2352-2371,
2353-2372, 2354-2373, 2355-2374, 2356-2375, 2357-2376,
2358-2377, 2359-2378, 2360-2379, 2361-2380, 2362-2381,
2363-2382, 2364-2383, 2365-2384, 2366-2385, 2367-2386,
2368-2387, 2369-2388, 2370-2389, 2371-2390, 2372-2391,
2373-2392, 2374-2393, 2375-2394, 2376-2395, 2377-2396,
2378-2397, 2379-2398, 2380-2399, 2381-2400, 2382-2401,
2383-2402, 2384-2403, 2385-2404, 2386-2405, 2387-2406,
2388-2407, 2389-2408, 2390-2409, 2391-2410, 2392-2411,
2393-2412, 2394-2413, 2395-2414, 2396-2415, 2397-2416,
2398-2417, 2399-2418, 2400-2419, 2401-2420, 2402-2421,
2403-2422, 2404-2423, 2405-2424, 2406-2425, 2407-2426,
2408-2427, 2409-2428, 2410-2429, 2411-2430, 2412-2431,
2413-2432, 2414-2433, 2415-2434, 2416-2435, 2417-2436,
2418-2437, 2419-2438, 2420-2439, 2421-2440, 2422-2441,
2423-2442, 2424-2443, 2425-2444, 2426-2445, 2427-2446,
2428-2447, 2429-2448, 2430-2449, 2431-2450, 2432-2451,
2433-2452, 2434-2453, 2435-2454, 2436-2455, 2437-2456,
2438-2457, 2439-2458, 2440-2459, 2441-2460, 2442-2461,
2443-2462, 2444-2463, 2445-2464, 2446-2465, 2447-2466,
2448-2467, 2449-2468, 2450-2469, 2451-2470, 2452-2471,
2453-2472, 2454-2473, 2455-2474, 2456-2475, 2457-2476,
2458-2477, 2459-2478, 2460-2479, 2461-2480, 2462-2481,
2463-2482, 2464-2483, 2465-2484, 2466-2485, 2467-2486,
2468-2487, 2469-2488, 2470-2489, 2471-2490, 2472-2491,
2473-2492, 2474-2493, 2475-2494, 2476-2495, 2477-2496,
2478-2497, 2479-2498, 2480-2499, 2481-2500, 2482-2501,
2483-2502, 2484-2503, 2485-2504, 2486-2505, 2487-2506,
2488-2507, 2489-2508, 2490-2509, 2491-2510, 2492-2511,
2493-2512, 2494-2513, 2495-2514, 2496-2515, 2497-2516,
2498-2517, 2499-2518, 2500-2519, 2501-2520, 2502-2521,
2503-2522, 2504-2523, 2505-2524, 2506-2525, 2507-2526,
2508-2527, 2509-2528, 2510-2529, 2511-2530, 2512-2531,
2513-2532, 2514-2533, 2515-2534, 2516-2535, 2517-2536,
2518-2537, 2519-2538, 2520-2539, 2521-2540, 2522-2541,
2523-2542, 2524-2543, 2525-2544, 2526-2545, 2527-2546,
2528-2547, 2529-2548, 2530-2549, 2531-2550, 2532-2551,
2533-2552, 2534-2553, 2535-2554, 2536-2555, 2537-2556,
2538-2557, 2539-2558, 2540-2559, 2541-2560, 2542-2561,
2543-2562, 2544-2563, 2545-2564, 2546-2565, 2547-2566,
2548-2567, 2549-2568, 2550-2569, 2551-2570, 2552-2571,
2553-2572, 2554-2573, 2555-2574, 2556-2575, 2557-2576,
2558-2577, 2559-2578, 2560-2579, 2561-2580, 2562-2581,
2563-2582, 2564-2583, 2565-2584, 2566-2585, 2567-2586,
2568-2587, 2569-2588, 2570-2589, 2571-2590, 2572-2591,
2573-2592, 2574-2593, 2575-2594, 2576-2595, 2577-2596,
2578-2597, 2579-2598, 2580-2599, 2581-2600, 2582-2601,
2583-2602, 2584-2603, 2585-2604, 2586-2605, 2587-2606,
2588-2607, 2589-2608, 2590-2609, 2591-2610, 2592-2611,
2593-2612, 2594-2613, 2595-2614, 2596-2615, 2597-2616,
2598-2617, 2599-2618, 2600-2619, 2601-2620, 2602-2621,
2603-2622, 2604-2623, 2605-2624, 2606-2625, 2607-2626,
2608-2627, 2609-2628, 2610-2629, 2611-2630, 2612-2631,
2613-2632, 2614-2633, 2615-2634, 2616-2635, 2617-2636,
2618-2637, 2619-2638, 2620-2639, 2621-2640, 2622-2641,
2623-2642, 2624-2643, 2625-2644, 2626-2645, 2627-2646,
2628-2647, 2629-2648, 2630-2649, 2631-2650, 2632-2651,
2633-2652, 2634-2653, 2635-2654, 2636-2655, 2637-2656,
2638-2657, 2639-2658, 2640-2659, 2641-2660, 2642-2661,
2643-2662, 2644-2663, 2645-2664, 2646-2665, 2647-2666,
2648-2667, 2649-2668, 2650-2669, 2651-2670, 2652-2671,
2653-2672, 2654-2673, 2655-2674, 2656-2675, 2657-2676,
2658-2677, 2659-2678, 2660-2679, 2661-2680, 2662-2681,
2663-2682, 2664-2683, 2665-2684, 2666-2685, 2667-2686,
2668-2687, 2669-2688, 2670-2689, 2671-2690, 2672-2691,
2673-2692, 2674-2693, 2675-2694, 2676-2695, 2677-2696,
2678-2697, 2679-2698, 2680-2699, 2681-2700, 2682-2701,
2683-2702, 2684-2703, 2685-2704, 2686-2705, 2687-2706,
2688-2707, 2689-2708, 2690-2709, 2691-2710, 2692-2711,
2693-2712, 2694-2713, 2695-2714, 2696-2715, 2697-2716,
2698-2717, 2699-2718, 2700-2719, 2701-2720, 2702-2721,
2703-2722, 2704-2723, 2705-2724, 2706-2725, 2707-2726,
2708-2727, 2709-2728, 2710-2729, 2711-2730, 2712-2731,
2713-2732, 2714-2733, 2715-2734, 2716-2735, 2717-2736,
2718-2737, 2719-2738, 2720-2739, 2721-2740, 2722-2741,
2723-2742, 2724-2743, 2725-2744, 2726-2745, 2727-2746,
2728-2747, 2729-2748, 2730-2749, 2731-2750, 2732-2751,
2733-2752, 2734-2753, 2735-2754, 2736-2755, 2737-2756,
2738-2757, 2739-2758, 2740-2759, 2741-2760, 2742-2761,
2743-2762, 2744-2763, 2745-2764, 2746-2765, 2747-2766,
2748-2767, 2749-2768, 2750-2769, 2751-2770, 2752-2771,
2753-2772, 2754-2773, 2755-2774, 2756-2775, 2757-2776,
2758-2777, 2759-2778, 2760-2779, 2761-2780, 2762-2781,
2763-2782, 2764-2783, 2765-2784, 2766-2785, 2767-2786,
2768-2787, 2769-2788, 2770-2789, 2771-2790, 2772-2791,
2773-2792, 2774-2793, 2775-2794, 2776-2795, 2777-2796,
2778-2797, 2779-2798, 2780-2799, 2781-2800, 2782-2801,
2783-2802, 2784-2803, 2785-2804, 2786-2805, 2787-2806,
2788-2807, 2789-2808, 2790-2809, 2791-2810, 2792-2811,
2793-2812, 2794-2813, 2795-2814, 2796-2815, 2797-2816,
2798-2817, 2799-2818, 2800-2819, 2801-2820, 2802-2821,
2803-2822, 2804-2823, 2805-2824, 2806-2825, 2807-2826,
2808-2827, 2809-2828, 2810-2829, 2811-2830, 2812-2831,
2813-2832, 2814-2833, 2815-2834, 2816-2835, 2817-2836,
2818-2837, 2819-2838, 2820-2839, 2821-2840, 2822-2841,
2823-2842, 2824-2843, 2825-2844, 2826-2845, 2827-2846,
2828-2847, 2829-2848, 2830-2849, 2831-2850, 2832-2851,
2833-2852, 2834-2853, 2835-2854, 2836-2855, 2837-2856,
2838-2857, 2839-2858, 2840-2859, 2841-2860, 2842-2861,
2843-2862, 2844-2863, 2845-2864, 2846-2865, 2847-2866,
2848-2867, 2849-2868, 2850-2869, 2851-2870, 2852-2871,
2853-2872, 2854-2873, 2855-2874, 2856-2875, 2857-2876,
2858-2877, 2859-2878, 2860-2879, 2861-2880, 2862-2881,
2863-2882, 2864-2883, 2865-2884, 2866-2885, 2867-2886,
2868-2887, 2869-2888, 2870-2889, 2871-2890, 2872-2891,
2873-2892, 2874-2893, 2875-2894, 2876-2895, 2877-2896,
2878-2897, 2879-2898, 2880-2899, 2881-2900, 2882-2901,
2883-2902, 2884-2903, 2885-2904, 2886-2905, 2887-2906,
2888-2907, 2889-2908, 2890-2909, 2891-2910, 2892-2911,
2893-2912, 2894-2913, 2895-2914, 2896-2915, 2897-2916,
2898-2917, 2899-2918, 2900-2919, 2901-2920, 2902-2921,
2903-2922, 2904-2923, 2905-2924, 2906-2925, 2907-2926, 2908-2927, 2909-2928, 2910-2929, 2911-2930, 2912-2931, 2913-2932, 2914-2933, 2915-2934, 2916-2935, 2917-2936, 2918-2937, 2919-2938, 2920-2939, 2921-2940, 2922-2941, 2923-2942, 2924-2943, 2925-2944, 2926-2945, 2927-2946, 2928-2947, 2929-2948, 2930-2949, 2931-2950, 2932-2951, 2933-2952, 2934-2953, 2935-2954, 2936-2955, 2937-2956, 2938-2957, 2939-2958, 2940-2959, 2941-2960, 2942-2961, 2943-2962, 2944-2963, 2945-2964, 2946-2965, 2947-2966, 2948-2967, 2949-2968, 2950-2969, 2951-2970, 2952-2971, 2953-2972, 2954-2973, 2955-2974, 2956-2975, 2957-2976, 2958-2977, 2959-2978, 2960-2979, 2961-2980, 2962-2981, 2963-2982, 2964-2983, 2965-2984, 2966-2985, 2967-2986, 2968-2987, 2969-2988, 2970-2989, 2971-2990, 2972-2991, 2973-2992, 2974-2993, 2975-2994, 2976-2995, 2977-2996, 2978-2997, 2979-2998, 2980-2999, 2981-3000, 2982-3001, 2983-3002, 2984-3003, 2985-3004, 2986-3005, 2987-3006, 2988-3007, 2989-3008, 2990-3009, 2991-3010, 2992-3011, 2993-3012, 2994-3013, 2995-3014, 2996-3015, 2997-3016, 2998-3017, 2999-3018, 3000-3019, 3001-3020, 3002-3021, 3003-3022, 3004-3023, 3005-3024, 3006-3025, 3007-3026, 3008-3027, 3009-3028, 3010-3029, 3011-3030, 3012-3031, 3013-3032, 3014-3033, 3015-3034, 3016-3035, 3017-3036, 3018-3037, 3019-3038, 3020-3039, 3021-3040, 3022-3041, 3023-3042, 3024-3043, 3025-3044, 3026-3045, 3027-3046, 3028-3047, 3029-3048, 3030-3049, 3031-3050, 3032-3051, 3033-3052, 3034-3053, 3035-3054, 3036-3055, 3037-3056, 3038-3057, 3039-3058, 3040-3059, 3041-3060, 3042-3061, 3043-3062, 3044-3063, 3045-3064, 3046-3065, 3047-3066, 3048-3067, 3049-3068, 3050-3069, 3051-3070, 3052-3071, 3053-3072, 3054-3073, 3055-3074, 3056-3075, 3057-3076, 3058-3077, 3059-3078, 3060-3079, 3061-3080, 3062-3081, 3063-3082, 3064-3083, 3065-3084, 3066-3085, 3067-3086, 3068-3087, 3069-3088, 3070-3089, 3071-3090, 3072-3091, 3073-3092, 3074-3093, 3075-3094, 3076-3095, 3077-3096, 3078-3097, 3079-3098, 3080-3099, 3081-3100, 3082-3101, 3083-3102, 3084-3103, 3085-3104, 3086-3105, 3087-3106, 3088-3107, 3089-3108, 3090-3109, 3091-3110, 3092-3111, 3093-3112, 3094-3113, 3095-3114, 3096-3115, 3097-3116, 3098-3117, 3099-3118, 3100-3119, 3101-3120, 3102-3121, 3103-3122, 3104-3123, 3105-3124, 3106-3125, 3107-3126, 3108-3127, 3109-3128, 3110-3129, 3111-3130, 3112-3131, 3113-3132, 3114-3133, 3115-3134, 3116-3135, 3117-3136, 3118-3137, 3119-3138, 3120-3139, 3121-3140, 3122-3141, 3123-3142, 3124-3143, 3125-3144, 3126-3145, 3127-3146, 3128-3147, 3129-3148, 3130-3149, 3131-3150, 3132-3151, 3133-3152, 3134-3153, 3135-3154, 3136-3155, 3137-3156, 3138-3157, 3139-3158, 3140-3159, 3141-3160, 3142-3161, 3143-3162, 3144-3163, 3145-3164, 3146-3165, 3147-3166, 3148-3167, 3149-3168, 3150-3169, 3151-3170, 3152-3171, 3153-3172, 3154-3173, 3155-3174, 3156-3175, 3157-3176, 3158-3177, 3159-3178, 3160-3179, 3161-3180, 3162-3181, 3163-3182, 3164-3183, 3165-3184, 3166-3185, 3167-3186, 3168-3187, 3169-3188, 3170-3189, 3171-3190, 3172-3191, 3173-3192, 3174-3193, 3175-3194, 3176-3195, 3177-3196, 3178-3197, 3179-3198, 3180-3199, 3181-3200, 3182-3201, 3183-3202, 3184-3203, 3185-3204, 3186-3205, 3187-3206, 3188-3207, 3189-3208, 3190-3209, 3191-3210, 3192-3211, 3193-3212, 3194-3213, 3195-3214, 3196-3215, 3197-3216, 3198-3217, 3199-3218, 3200-3219, 3201-3220, 3202-3221, 3203-3222, 3204-3223, 3205-3224, 3206-3225, 3207-3226, 3208-3227, 3209-3228, 3210-3229, 3211-3230, 3212-3231, 3213-3232, 3214-3233, 3215-3234, 3216-3235, 3217-3236, 3218-3237, 3219-3238, 3220-3239, 3221-3240, 3222-3241, 3223-3242, 3224-3243, 3225-3244, 3226-3245, 3227-3246, 3228-3247, 3229-3248, 3230-3249, 3231-3250, 3232-3251, 3233-3252, 3234-3253, 3235-3254, 3236-3255, 3237-3256, 3238-3257, 3239-3258, 3240-3259, 3241-3260, 3242-3261, 3243-3262, 3244-3263, 3245-3264, 3246-3265, 3247-3266, 3248-3267, 3249-3268, 3250-3269, 3251-3270, 3252-3271, 3253-3272, 3254-3273, 3255-3274, 3256-3275, 3257-3276, 3258-3277, 3259-3278, 3260-3279, 3261-3280, 3262-3281, 3263-3282, 3264-3283, 3265-3284, 3266-3285, 3267-3286, 3268-3287, 3269-3288, 3270-3289, 3271-3290, 3272-3291, 3273-3292, 3274-3293, 3275-3294, 3276-3295, 3277-3296, 3278-3297, 3279-3298, 3280-3299, 3281-3300, 3282-3301, 3283-3302, 3284-3303, 3285-3304, 3286-3305, 3287-3306, 3288-3307, 3289-3308, 3290-3309, 3291-3310, 3292-3311, 3293-3312, 3294-3313, 3295-3314, 3296-3315, 3297-3316, 3298-3317, 3299-3318, 3300-3319, 3301-3320, 3302-3321, 3303-3322, 3304-3323, 3305-3324, 3306-3325, 3307-3326, 3308-3327, 3309-3328, 3310-3329, 3311-3330, 3312-3331, 3313-3332, 3314-3333, 3315-3334, 3316-3335, 3317-3336, 3318-3337, 3319-3338, 3320-3339, 3321-3340, 3322-3341, 3323-3342, 3324-3343, 3325-3344, 3326-3345, 3327-3346, 3328-3347, 3329-3348, 3330-3349, 3331-3350, 3332-3351, 3333-3352, 3334-3353, 3335-3354, 3336-3355, 3337-3356, 3338-3357, 3339-3358, 3340-3359, 3341-3360, 3342-3361, 3343-3362, 3344-3363, 3345-3364, 3346-3365, 3347-3366, 3348-3367, 3349-3368, 3350-3369, 3351-3370, 3352-3371, 3353-3372, 3354-3373, 3355-3374, 3356-3375, 3357-3376, 3358-3377, 3359-3378, 3360-3379, 3361-3380, 3362-3381, 3363-3382, 3364-3383, 3365-3384, 3366-3385, 3367-3386, 3368-3387, 3369-3388, 3370-3389, 3371-3390, 3372-3391, 3373-3392, 3374-3393, 3375-3394, 3376-3395, 3377-3396, 3378-3397, 3379-3398, 3380-3399, 3381-3400, 3382-3401, 3383-3402, 3384-3403, 3385-3404, 3386-3405, 3387-3406, 3388-3407, 3389-3408, 3390-3409, 3391-3410, 3392-3411, 3393-3412, 3394-3413, 3395-3414, 3396-3415, 3397-3416, 3398-3417, 3399-3418, 3400-3419, 3401-3420, 3402-3421, 3403-3422, 3404-3423, 3405-3424, 3406-3425, 3407-3426, 3408-3427, 3409-3428, 3410-3429, 3411-3430, 3412-3431, 3413-3432, 3414-3433, 3415-3434, 3416-3435, 3417-3436, 3418-3437, 3419-3438, 3420-3439, 3421-3440, 3422-3441, 3423-3442, 3424-3443, 3425-3444, 3426-3445, 3427-3446, 3428-3447, 3429-3448, 3430-3449, 3431-3450, 3432-3451, 3433-3452, 3434-3453, 3435-3454, 3436-3455, 3437-3456, 3438-3457, 3439-3458, 3440-3459, 3441-3460, 3442-3461, 3443-3462, 3444-3463, 3445-3464, 3446-3465, 3447-3466, 3448-3467, 3449-3468, 3450-3469, 3451-3470, 3452-3471, 3453-3472, 3454-3473, 3455-3474, 3456-3475, 3457-3476, 3458-3477, 3459-3478, 3460-3479, 3461-3480, 3462-3481, 3463-3482, 3464-3483, 3465-3484, 3466-3485, 3467-3486, 3468-3487, 3469-3488, 3470-3489, 3471-3490, 3472-3491, 3473-3492, 3474-3493, 3475-3494, 3476-3495, 3477-3496, 3478-3497, 3479-3498, 3480-3499, 3481-3500, 3482-3501, 3483-3502, 3484-3503, 3485-3504, 3486-3505, 3487-3506, 3488-3507, 3489-3508, 3490-3509, 3491-3510, 3492-3511, 3493-3512, 3494-3513, 3495-3514, 3496-3515, 3497-3516, 3498-3517, 3499-3518, 3500-3519, 3501-3520, 3502-3521, 3503-3522, 3504-3523, 3505-3524, 3506-3525, 3507-3526, 3508-3527, 3509-3528, 3510-3529, 3511-3530, 3512-3531, 3513-3532, 3514-3533, 3515-3534, 3516-3535, 3517-3536, 3518-3537, 3519-3538, 3520-3539, 3521-3540, 3522-3541, 3523-3542, 3524-3543, 3525-3544, 3526-3545, 3527-3546, 3528-3547, 3529-3548, 3530-3549, 3531-3550, 3532-3551, 3533-3552, 3534-3553, 3535-3554, 3536-3555, 3537-3556, 3538-3557, 3539-3558, 3540-3559, 3541-3560, 3542-3561, 3543-3562, 3544-3563, 3545-3564, 3546-3565, 3547-3566, 3548-3567, 3549-3568, 3550-3569, 3551-3570, 3552-3571, 3553-3572, 3554-3573, 3555-3574, 3556-3575, 3557-3576, 3558-3577, 3559-3578, 3560-3579, 3561-3580, 3562-3581, 3563-3582, 3564-3583, 3565-3584, 3566-3585, 3567-3586, 3568-3587, 3569-3588, 3570-3589, 3571-3590, 3572-3591, 3573-3592, 3574-3593, 3575-3594, 3576-3595, 3577-3596, 3578-3597, 3579-3598, 3580-3599, 3581-3600, 3582-3601, 3583-3602, 3584-3603, 3585-3604, 3586-3605, 3587-3606, 3588-3607, 3589-3608, 3590-3609, 3591-3610, 3592-3611, 3593-3612, 3594-3613, 3595-3614, 3596-3615, 3597-3616, 3598-3617, 3599-3618, 3600-3619, 3601-3620, 3602-3621, 3603-3622, 3604-3623, 3605-3624, 3606-3625, 3607-3626, 3608-3627, 3609-3628, 3610-3629, 3611-3630, 3612-3631, 3613-3632, 3614-3633, 3615-3634, 3616-3635, 3617-3636, 3618-3637, 3619-3638, 3620-3639, 3621-3640, 3622-3641, 3623-3642, 3624-3643, 3625-3644, 3626-3645, 3627-3646, 3628-3647, 3629-3648, 3630-3649, 3631-3650, 3632-3651, 3633-3652, 3634-3653, 3635-3654, 3636-3655, 3637-3656, 3638-3657, 3639-3658, 3640-3659, 3641-3660, 3642-3661, 3643-3662, 3644-3663, 3645-3664, 3646-3665, 3647-3666, 3648-3667, 3649-3668, 3650-3669, 3651-3670, 3652-3671, 3653-3672, 3654-3673, 3655-3674, 3656-3675, 3657-3676, 3658-3677, 3659-3678, 3660-3679, 3661-3680, 3662-3681, 3663-3682, 3664-3683, 3665-3684, 3666-3685, 3667-3686, 3668-3687, 3669-3688, 3670-3689, 3671-3690, 3672-3691, 3673-3692, 3674-3693, 3675-3694, 3676-3695, 3677-3696, 3678-3697, 3679-3698, 3680-3699, 3681-3700, 3682-3701, 3683-3702, 3684-3703, 3685-3704, 3686-3705, 3687-3706, 3688-3707, 3689-3708, 3690-3709, 3691-3710, 3692-3711, 3693-3712, 3694-3713, 3695-3714, 3696-3715, 3697-3716, 3698-3717, 3699-3718, 3700-3719, 3701-3720, 3702-3721, 3703-3722, 3704-3723, 3705-3724, 3706-3725, 3707-3726, 3708-3727, 3709-3728, 3710-3729, 3711-3730, 3712-3731, 3713-3732, 3714-3733, 3715-3734, 3716-3735, 3717-3736, 3718-3737, 3719-3738, 3720-3739, 3721-3740, 3722-3741, 3723-3742, 3724-3743, 3725-3744, 3726-3745, 3727-3746, 3728-3747, 3729-3748, 3730-3749, 3731-3750, 3732-3751, 3733-3752, 3734-3753, 3735-3754, 3736-3755, 3737-3756, 3738-3757, 3739-3758, 3740-3759, 3741-3760, 3742-3761, 3743-3762, 3744-3763, 3745-3764, 3746-3765, 3747-3766, 3748-3767, 3749-3768, 3750-3769, 3751-3770, 3752-3771, 3753-3772, 3754-3773, 3755-3774, 3756-3775, 3757-3776, 3758-3777, 3759-3778, 3760-3779, 3761-3780, 3762-3781, 3763-3782, 3764-3783, 3765-3784, 3766-3785, 3767-3786, 3768-3787, 3769-3788, 3770-3789, 3771-3790, 3772-3791, 3773-3792, 3774-3793, 3775-3794, 3776-3795, 3777-3796, 3778-3797, 3779-3798, 3780-3799, 3781-3800, 3782-3801, 3783-3802, 3784-3803, 3785-3804, 3786-3805, 3787-3806, 3788-3807, 3789-3808, 3790-3809, 3791-3810, 3792-3811, 3793-3812, 3794-3813, 3795-3814, 3796-3815, 3797-3816, 3798-3817, 3799-3818, 3800-3819, 3801-3820, 3802-3821, 3803-3822, 3804-3823, 3805-3824, 3806-3825, 3807-3826, 3808-3827, 3809-3828, 3810-3829, 3811-3830, 3812-3831, 3813-3832, 3814-3833, 3815-3834, 3816-3835, 3817-3836, 3818-3837, 3819-3838, 3820-3839, 3821-3840, 3822-3841, 3823-3842, 3824-3843, 3825-3844, 3826-3845, 3827-3846, 3828-3847, 3829-3848, 3830-3849, 3831-3850, 3832-3851, 3833-3852, 3834-3853, 3835-3854, 3836-3855, 3837-3856, 3838-3857, 3839-3858, 3840-3859, 3841-3860, 3842-3861, 3843-3862, 3844-3863, 3845-3864, 3846-3865, 3847-3866, 3848-3867, 3849-3868, 3850-3869, 3851-3870, 3852-3871, 3853-3872, 3854-3873, 3855-3874, 3856-3875, 3857-3876, 3858-3877, 3859-3878, 3860-3879, 3861-3880, 3862-3881, 3863-3882, 3864-3883, 3865-3884, 3866-3885, 3867-3886, 3868-3887, 3869-3888, 3870-3889, 3871-3890, 3872-3891, 3873-3892, 3874-3893, 3875-3894, 3876-3895, 3877-3896, 3878-3897, 3879-3898, 3880-3899, 3881-3900, 3882-3901, 3883-3902, 3884-3903, 3885-3904, 3886-3905, 3887-3906, 3888-3907, 3889-3908, 3890-3909, 3891-3910, 3892-3911, 3893-3912, 3894-3913, 3895-3914, 3896-3915, 3897-3916, 3898-3917, 3899-3918, 3900-3919, 3901-3920, 3902-3921, 3903-3922, 3904-3923, 3905-3924, 3906-3925, 3907-3926, 3908-3927, 3909-3928, 3910-3929, 3911-3930, 3912-3931, 3913-3932, 3914-3933, 3915-3934, 3916-3935, 3917-3936, 3918-3937, 3919-3938, 3920-3939, 3921-3940, 3922-3941, 3923-3942, 3924-3943, 3925-3944, 3926-3945, 3927-3946, 3928-3947, 3929-3948, 3930-3949, 3931-3950, 3932-3951, 3933-3952, 3934-3953, 3935-3954, 3936-3955, 3937-3956, 3938-3957, 3939-3958, 3940-3959, 3941-3960, 3942-3961, 3943-3962, 3944-3963, 3945-3964, 3946-3965, 3947-3966, 3948-3967, 3949-3968, 3950-3969, 3951-3970, 3952-3971, 3953-3972, 3954-3973, 3955-3974, 3956-3975, 3957-3976, 3958-3977, 3959-3978, 3960-3979, 3961-3980, 3962-3981, 3963-3982, 3964-3983, 3965-3984, 3966-3985, 3967-3986, 3968-3987, 3969-3988, 3970-3989, 3971-3990, 3972-3991, 3973-3992, 3974-3993, 3975-3994, 3976-3995, 3977-3996, 3978-3997, 3979-3998, and 3980-3999.

Examples of 25-mer oligonucleotides include the following oligonucleotides, indicated by polynucleotide positions with reference to SEQ ID NO: 1: 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, 26-50, 27-51, 28-52, 29-53, 30-54, 31-55, 32-56, 33-57, 34-58, 35-59, 36-60, 37-61, 38-62, 39-63, 40-64, 41-65, 42-66, 43-67, 44-68, 45-69, 46-70, 47-71, 48-72, 49-73, 50-74, 51-75, 52-76, 53-77, 54-78, 55-79, 56-80, 57-81, 58-82, 59-83, 60-84, 61-85, 62-86, 63-87, 64-88, 65-89, 66-90, 67-91, 68-92, 69-93, 70-94, 71-95, 72-96, 73-97, 74-98, 75-99, 76-100, 77-101, 78-102, 79-103, 80-104, 81-105, 82-106, 83-107, 84-108, 85-109, 86-110, 87-111, 88-112, 89-113, 90-114, 91-115, 92-116, 93-117, 94-118, 95-119, 96-120, 97-121, 98-122, 99-123, 100-124, 101-125, 102-126, 103-127, 104-128, 105-129, 106-130, 107-131, 108-132, 109-133, 110-134, 111-135, 112-136, 113-137, 114-138, 115-139, 116-140, 117-141, 118-142, 119-143, 120-144, 121-145, 122-146, 123-147, 124-148, 125-149, 126-150, 127-151, 128-152, 129-153, 130-154, 131-155, 132-156, 133-157, 134-158, 135-159, 136-160, 137-161, 138-162, 139-163, 140-164, 141-165, 142-166, 143-167, 144-168, 145-169, 146-170, 147-171, 148-172, 149-173, 150-174, 151-175, 152-176, 153-177, 154-178, 155-179, 156-180, 157-181, 158-182, 159-183, 160-184, 161-185, 162-186, 163-187, 164-188, 165-189, 166-190, 167-191, 168-192, 169-193, 170-194, 171-195, 172-196, 173-197, 174-198, 175-199, 176-200, 177-201, 178-202, 179-203, 180-204, 181-205, 182-206, 183-207, 184-208, 185-209, 186-210, 187-211, 188-212, 189-213, 190-214, 191-215, 192-216, 193-217, 194-218, 195-219, 196-220, 197-221, 198-222, 199-223, 200-224, 201-225, 202-226, 203-227, 204-228, 205-229, 206-230, 207-231, 208-232, 209-233, 210-234, 211-235, 212-236, 213-237, 214-238, 215-239, 216-240, 217-241, 218-242, 219-243, 220-244, 221-245, 222-246, 223-247, 224-248, 225-249, 226-250, 227-251, 228-252, 229-253, 230-254, 231-255, 232-256, 233-257, 234-258, 235-259, 236-260, 237-261, 238-262, 239-263, 240-264, 241-265, 242-266, 243-267, 244-268, 245-269, 246-270, 247-271, 248-272, 249-273, 250-274, 251-275, 252-276, 253-277, 254-278, 255-279, 256-280, 257-281, 258-282, 259-283, 260-284, 261-285, 262-286, 263-287, 264-288, 265-289, 266-290, 267-291, 268-292, 269-293, 270-294, 271-295, 272-296, 273-297, 274-298, 275-299, 276-300, 277-301, 278-302, 279-303, 280-304, 281-305, 282-306, 283-307, 284-308, 285-309, 286-310, 287-311, 288-312, 289-313, 290-314, 291-315, 292-316, 293-317, 294-318, 295-319, 296-320, 297-321, 298-322, 299-323, 300-324, 301-325, 302-326, 303-327, 304-328, 305-329, 306-330, 307-331, 308-332, 309-333, 310-334, 311-335, 312-336, 313-337, 314-338, 315-339, 316-340, 317-341, 318-342, 319-343, 320-344, 321-345, 322-346, 323-347, 324-348, 325-349, 326-350, 327-351, 328-352, 329-353, 330-354, 331-355, 332-356, 333-357, 334-358, 335-359, 336-360, 337-361, 338-362, 339-363, 340-364, 341-365, 342-366, 343-367, 344-368, 345-369, 346-370, 347-371, 348-372, 349-373, 350-374, 351-375, 352-376, 353-377, 354-378, 355-379, 356-380, 357-381, 358-382, 359-383, 360-384, 361-385, 362-386, 363-387, 364-388, 365-389, 366-390, 367-391, 368-392, 369-393, 370-394, 371-395, 372-396, 373-397, 374-398, 375-399, 376-400, 377-401, 378-402, 379-403, 380-404, 381-405, 382-406, 383-407, 384-408, 385-409, 386-410, 387-411, 388-412, 389-413, 390-414, 391-415, 392-416, 393-417, 394-418, 395-419, 396-420, 397-421, 398-422, 399-423, 400-424, 401-425, 402-426, 403-427, 404-428, 405-429, 406-430, 407-431, 408-432, 409-433, 410-434, 411-435, 412-436, 413-437, 414-438, 415-439, 416-440, 417-441, 418-442, 419-443, 420-444, 421-445, 422-446, 423-447, 424-448, 425-449, 426-450, 427-451, 428-452, 429-453, 430-454, 431-455, 432-456, 433-457, 434-458, 435-459, 436-460, 437-461, 438-462, 439-463, 440-464, 441-465, 442-466, 443-467, 444-468, 445-469, 446-470, 447-471, 448-472, 449-473, 450-474, 451-475, 452-476, 453-477, 454-478, 455-479, 456-480, 457-481, 458-482, 459-483, 460-484, 461-485, 462-486, 463-487, 464-488, 465-489, 466-490, 467-491, 468-492, 469-493, 470-494, 471-495, 472-496, 473-497, 474-498, 475-499, 476-500, 477-501, 478-502, 479-503, 480-504, 481-505, 482-506, 483-507, 484-508, 485-509, 486-510, 487-511, 488-512, 489-513, 490-514, 491-515, 492-516, 493-517, 494-518, 495-519, 496-520, 497-521, 498-522, 499-523, 500-524, 501-525, 502-526, 503-527, 504-528, 505-529, 506-530, 507-531, 508-532, 509-533, 510-534, 511-535, 512-536, 513-537, 514-538, 515-539, 516-540, 517-541, 518-542, 519-543, 520-544, 521-545, 522-546, 523-547, 524-548, 525-549, 526-550, 527-551, 528-552, 529-553, 530-554, 531-555, 532-556, 533-557, 534-558, 535-559, 536-560, 537-561, 538-562, 539-563, 540-564, 541-565, 542-566, 543-567, 544-568, 545-569, 546-570, 547-571, 548-572, 549-573, 550-574, 551-575, 552-576, 553-577, 554-578, 555-579, 556-580, 557-581, 558-582, 559-583, 560-584, 561-585, 562-586, 563-587, 564-588, 565-589, 566-590, 567-591, 568-592, 569-593, 570-594, 571-595, 572-596, 573-597, 574-598, 575-599, 576-600, 577-601, 578-602, 579-603, 580-604, 581-605, 582-606, 583-607, 584-608, 585-609, 586-610, 587-611, 588-612, 589-613, 590-614, 591-615, 592-616, 593-617, 594-618, 595-619, 596-620, 597-621, 598-622, 599-623, 600-624, 601-625, 602-626, 603-627, 604-628, 605-629, 606-630, 607-631, 608-632, 609-633, 610-634, 611-635, 612-636, 613-637, 614-638, 615-639, 616-640, 617-641, 618-642, 619-643, 620-644, 621-645, 622-646, 623-647, 624-648, 625-649, 626-650, 627-651, 628-652, 629-653, 630-654, 631-655, 632-656, 633-657, 634-658, 635-659, 636-660, 637-661, 638-662, 639-663, 640-664, 641-665, 642-666, 643-667, 644-668, 645-669, 646-670, 647-671, 648-672, 649-673, 650-674, 651-675, 652-676, 653-677, 654-678, 655-679, 656-680, 657-681, 658-682, 659-683, 660-684, 661-685, 662-686, 663-687, 664-688, 665-689, 666-690, 667-691, 668-692, 669-693, 670-694, 671-695, 672-696, 673-697, 674-698, 675-699, 676-700, 677-701, 678-702, 679-703, 680-704, 681-705, 682-706, 683-707, 684-708, 685-709, 686-710, 687-711, 688-712, 689-713, 690-714, 691-715, 692-716, 693-717, 694-718, 695-719, 696-720, 697-721, 698-722, 699-723, 700-724, 701-725, 702-726, 703-727, 704-728, 705-729, 706-730, 707-731, 708-732, 709-733, 710-734, 711-735, 712-736, 713-737, 714-738, 715-739, 716-740, 717-741, 718-742, 719-743, 720-744, 721-745, 722-746, 723-747, 724-748, 725-749, 726-750, 727-751, 728-752, 729-753, 730-754, 731-755, 732-756, 733-757, 734-758, 735-759, 736-760, 737-761, 738-762, 739-763, 740-764, 741-765, 742-766, 743-767, 744-768, 745-769, 746-770, 747-771, 748-772, 749-773, 750-774, 751-775, 752-776, 753-777, 754-778, 755-779, 756-780, 757-781, 758-782, 759-783, 760-784, 761-785, 762-786, 763-787, 764-788, 765-789, 766-790, 767-791, 768-792, 769-793, 770-794, 771-795, 772-796, 773-797, 774-798, 775-799, 776-800, 777-801, 778-802, 779-803, 780-804, 781-805, 782-806, 783-807, 784-808, 785-809, 786-810, 787-811, 788-812, 789-813, 790-814, 791-815, 792-816, 793-817, 794-818, 795-819, 796-820, 797-821, 798-822, 799-823, 800-824, 801-825, 802-826, 803-827, 804-828, 805-829, 806-830, 807-831, 808-832, 809-833, 810-834, 811-835, 812-836, 813-837, 814-838, 815-839, 816-840, 817-841, 818-842, 819-843, 820-844, 821-845, 822-846, 823-847, 824-848, 825-849, 826-850, 827-851, 828-852, 829-853, 830-854, 831-855, 832-856, 833-857, 834-858, 835-859, 836-860, 837-861, 838-862, 839-863, 840-864, 841-865, 842-866, 843-867, 844-868, 845-869, 846-870, 847-871, 848-872, 849-873, 850-874, 851-875, 852-876, 853-877, 854-878, 855-879, 856-880, 857-881, 858-882, 859-883, 860-884, 861-885, 862-886, 863-887, 864-888, 865-889, 866-890, 867-891, 868-892, 869-893, 870-894, 871-895, 872-896, 873-897, 874-898, 875-899, 876-900, 877-901, 878-902, 879-903, 880-904, 881-905, 882-906, 883-907, 884-908, 885-909, 886-910, 887-911, 888-912, 889-913, 890-914, 891-915, 892-916, 893-917, 894-918, 895-919, 896-920, 897-921, 898-922, 899-923, 900-924, 901-925, 902-926, 903-927, 904-928, 905-929, 906-930, 907-931, 908-932, 909-933, 910-934, 911-935, 912-936, 913-937, 914-938, 915-939, 916-940, 917-941, 918-942, 919-943, 920-944, 921-945, 922-946, 923-947, 924-948, 925-949, 926-950, 927-951, 928-952, 929-953, 930-954, 931-955, 932-956, 933-957, 934-958, 935-959, 936-960, 937-961, 938-962, 939-963, 940-964, 941-965, 942-966, 943-967, 944-968, 945-969, 946-970, 947-971, 948-972, 949-973, 950-974, 951-975, 952-976, 953-977, 954-978, 955-979, 956-980, 957-981, 958-982, 959-983, 960-984, 961-985, 962-986, 963-987, 964-988, 965-989, 966-990, 967-991, 968-992, 969-993, 970-994, 971-995, 972-996, 973-997, 974-998, 975-999, 976-1000, 977-1001, 978-1002, 979-1003, 980-1004, 981-1005, 982-1006, 983-1007, 984-1008, 985-1009, 986-1010, 987-1011, 988-1012, 989-1013, 990-1014, 991-1015, 992-1016, 993-1017, 994-1018, 995-1019, 996-1020, 997-1021, 998-1022, 999-1023, 1000-1024, 1001-1025, 1002-1026, 1003-1027, 1004-1028, 1005-1029, 1006-1030, 1007-1031, 1008-1032, 1009-1033, 1010-1034, 1011-1035, 1012-1036, 1013-1037, 1014-1038, 1015-1039, 1016-1040, 1017-1041, 1018-1042, 1019-1043, 1020-1044, 1021-1045, 1022-1046, 1023-1047, 1024-1048, 1025-1049, 1026-1050, 1027-1051, 1028-1052, 1029-1053, 1030-1054, 1031-1055, 1032-1056, 1033-1057, 1034-1058, 1035-1059, 1036-1060, 1037-1061, 1038-1062, 1039-1063, 1040-1064, 1041-1065, 1042-1066, 1043-1067, 1044-1068, 1045-1069, 1046-1070, 1047-1071, 1048-1072, 1049-1073, 1050-1074, 1051-1075, 1052-1076, 1053-1077, 1054-1078, 1055-1079, 1056-1080, 1057-1081, 1058-1082, 1059-1083, 1060-1084, 1061-1085, 1062-1086, 1063-1087, 1064-1088, 1065-1089, 1066-1090, 1067-1091, 1068-1092, 1069-1093, 1070-1094, 1071-1095, 1072-1096, 1073-1097, 1074-1098, 1075-1099, 1076-1100, 1077-1101, 1078-1102, 1079-1103, 1080-1104, 1081-1105, 1082-1106, 1083-1107, 1084-1108, 1085-1109, 1086-1110, 1087-1111, 1088-1112, 1089-1113, 1090-1114, 1091-1115, 1092-1116, 1093-1117, 1094-1118, 1095-1119, 1096-1120, 1097-1121, 1098-1122, 1099-1123, 1100-1124, 1101-1125, 1102-1126, 1103-1127, 1104-1128, 1105-1129, 1106-1130, 1107-1131, 1108-1132, 1109-1133, 1110-1134, 1111-1135,
1112-1136, 1113-1137, 1114-1138, 1115-1139, 1116-1140,
1117-1141, 1118-1142, 1119-1143, 1120-1144, 1121-1145,
1122-1146, 1123-1147, 1124-1148, 1125-1149, 1126-1150,
1127-1151, 1128-1152, 1129-1153, 1130-1154, 1131-1155,
1132-1156, 1133-1157, 1134-1158, 1135-1159, 1136-1160,
1137-1161, 1138-1162, 1139-1163, 1140-1164, 1141-1165,
1142-1166, 1143-1167, 1144-1168, 1145-1169, 1146-1170,
1147-1171, 1148-1172, 1149-1173, 1150-1174, 1151-1175,
1152-1176, 1153-1177, 1154-1178, 1155-1179, 1156-1180,
1157-1181, 1158-1182, 1159-1183, 1160-1184, 1161-1185,
1162-1186, 1163-1187, 1164-1188, 1165-1189, 1166-1190,
1167-1191, 1168-1192, 1169-1193, 1170-1194, 1171-1195,
1172-1196, 1173-1197, 1174-1198, 1175-1199, 1176-1200,
1177-1201, 1178-1202, 1179-1203, 1180-1204, 1181-1205,
1182-1206, 1183-1207, 1184-1208, 1185-1209, 1186-1210,
1187-1211, 1188-1212, 1189-1213, 1190-1214, 1191-1215,
1192-1216, 1193-1217, 1194-1218, 1195-1219, 1196-1220,
1197-1221, 1198-1222, 1199-1223, 1200-1224, 1201-1225,
1202-1226, 1203-1227, 1204-1228, 1205-1229, 1206-1230,
1207-1231, 1208-1232, 1209-1233, 1210-1234, 1211-1235,
1212-1236, 1213-1237, 1214-1238, 1215-1239, 1216-1240,
1217-1241, 1218-1242, 1219-1243, 1220-1244, 1221-1245,
1222-1246, 1223-1247, 1224-1248, 1225-1249, 1226-1250,
1227-1251, 1228-1252, 1229-1253, 1230-1254, 1231-1255,
1232-1256, 1233-1257, 1234-1258, 1235-1259, 1236-1260,
1237-1261, 1238-1262, 1239-1263, 1240-1264, 1241-1265,
1242-1266, 1243-1267, 1244-1268, 1245-1269, 1246-1270,
1247-1271, 1248-1272, 1249-1273, 1250-1274, 1251-1275,
1252-1276, 1253-1277, 1254-1278, 1255-1279, 1256-1280,
1257-1281, 1258-1282, 1259-1283, 1260-1284, 1261-1285,
1262-1286, 1263-1287, 1264-1288, 1265-1289, 1266-1290,
1267-1291, 1268-1292, 1269-1293, 1270-1294, 1271-1295,
1272-1296, 1273-1297, 1274-1298, 1275-1299, 1276-1300,
1277-1301, 1278-1302, 1279-1303, 1280-1304, 1281-1305,
1282-1306, 1283-1307, 1284-1308, 1285-1309, 1286-1310,
1287-1311, 1288-1312, 1289-1313, 1290-1314, 1291-1315,
1292-1316, 1293-1317, 1294-1318, 1295-1319, 1296-1320,
1297-1321, 1298-1322, 1299-1323, 1300-1324, 1301-1325,
1302-1326, 1303-1327, 1304-1328, 1305-1329, 1306-1330,
1307-1331, 1308-1332, 1309-1333, 1310-1334, 1311-1335,
1312-1336, 1313-1337, 1314-1338, 1315-1339, 1316-1340,
1317-1341, 1318-1342, 1319-1343, 1320-1344, 1321-1345,
1322-1346, 1323-1347, 1324-1348, 1325-1349, 1326-1350,
1327-1351, 1328-1352, 1329-1353, 1330-1354, 1331-1355,
1332-1356, 1333-1357, 1334-1358, 1335-1359, 1336-1360,
1337-1361, 1338-1362, 1339-1363, 1340-1364, 1341-1365,
1342-1366, 1343-1367, 1344-1368, 1345-1369, 1346-1370,
1347-1371, 1348-1372, 1349-1373, 1350-1374, 1351-1375,
1352-1376, 1353-1377, 1354-1378, 1355-1379, 1356-1380,
1357-1381, 1358-1382, 1359-1383, 1360-1384, 1361-1385,
1362-1386, 1363-1387, 1364-1388, 1365-1389, 1366-1390,
1367-1391, 1368-1392, 1369-1393, 1370-1394, 1371-1395,
1372-1396, 1373-1397, 1374-1398, 1375-1399, 1376-1400,
1377-1401, 1378-1402, 1379-1403, 1380-1404, 1381-1405,
1382-1406, 1383-1407, 1384-1408, 1385-1409, 1386-1410,
1387-1411, 1388-1412, 1389-1413, 1390-1414, 1391-1415,
1392-1416, 1393-1417, 1394-1418, 1395-1419, 1396-1420,
1397-1421, 1398-1422, 1399-1423, 1400-1424, 1401-1425,
1402-1426, 1403-1427, 1404-1428, 1405-1429, 1406-1430,
1407-1431, 1408-1432, 1409-1433, 1410-1434, 1411-1435,
1412-1436, 1413-1437, 1414-1438, 1415-1439, 1416-1440,
1417-1441, 1418-1442, 1419-1443, 1420-1444, 1421-1445,
1422-1446, 1423-1447, 1424-1448, 1425-1449, 1426-1450,
1427-1451, 1428-1452, 1429-1453, 1430-1454, 1431-1455,
1432-1456, 1433-1457, 1434-1458, 1435-1459, 1436-1460,
1437-1461, 1438-1462, 1439-1463, 1440-1464, 1441-1465,
1442-1466, 1443-1467, 1444-1468, 1445-1469, 1446-1470,
1447-1471, 1448-1472, 1449-1473, 1450-1474, 1451-1475,
1452-1476, 1453-1477, 1454-1478, 1455-1479, 1456-1480,
1457-1481, 1458-1482, 1459-1483, 1460-1484, 1461-1485,
1462-1486, 1463-1487, 1464-1488, 1465-1489, 1466-1490,
1467-1491, 1468-1492, 1469-1493, 1470-1494, 1471-1495,
1472-1496, 1473-1497, 1474-1498, 1475-1499, 1476-1500,
1477-1501, 1478-1502, 1479-1503, 1480-1504, 1481-1505,
1482-1506, 1483-1507, 1484-1508, 1485-1509, 1486-1510,
1487-1511, 1488-1512, 1489-1513, 1490-1514, 1491-1515,
1492-1516, 1493-1517, 1494-1518, 1495-1519, 1496-1520,
1497-1521, 1498-1522, 1499-1523, 1500-1524, 1501-1525,
1502-1526, 1503-1527, 1504-1528, 1505-1529, 1506-1530,
1507-1531, 1508-1532, 1509-1533, 1510-1534, 1511-1535,
1512-1536, 1513-1537, 1514-1538, 1515-1539, 1516-1540,
1517-1541, 1518-1542, 1519-1543, 1520-1544, 1521-1545,
1522-1546, 1523-1547, 1524-1548, 1525-1549, 1526-1550,
1527-1551, 1528-1552, 1529-1553, 1530-1554, 1531-1555,
1532-1556, 1533-1557, 1534-1558, 1535-1559, 1536-1560,
1537-1561, 1538-1562, 1539-1563, 1540-1564, 1541-1565,
1542-1566, 1543-1567, 1544-1568, 1545-1569, 1546-1570,
1547-1571, 1548-1572, 1549-1573, 1550-1574, 1551-1575,
1552-1576, 1553-1577, 1554-1578, 1555-1579, 1556-1580,
1557-1581, 1558-1582, 1559-1583, 1560-1584, 1561-1585,
1562-1586, 1563-1587, 1564-1588, 1565-1589, 1566-1590,
1567-1591, 1568-1592, 1569-1593, 1570-1594, 1571-1595,
1572-1596, 1573-1597, 1574-1598, 1575-1599, 1576-1600,
1577-1601, 1578-1602, 1579-1603, 1580-1604, 1581-1605,
1582-1606, 1583-1607, 1584-1608, 1585-1609, 1586-1610,
1587-1611, 1588-1612, 1589-1613, 1590-1614, 1591-1615,
1592-1616, 1593-1617, 1594-1618, 1595-1619, 1596-1620,
1597-1621, 1598-1622, 1599-1623, 1600-1624, 1601-1625,
1602-1626, 1603-1627, 1604-1628, 1605-1629, 1606-1630,
1607-1631, 1608-1632, 1609-1633, 1610-1634, 1611-1635,
1612-1636, 1613-1637, 1614-1638, 1615-1639, 1616-1640,
1617-1641, 1618-1642, 1619-1643, 1620-1644, 1621-1645,
1622-1646, 1623-1647, 1624-1648, 1625-1649, 1626-1650,
1627-1651, 1628-1652, 1629-1653, 1630-1654, 1631-1655,
1632-1656, 1633-1657, 1634-1658, 1635-1659, 1636-1660,
1637-1661, 1638-1662, 1639-1663, 1640-1664, 1641-1665,
1642-1666, 1643-1667, 1644-1668, 1645-1669, 1646-1670,
1647-1671, 1648-1672, 1649-1673, 1650-1674, 1651-1675,
1652-1676, 1653-1677, 1654-1678, 1655-1679, 1656-1680,
1657-1681, 1658-1682, 1659-1683, 1660-1684, 1661-1685,
1662-1686, 1663-1687, 1664-1688, 1665-1689, 1666-1690,
1667-1691, 1668-1692, 1669-1693, 1670-1694, 1671-1695,
1672-1696, 1673-1697, 1674-1698, 1675-1699, 1676-1700,
1677-1701, 1678-1702, 1679-1703, 1680-1704, 1681-1705,
1682-1706, 1683-1707, 1684-1708, 1685-1709, 1686-1710,
1687-1711, 1688-1712, 1689-1713, 1690-1714, 1691-1715,
1692-1716, 1693-1717, 1694-1718, 1695-1719, 1696-1720,
1697-1721, 1698-1722, 1699-1723, 1700-1724, 1701-1725,
1702-1726, 1703-1727, 1704-1728, 1705-1729, 1706-1730,
1707-1731, 1708-1732, 1709-1733, 1710-1734, 1711-1735,
1712-1736, 1713-1737, 1714-1738, 1715-1739, 1716-1740,
1717-1741, 1718-1742, 1719-1743, 1720-1744, 1721-1745,
1722-1746, 1723-1747, 1724-1748, 1725-1749, 1726-1750,
1727-1751, 1728-1752, 1729-1753, 1730-1754, 1731-1755,
1732-1756, 1733-1757, 1734-1758, 1735-1759, 1736-1760,
1737-1761, 1738-1762, 1739-1763, 1740-1764, 1741-1765,
1742-1766, 1743-1767, 1744-1768, 1745-1769, 1746-1770,
1747-1771, 1748-1772, 1749-1773, 1750-1774, 1751-1775,
1752-1776, 1753-1777, 1754-1778, 1755-1779, 1756-1780,
1757-1781, 1758-1782, 1759-1783, 1760-1784, 1761-1785,
1762-1786, 1763-1787, 1764-1788, 1765-1789, 1766-1790,
1767-1791, 1768-1792, 1769-1793, 1770-1794, 1771-1795,
1772-1796, 1773-1797, 1774-1798, 1775-1799, 1776-1800, 1777-1801, 1778-1802, 1779-1803, 1780-1804, 1781-1805, 1782-1806, 1783-1807, 1784-1808, 1785-1809, 1786-1810, 1787-1811, 1788-1812, 1789-1813, 1790-1814, 1791-1815, 1792-1816, 1793-1817, 1794-1818, 1795-1819, 1796-1820, 1797-1821, 1798-1822, 1799-1823, 1800-1824, 1801-1825, 1802-1826, 1803-1827, 1804-1828, 1805-1829, 1806-1830, 1807-1831, 1808-1832, 1809-1833, 1810-1834, 1811-1835, 1812-1836, 1813-1837, 1814-1838, 1815-1839, 1816-1840, 1817-1841, 1818-1842, 1819-1843, 1820-1844, 1821-1845, 1822-1846, 1823-1847, 1824-1848, 1825-1849, 1826-1850, 1827-1851, 1828-1852, 1829-1853, 1830-1854, 1831-1855, 1832-1856, 1833-1857, 1834-1858, 1835-1859, 1836-1860, 1837-1861, 1838-1862, 1839-1863, 1840-1864, 1841-1865, 1842-1866, 1843-1867, 1844-1868, 1845-1869, 1846-1870, 1847-1871, 1848-1872, 1849-1873, 1850-1874, 1851-1875, 1852-1876, 1853-1877, 1854-1878, 1855-1879, 1856-1880, 1857-1881, 1858-1882, 1859-1883, 1860-1884, 1861-1885, 1862-1886, 1863-1887, 1864-1888, 1865-1889, 1866-1890, 1867-1891, 1868-1892, 1869-1893, 1870-1894, 1871-1895, 1872-1896, 1873-1897, 1874-1898, 1875-1899, 1876-1900, 1877-1901, 1878-1902, 1879-1903, 1880-1904, 1881-1905, 1882-1906, 1883-1907, 1884-1908, 1885-1909, 1886-1910, 1887-1911, 1888-1912, 1889-1913, 1890-1914, 1891-1915, 1892-1916, 1893-1917, 1894-1918, 1895-1919, 1896-1920, 1897-1921, 1898-1922, 1899-1923, 1900-1924, 1901-1925, 1902-1926, 1903-1927, 1904-1928, 1905-1929, 1906-1930, 1907-1931, 1908-1932, 1909-1933, 1910-1934, 1911-1935, 1912-1936, 1913-1937, 1914-1938, 1915-1939, 1916-1940, 1917-1941, 1918-1942, 1919-1943, 1920-1944, 1921-1945, 1922-1946, 1923-1947, 1924-1948, 1925-1949, 1926-1950, 1927-1951, 1928-1952, 1929-1953, 1930-1954, 1931-1955, 1932-1956, 1933-1957, 1934-1958, 1935-1959, 1936-1960, 1937-1961, 1938-1962, 1939-1963, 1940-1964, 1941-1965, 1942-1966, 1943-1967, 1944-1968, 1945-1969, 1946-1970, 1947-1971, 1948-1972, 1949-1973, 1950-1974, 1951-1975, 1952-1976, 1953-1977, 1954-1978, 1955-1979, 1956-1980, 1957-1981, 1958-1982, 1959-1983, 1960-1984, 1961-1985, 1962-1986, 1963-1987, 1964-1988, 1965-1989, 1966-1990, 1967-1991, 1968-1992, 1969-1993, 1970-1994, 1971-1995, 1972-1996, 1973-1997, 1974-1998, 1975-1999, 1976-2000, 1977-2001, 1978-2002, 1979-2003, 1980-2004, 1981-2005, 1982-2006, 1983-2007, 1984-2008, 1985-2009, 1986-2010, 1987-2011, 1988-2012, 1989-2013, 1990-2014, 1991-2015, 1992-2016, 1993-2017, 1994-2018, 1995-2019, 1996-2020, 1997-2021, 1998-2022, 1999-2023, 2000-2024, 2001-2025, 2002-2026, 2003-2027, 2004-2028, 2005-2029, 2006-2030, 2007-2031, 2008-2032, 2009-2033, 2010-2034, 2011-2035, 2012-2036, 2013-2037, 2014-2038, 2015-2039, 2016-2040, 2017-2041, 2018-2042, 2019-2043, 2020-2044, 2021-2045, 2022-2046, 2023-2047, 2024-2048, 2025-2049, 2026-2050, 2027-2051, 2028-2052, 2029-2053, 2030-2054, 2031-2055, 2032-2056, 2033-2057, 2034-2058, 2035-2059, 2036-2060, 2037-2061, 2038-2062, 2039-2063, 2040-2064, 2041-2065, 2042-2066, 2043-2067, 2044-2068, 2045-2069, 2046-2070, 2047-2071, 2048-2072, 2049-2073, 2050-2074, 2051-2075, 2052-2076, 2053-2077, 2054-2078, 2055-2079, 2056-2080, 2057-2081, 2058-2082, 2059-2083, 2060-2084, 2061-2085, 2062-2086, 2063-2087, 2064-2088, 2065-2089, 2066-2090, 2067-2091, 2068-2092, 2069-2093, 2070-2094, 2071-2095, 2072-2096, 2073-2097, 2074-2098, 2075-2099, 2076-2100, 2077-2101, 2078-2102, 2079-2103, 2080-2104, 2081-2105, 2082-2106, 2083-2107, 2084-2108, 2085-2109, 2086-2110, 2087-2111, 2088-2112, 2089-2113, 2090-2114, 2091-2115, 2092-2116, 2093-2117, 2094-2118, 2095-2119, 2096-2120, 2097-2121, 2098-2122, 2099-2123, 2100-2124, 2101-2125, 2102-2126, 2103-2127, 2104-2128, 2105-2129, 2106-2130, 2107-2131, 2108-2132, 2109-2133, 2110-2134, 2111-2135, 2112-2136, 2113-2137, 2114-2138, 2115-2139, 2116-2140, 2117-2141, 2118-2142, 2119-2143, 2120-2144, 2121-2145, 2122-2146, 2123-2147, 2124-2148, 2125-2149, 2126-2150, 2127-2151, 2128-2152, 2129-2153, 2130-2154, 2131-2155, 2132-2156, 2133-2157, 2134-2158, 2135-2159, 2136-2160, 2137-2161, 2138-2162, 2139-2163, 2140-2164, 2141-2165, 2142-2166, 2143-2167, 2144-2168, 2145-2169, 2146-2170, 2147-2171, 2148-2172, 2149-2173, 2150-2174, 2151-2175, 2152-2176, 2153-2177, 2154-2178, 2155-2179, 2156-2180, 2157-2181, 2158-2182, 2159-2183, 2160-2184, 2161-2185, 2162-2186, 2163-2187, 2164-2188, 2165-2189, 2166-2190, 2167-2191, 2168-2192, 2169-2193, 2170-2194, 2171-2195, 2172-2196, 2173-2197, 2174-2198, 2175-2199, 2176-2200, 2177-2201, 2178-2202, 2179-2203, 2180-2204, 2181-2205, 2182-2206, 2183-2207, 2184-2208, 2185-2209, 2186-2210, 2187-2211, 2188-2212, 2189-2213, 2190-2214, 2191-2215, 2192-2216, 2193-2217, 2194-2218, 2195-2219, 2196-2220, 2197-2221, 2198-2222, 2199-2223, 2200-2224, 2201-2225, 2202-2226, 2203-2227, 2204-2228, 2205-2229, 2206-2230, 2207-2231, 2208-2232, 2209-2233, 2210-2234, 2211-2235, 2212-2236, 2213-2237, 2214-2238, 2215-2239, 2216-2240, 2217-2241, 2218-2242, 2219-2243, 2220-2244, 2221-2245, 2222-2246, 2223-2247, 2224-2248, 2225-2249, 2226-2250, 2227-2251, 2228-2252, 2229-2253, 2230-2254, 2231-2255, 2232-2256, 2233-2257, 2234-2258, 2235-2259, 2236-2260, 2237-2261, 2238-2262, 2239-2263, 2240-2264, 2241-2265, 2242-2266, 2243-2267, 2244-2268, 2245-2269, 2246-2270, 2247-2271, 2248-2272, 2249-2273, 2250-2274, 2251-2275, 2252-2276, 2253-2277, 2254-2278, 2255-2279, 2256-2280, 2257-2281, 2258-2282, 2259-2283, 2260-2284, 2261-2285, 2262-2286, 2263-2287, 2264-2288, 2265-2289, 2266-2290, 2267-2291, 2268-2292, 2269-2293, 2270-2294, 2271-2295, 2272-2296, 2273-2297, 2274-2298, 2275-2299, 2276-2300, 2277-2301, 2278-2302, 2279-2303, 2280-2304, 2281-2305, 2282-2306, 2283-2307, 2284-2308, 2285-2309, 2286-2310, 2287-2311, 2288-2312, 2289-2313, 2290-2314, 2291-2315, 2292-2316, 2293-2317, 2294-2318, 2295-2319, 2296-2320, 2297-2321, 2298-2322, 2299-2323, 2300-2324, 2301-2325, 2302-2326, 2303-2327, 2304-2328, 2305-2329, 2306-2330, 2307-2331, 2308-2332, 2309-2333, 2310-2334, 2311-2335, 2312-2336, 2313-2337, 2314-2338, 2315-2339, 2316-2340, 2317-2341, 2318-2342, 2319-2343, 2320-2344, 2321-2345, 2322-2346, 2323-2347, 2324-2348, 2325-2349, 2326-2350, 2327-2351, 2328-2352, 2329-2353, 2330-2354, 2331-2355, 2332-2356, 2333-2357, 2334-2358, 2335-2359, 2336-2360, 2337-2361, 2338-2362, 2339-2363, 2340-2364, 2341-2365, 2342-2366, 2343-2367, 2344-2368, 2345-2369, 2346-2370, 2347-2371, 2348-2372, 2349-2373, 2350-2374, 2351-2375, 2352-2376, 2353-2377, 2354-2378, 2355-2379, 2356-2380, 2357-2381, 2358-2382, 2359-2383, 2360-2384, 2361-2385, 2362-2386, 2363-2387, 2364-2388, 2365-2389, 2366-2390, 2367-2391, 2368-2392, 2369-2393, 2370-2394, 2371-2395, 2372-2396, 2373-2397, 2374-2398, 2375-2399, 2376-2400, 2377-2401, 2378-2402, 2379-2403, 2380-2404, 2381-2405, 2382-2406, 2383-2407, 2384-2408, 2385-2409, 2386-2410, 2387-2411, 2388-2412, 2389-2413, 2390-2414, 2391-2415, 2392-2416, 2393-2417, 2394-2418, 2395-2419, 2396-2420, 2397-2421, 2398-2422, 2399-2423, 2400-2424, 2401-2425, 2402-2426, 2403-2427, 2404-2428, 2405-2429, 2406-2430, 2407-2431, 2408-2432, 2409-2433, 2410-2434, 2411-2435, 2412-2436, 2413-2437, 2414-2438, 2415-2439, 2416-2440, 2417-2441, 2418-2442, 2419-2443, 2420-2444, 2421-2445, 2422-2446, 2423-2447, 2424-2448, 2425-2449, 2426-2450, 2427-2451, 2428-2452, 2429-2453, 2430-2454, 2431-2455, 2432-2456, 2433-2457, 2434-2458, 2435-2459, 2436-2460, 2437-2461, 2438-2462, 2439-2463, 2440-2464, 2441-2465, 2442-2466, 2443-2467, 2444-2468, 2445-2469, 2446-2470, 2447-2471, 2448-2472, 2449-2473, 2450-2474, 2451-2475, 2452-2476, 2453-2477, 2454-2478, 2455-2479, 2456-2480, 2457-2481, 2458-2482, 2459-2483, 2460-2484, 2461-2485, 2462-2486, 2463-2487, 2464-2488, 2465-2489, 2466-2490, 2467-2491, 2468-2492, 2469-2493, 2470-2494, 2471-2495, 2472-2496, 2473-2497, 2474-2498, 2475-2499, 2476-2500, 2477-2501, 2478-2502, 2479-2503, 2480-2504, 2481-2505, 2482-2506, 2483-2507, 2484-2508, 2485-2509, 2486-2510, 2487-2511, 2488-2512, 2489-2513, 2490-2514, 2491-2515, 2492-2516, 2493-2517, 2494-2518, 2495-2519, 2496-2520, 2497-2521, 2498-2522, 2499-2523, 2500-2524, 2501-2525, 2502-2526, 2503-2527, 2504-2528, 2505-2529, 2506-2530, 2507-2531, 2508-2532, 2509-2533, 2510-2534, 2511-2535, 2512-2536, 2513-2537, 2514-2538, 2515-2539, 2516-2540, 2517-2541, 2518-2542, 2519-2543, 2520-2544, 2521-2545, 2522-2546, 2523-2547, 2524-2548, 2525-2549, 2526-2550, 2527-2551, 2528-2552, 2529-2553, 2530-2554, 2531-2555, 2532-2556, 2533-2557, 2534-2558, 2535-2559, 2536-2560, 2537-2561, 2538-2562, 2539-2563, 2540-2564, 2541-2565, 2542-2566, 2543-2567, 2544-2568, 2545-2569, 2546-2570, 2547-2571, 2548-2572, 2549-2573, 2550-2574, 2551-2575, 2552-2576, 2553-2577, 2554-2578, 2555-2579, 2556-2580, 2557-2581, 2558-2582, 2559-2583, 2560-2584, 2561-2585, 2562-2586, 2563-2587, 2564-2588, 2565-2589, 2566-2590, 2567-2591, 2568-2592, 2569-2593, 2570-2594, 2571-2595, 2572-2596, 2573-2597, 2574-2598, 2575-2599, 2576-2600, 2577-2601, 2578-2602, 2579-2603, 2580-2604, 2581-2605, 2582-2606, 2583-2607, 2584-2608, 2585-2609, 2586-2610, 2587-2611, 2588-2612, 2589-2613, 2590-2614, 2591-2615, 2592-2616, 2593-2617, 2594-2618, 2595-2619, 2596-2620, 2597-2621, 2598-2622, 2599-2623, 2600-2624, 2601-2625, 2602-2626, 2603-2627, 2604-2628, 2605-2629, 2606-2630, 2607-2631, 2608-2632, 2609-2633, 2610-2634, 2611-2635, 2612-2636, 2613-2637, 2614-2638, 2615-2639, 2616-2640, 2617-2641, 2618-2642, 2619-2643, 2620-2644, 2621-2645, 2622-2646, 2623-2647, 2624-2648, 2625-2649, 2626-2650, 2627-2651, 2628-2652, 2629-2653, 2630-2654, 2631-2655, 2632-2656, 2633-2657, 2634-2658, 2635-2659, 2636-2660, 2637-2661, 2638-2662, 2639-2663, 2640-2664, 2641-2665, 2642-2666, 2643-2667, 2644-2668, 2645-2669, 2646-2670, 2647-2671, 2648-2672, 2649-2673, 2650-2674, 2651-2675, 2652-2676, 2653-2677, 2654-2678, 2655-2679, 2656-2680, 2657-2681, 2658-2682, 2659-2683, 2660-2684, 2661-2685, 2662-2686, 2663-2687, 2664-2688, 2665-2689, 2666-2690, 2667-2691, 2668-2692, 2669-2693, 2670-2694, 2671-2695, 2672-2696, 2673-2697, 2674-2698, 2675-2699, 2676-2700, 2677-2701, 2678-2702, 2679-2703, 2680-2704, 2681-2705, 2682-2706, 2683-2707, 2684-2708, 2685-2709, 2686-2710, 2687-2711, 2688-2712, 2689-2713, 2690-2714, 2691-2715, 2692-2716, 2693-2717, 2694-2718, 2695-2719, 2696-2720, 2697-2721, 2698-2722, 2699-2723, 2700-2724, 2701-2725, 2702-2726, 2703-2727, 2704-2728, 2705-2729, 2706-2730, 2707-2731, 2708-2732, 2709-2733, 2710-2734, 2711-2735, 2712-2736, 2713-2737, 2714-2738, 2715-2739, 2716-2740, 2717-2741, 2718-2742, 2719-2743, 2720-2744, 2721-2745, 2722-2746, 2723-2747, 2724-2748, 2725-2749, 2726-2750, 2727-2751, 2728-2752, 2729-2753, 2730-2754, 2731-2755, 2732-2756, 2733-2757, 2734-2758, 2735-2759, 2736-2760, 2737-2761, 2738-2762, 2739-2763, 2740-2764, 2741-2765, 2742-2766, 2743-2767, 2744-2768, 2745-2769, 2746-2770, 2747-2771, 2748-2772, 2749-2773, 2750-2774, 2751-2775, 2752-2776, 2753-2777, 2754-2778, 2755-2779, 2756-2780, 2757-2781, 2758-2782, 2759-2783, 2760-2784, 2761-2785, 2762-2786, 2763-2787, 2764-2788, 2765-2789, 2766-2790, 2767-2791, 2768-2792, 2769-2793, 2770-2794, 2771-2795, 2772-2796, 2773-2797, 2774-2798, 2775-2799, 2776-2800, 2777-2801, 2778-2802, 2779-2803, 2780-2804, 2781-2805, 2782-2806, 2783-2807, 2784-2808, 2785-2809, 2786-2810, 2787-2811, 2788-2812, 2789-2813, 2790-2814, 2791-2815, 2792-2816, 2793-2817, 2794-2818, 2795-2819, 2796-2820, 2797-2821, 2798-2822, 2799-2823, 2800-2824, 2801-2825, 2802-2826, 2803-2827, 2804-2828, 2805-2829, 2806-2830, 2807-2831, 2808-2832, 2809-2833, 2810-2834, 2811-2835, 2812-2836, 2813-2837, 2814-2838, 2815-2839, 2816-2840, 2817-2841, 2818-2842, 2819-2843, 2820-2844, 2821-2845, 2822-2846, 2823-2847, 2824-2848, 2825-2849, 2826-2850, 2827-2851, 2828-2852, 2829-2853, 2830-2854, 2831-2855, 2832-2856, 2833-2857, 2834-2858, 2835-2859, 2836-2860, 2837-2861, 2838-2862, 2839-2863, 2840-2864, 2841-2865, 2842-2866, 2843-2867, 2844-2868, 2845-2869, 2846-2870, 2847-2871, 2848-2872, 2849-2873, 2850-2874, 2851-2875, 2852-2876, 2853-2877, 2854-2878, 2855-2879, 2856-2880, 2857-2881, 2858-2882, 2859-2883, 2860-2884, 2861-2885, 2862-2886, 2863-2887, 2864-2888, 2865-2889, 2866-2890, 2867-2891, 2868-2892, 2869-2893, 2870-2894, 2871-2895, 2872-2896, 2873-2897, 2874-2898, 2875-2899, 2876-2900, 2877-2901, 2878-2902, 2879-2903, 2880-2904, 2881-2905, 2882-2906, 2883-2907, 2884-2908, 2885-2909, 2886-2910, 2887-2911, 2888-2912, 2889-2913, 2890-2914, 2891-2915, 2892-2916, 2893-2917, 2894-2918, 2895-2919, 2896-2920, 2897-2921, 2898-2922, 2899-2923, 2900-2924, 2901-2925, 2902-2926, 2903-2927, 2904-2928, 2905-2929, 2906-2930, 2907-2931, 2908-2932, 2909-2933, 2910-2934, 2911-2935, 2912-2936, 2913-2937, 2914-2938, 2915-2939, 2916-2940, 2917-2941, 2918-2942, 2919-2943, 2920-2944, 2921-2945, 2922-2946, 2923-2947, 2924-2948, 2925-2949, 2926-2950, 2927-2951, 2928-2952, 2929-2953, 2930-2954, 2931-2955, 2932-2956, 2933-2957, 2934-2958, 2935-2959, 2936-2960, 2937-2961, 2938-2962, 2939-2963, 2940-2964, 2941-2965, 2942-2966, 2943-2967, 2944-2968, 2945-2969, 2946-2970, 2947-2971, 2948-2972, 2949-2973, 2950-2974, 2951-2975, 2952-2976, 2953-2977, 2954-2978, 2955-2979, 2956-2980, 2957-2981, 2958-2982, 2959-2983, 2960-2984, 2961-2985, 2962-2986, 2963-2987, 2964-2988, 2965-2989, 2966-2990, 2967-2991, 2968-2992, 2969-2993, 2970-2994, 2971-2995, 2972-2996, 2973-2997, 2974-2998, 2975-2999, 2976-3000, 2977-3001, 2978-3002, 2979-3003, 2980-3004, 2981-3005, 2982-3006, 2983-3007, 2984-3008, 2985-3009, 2986-3010, 2987-3011, 2988-3012, 2989-3013, 2990-3014, 2991-3015, 2992-3016, 2993-3017, 2994-3018, 2995-3019, 2996-3020, 2997-3021, 2998-3022, 2999-3023, 3000-3024, 3001-3025, 3002-3026, 3003-3027, 3004-3028, 3005-3029, 3006-3030, 3007-3031, 3008-3032, 3009-3033, 3010-3034, 3011-3035, 3012-3036, 3013-3037, 3014-3038, 3015-3039, 3016-3040, 3017-3041, 3018-3042, 3019-3043, 3020-3044, 3021-3045, 3022-3046, 3023-3047, 3024-3048, 3025-3049, 3026-3050, 3027-3051, 3028-3052, 3029-3053, 3030-3054, 3031-3055, 3032-3056, 3033-3057, 3034-3058, 3035-3059, 3036-3060, 3037-3061, 3038-3062, 3039-3063, 3040-3064, 3041-3065, 3042-3066, 3043-3067, 3044-3068, 3045-3069, 3046-3070, 3047-3071, 3048-3072, 3049-3073, 3050-3074, 3051-3075, 3052-3076, 3053-3077, 3054-3078, 3055-3079, 3056-3080, 3057-3081, 3058-3082, 3059-3083, 3060-3084, 3061-3085, 3062-3086, 3063-3087, 3064-3088, 3065-3089, 3066-3090, 3067-3091, 3068-3092, 3069-3093, 3070-3094, 3071-3095, 3072-3096, 3073-3097, 3074-3098, 3075-3099, 3076-3100, 3077-3101, 3078-3102, 3079-3103, 3080-3104, 3081-3105, 3082-3106, 3083-3107, 3084-3108, 3085-3109, 3086-3110, 3087-3111, 3088-3112, 3089-3113, 3090-3114, 3091-3115, 3092-3116, 3093-3117, 3094-3118, 3095-3119, 3096-3120, 3097-3121, 3098-3122, 3099-3123, 3100-3124, 3101-3125, 3102-3126, 3103-3127, 3104-3128, 3105-3129, 3106-3130, 3107-3131, 3108-3132, 3109-3133, 3110-3134, 3111-3135, 3112-3136, 3113-3137, 3114-3138, 3115-3139, 3116-3140, 3117-3141, 3118-3142, 3119-3143, 3120-3144, 3121-3145,
3122-3146, 3123-3147, 3124-3148, 3125-3149, 3126-3150,
3127-3151, 3128-3152, 3129-3153, 3130-3154, 3131-3155,
3132-3156, 3133-3157, 3134-3158, 3135-3159, 3136-3160,
3137-3161, 3138-3162, 3139-3163, 3140-3164, 3141-3165,
3142-3166, 3143-3167, 3144-3168, 3145-3169, 3146-3170,
3147-3171, 3148-3172, 3149-3173, 3150-3174, 3151-3175,
3152-3176, 3153-3177, 3154-3178, 3155-3179, 3156-3180,
3157-3181, 3158-3182, 3159-3183, 3160-3184, 3161-3185,
3162-3186, 3163-3187, 3164-3188, 3165-3189, 3166-3190,
3167-3191, 3168-3192, 3169-3193, 3170-3194, 3171-3195,
3172-3196, 3173-3197, 3174-3198, 3175-3199, 3176-3200,
3177-3201, 3178-3202, 3179-3203, 3180-3204, 3181-3205,
3182-3206, 3183-3207, 3184-3208, 3185-3209, 3186-3210,
3187-3211, 3188-3212, 3189-3213, 3190-3214, 3191-3215,
3192-3216, 3193-3217, 3194-3218, 3195-3219, 3196-3220,
3197-3221, 3198-3222, 3199-3223, 3200-3224, 3201-3225,
3202-3226, 3203-3227, 3204-3228, 3205-3229, 3206-3230,
3207-3231, 3208-3232, 3209-3233, 3210-3234, 3211-3235,
3212-3236, 3213-3237, 3214-3238, 3215-3239, 3216-3240,
3217-3241, 3218-3242, 3219-3243, 3220-3244, 3221-3245,
3222-3246, 3223-3247, 3224-3248, 3225-3249, 3226-3250,
3227-3251, 3228-3252, 3229-3253, 3230-3254, 3231-3255,
3232-3256, 3233-3257, 3234-3258, 3235-3259, 3236-3260,
3237-3261, 3238-3262, 3239-3263, 3240-3264, 3241-3265,
3242-3266, 3243-3267, 3244-3268, 3245-3269, 3246-3270,
3247-3271, 3248-3272, 3249-3273, 3250-3274, 3251-3275,
3252-3276, 3253-3277, 3254-3278, 3255-3279, 3256-3280,
3257-3281, 3258-3282, 3259-3283, 3260-3284, 3261-3285,
3262-3286, 3263-3287, 3264-3288, 3265-3289, 3266-3290,
3267-3291, 3268-3292, 3269-3293, 3270-3294, 3271-3295,
3272-3296, 3273-3297, 3274-3298, 3275-3299, 3276-3300,
3277-3301, 3278-3302, 3279-3303, 3280-3304, 3281-3305,
3282-3306, 3283-3307, 3284-3308, 3285-3309, 3286-3310,
3287-3311, 3288-3312, 3289-3313, 3290-3314, 3291-3315,
3292-3316, 3293-3317, 3294-3318, 3295-3319, 3296-3320,
3297-3321, 3298-3322, 3299-3323, 3300-3324, 3301-3325,
3302-3326, 3303-3327, 3304-3328, 3305-3329, 3306-3330,
3307-3331, 3308-3332, 3309-3333, 3310-3334, 3311-3335,
3312-3336, 3313-3337, 3314-3338, 3315-3339, 3316-3340,
3317-3341, 3318-3342, 3319-3343, 3320-3344, 3321-3345,
3322-3346, 3323-3347, 3324-3348, 3325-3349, 3326-3350,
3327-3351, 3328-3352, 3329-3353, 3330-3354, 3331-3355,
3332-3356, 3333-3357, 3334-3358, 3335-3359, 3336-3360,
3337-3361, 3338-3362, 3339-3363, 3340-3364, 3341-3365,
3342-3366, 3343-3367, 3344-3368, 3345-3369, 3346-3370,
3347-3371, 3348-3372, 3349-3373, 3350-3374, 3351-3375,
3352-3376, 3353-3377, 3354-3378, 3355-3379, 3356-3380,
3357-3381, 3358-3382, 3359-3383, 3360-3384, 3361-3385,
3362-3386, 3363-3387, 3364-3388, 3365-3389, 3366-3390,
3367-3391, 3368-3392, 3369-3393, 3370-3394, 3371-3395,
3372-3396, 3373-3397, 3374-3398, 3375-3399, 3376-3400,
3377-3401, 3378-3402, 3379-3403, 3380-3404, 3381-3405,
3382-3406, 3383-3407, 3384-3408, 3385-3409, 3386-3410,
3387-3411, 3388-3412, 3389-3413, 3390-3414, 3391-3415,
3392-3416, 3393-3417, 3394-3418, 3395-3419, 3396-3420,
3397-3421, 3398-3422, 3399-3423, 3400-3424, 3401-3425,
3402-3426, 3403-3427, 3404-3428, 3405-3429, 3406-3430,
3407-3431, 3408-3432, 3409-3433, 3410-3434, 3411-3435,
3412-3436, 3413-3437, 3414-3438, 3415-3439, 3416-3440,
3417-3441, 3418-3442, 3419-3443, 3420-3444, 3421-3445,
3422-3446, 3423-3447, 3424-3448, 3425-3449, 3426-3450,
3427-3451, 3428-3452, 3429-3453, 3430-3454, 3431-3455,
3432-3456, 3433-3457, 3434-3458, 3435-3459, 3436-3460,
3437-3461, 3438-3462, 3439-3463, 3440-3464, 3441-3465,
3442-3466, 3443-3467, 3444-3468, 3445-3469, 3446-3470,
3447-3471, 3448-3472, 3449-3473, 3450-3474, 3451-3475,
3452-3476, 3453-3477, 3454-3478, 3455-3479, 3456-3480,
3457-3481, 3458-3482, 3459-3483, 3460-3484, 3461-3485,
3462-3486, 3463-3487, 3464-3488, 3465-3489, 3466-3490,
3467-3491, 3468-3492, 3469-3493, 3470-3494, 3471-3495,
3472-3496, 3473-3497, 3474-3498, 3475-3499, 3476-3500,
3477-3501, 3478-3502, 3479-3503, 3480-3504, 3481-3505,
3482-3506, 3483-3507, 3484-3508, 3485-3509, 3486-3510,
3487-3511, 3488-3512, 3489-3513, 3490-3514, 3491-3515,
3492-3516, 3493-3517, 3494-3518, 3495-3519, 3496-3520,
3497-3521, 3498-3522, 3499-3523, 3500-3524, 3501-3525,
3502-3526, 3503-3527, 3504-3528, 3505-3529, 3506-3530,
3507-3531, 3508-3532, 3509-3533, 3510-3534, 3511-3535,
3512-3536, 3513-3537, 3514-3538, 3515-3539, 3516-3540,
3517-3541, 3518-3542, 3519-3543, 3520-3544, 3521-3545,
3522-3546, 3523-3547, 3524-3548, 3525-3549, 3526-3550,
3527-3551, 3528-3552, 3529-3553, 3530-3554, 3531-3555,
3532-3556, 3533-3557, 3534-3558, 3535-3559, 3536-3560,
3537-3561, 3538-3562, 3539-3563, 3540-3564, 3541-3565,
3542-3566, 3543-3567, 3544-3568, 3545-3569, 3546-3570,
3547-3571, 3548-3572, 3549-3573, 3550-3574, 3551-3575,
3552-3576, 3553-3577, 3554-3578, 3555-3579, 3556-3580,
3557-3581, 3558-3582, 3559-3583, 3560-3584, 3561-3585,
3562-3586, 3563-3587, 3564-3588, 3565-3589, 3566-3590,
3567-3591, 3568-3592, 3569-3593, 3570-3594, 3571-3595,
3572-3596, 3573-3597, 3574-3598, 3575-3599, 3576-3600,
3577-3601, 3578-3602, 3579-3603, 3580-3604, 3581-3605,
3582-3606, 3583-3607, 3584-3608, 3585-3609, 3586-3610,
3587-3611, 3588-3612, 3589-3613, 3590-3614, 3591-3615,
3592-3616, 3593-3617, 3594-3618, 3595-3619, 3596-3620,
3597-3621, 3598-3622, 3599-3623, 3600-3624, 3601-3625,
3602-3626, 3603-3627, 3604-3628, 3605-3629, 3606-3630,
3607-3631, 3608-3632, 3609-3633, 3610-3634, 3611-3635,
3612-3636, 3613-3637, 3614-3638, 3615-3639, 3616-3640,
3617-3641, 3618-3642, 3619-3643, 3620-3644, 3621-3645,
3622-3646, 3623-3647, 3624-3648, 3625-3649, 3626-3650,
3627-3651, 3628-3652, 3629-3653, 3630-3654, 3631-3655,
3632-3656, 3633-3657, 3634-3658, 3635-3659, 3636-3660,
3637-3661, 3638-3662, 3639-3663, 3640-3664, 3641-3665,
3642-3666, 3643-3667, 3644-3668, 3645-3669, 3646-3670,
3647-3671, 3648-3672, 3649-3673, 3650-3674, 3651-3675,
3652-3676, 3653-3677, 3654-3678, 3655-3679, 3656-3680,
3657-3681, 3658-3682, 3659-3683, 3660-3684, 3661-3685,
3662-3686, 3663-3687, 3664-3688, 3665-3689, 3666-3690,
3667-3691, 3668-3692, 3669-3693, 3670-3694, 3671-3695,
3672-3696, 3673-3697, 3674-3698, 3675-3699, 3676-3700,
3677-3701, 3678-3702, 3679-3703, 3680-3704, 3681-3705,
3682-3706, 3683-3707, 3684-3708, 3685-3709, 3686-3710,
3687-3711, 3688-3712, 3689-3713, 3690-3714, 3691-3715,
3692-3716, 3693-3717, 3694-3718, 3695-3719, 3696-3720,
3697-3721, 3698-3722, 3699-3723, 3700-3724, 3701-3725,
3702-3726, 3703-3727, 3704-3728, 3705-3729, 3706-3730,
3707-3731, 3708-3732, 3709-3733, 3710-3734, 3711-3735,
3712-3736, 3713-3737, 3714-3738, 3715-3739, 3716-3740,
3717-3741, 3718-3742, 3719-3743, 3720-3744, 3721-3745,
3722-3746, 3723-3747, 3724-3748, 3725-3749, 3726-3750,
3727-3751, 3728-3752, 3729-3753, 3730-3754, 3731-3755,
3732-3756, 3733-3757, 3734-3758, 3735-3759, 3736-3760,
3737-3761, 3738-3762, 3739-3763, 3740-3764, 3741-3765,
3742-3766, 3743-3767, 3744-3768, 3745-3769, 3746-3770,
3747-3771, 3748-3772, 3749-3773, 3750-3774, 3751-3775,
3752-3776, 3753-3777, 3754-3778, 3755-3779, 3756-3780,
3757-3781, 3758-3782, 3759-3783, 3760-3784, 3761-3785,
3762-3786, 3763-3787, 3764-3788, 3765-3789, 3766-3790,
3767-3791, 3768-3792, 3769-3793, 3770-3794, 3771-3795,
3772-3796, 3773-3797, 3774-3798, 3775-3799, 3776-3800,
3777-3801, 3778-3802, 3779-3803, 3780-3804, 3781-3805,
3782-3806, 3783-3807, 3784-3808, 3785-3809, 3786-3810, 3787-3811, 3788-3812, 3789-3813, 3790-3814, 3791-3815, 3792-3816, 3793-3817, 3794-3818, 3795-3819, 3796-3820, 3797-3821, 3798-3822, 3799-3823, 3800-3824, 3801-3825, 3802-3826, 3803-3827, 3804-3828, 3805-3829, 3806-3830, 3807-3831, 3808-3832, 3809-3833, 3810-3834, 3811-3835, 3812-3836, 3813-3837, 3814-3838, 3815-3839, 3816-3840, 3817-3841, 3818-3842, 3819-3843, 3820-3844, 3821-3845, 3822-3846, 3823-3847, 3824-3848, 3825-3849, 3826-3850, 3827-3851, 3828-3852, 3829-3853, 3830-3854, 3831-3855, 3832-3856, 3833-3857, 3834-3858, 3835-3859, 3836-3860, 3837-3861, 3838-3862, 3839-3863, 3840-3864, 3841-3865, 3842-3866, 3843-3867, 3844-3868, 3845-3869, 3846-3870, 3847-3871, 3848-3872, 3849-3873, 3850-3874, 3851-3875, 3852-3876, 3853-3877, 3854-3878, 3855-3879, 3856-3880, 3857-3881, 3858-3882, 3859-3883, 3860-3884, 3861-3885, 3862-3886, 3863-3887, 3864-3888, 3865-3889, 3866-3890, 3867-3891, 3868-3892, 3869-3893, 3870-3894, 3871-3895, 3872-3896, 3873-3897, 3874-3898, 3875-3899, 3876-3900, 3877-3901, 3878-3902, 3879-3903, 3880-3904, 3881-3905, 3882-3906, 3883-3907, 3884-3908, 3885-3909, 3886-3910, 3887-3911, 3888-3912, 3889-3913, 3890-3914, 3891-3915, 3892-3916, 3893-3917, 3894-3918, 3895-3919, 3896-3920, 3897-3921, 3898-3922, 3899-3923, 3900-3924, 3901-3925, 3902-3926, 3903-3927, 3904-3928, 3905-3929, 3906-3930, 3907-3931, 3908-3932, 3909-3933, 3910-3934, 3911-3935, 3912-3936, 3913-3937, 3914-3938, 3915-3939, 3916-3940, 3917-3941, 3918-3942, 3919-3943, 3920-3944, 3921-3945, 3922-3946, 3923-3947, 3924-3948, 3925-3949, 3926-3950, 3927-3951, 3928-3952, 3929-3953, 3930-3954, 3931-3955, 3932-3956, 3933-3957, 3934-3958, 3935-3959, 3936-3960, 3937-3961, 3938-3962, 3939-3963, 3940-3964, 3941-3965, 3942-3966, 3943-3967, 3944-3968, 3945-3969, 3946-3970, 3947-3971, 3948-3972, 3949-3973, 3950-3974, 3951-3975, 3952-3976, 3953-3977, 3954-3978, 3955-3979, 3956-3980, 3957-3981, 3958-3982, 3959-3983, 3960-3984, 3961-3985, 3962-3986, 3963-3987, 3964-3988, 3965-3989, 3966-3990, 3967-3991, 3968-3992, 3969-3993, 3970-3994, 3971-3995, 3972-3996, 3973-3997, 3974-3998, and 3975-3999.

The present invention relates to antisense oligonucleotides designed to interfere with the normal function of Sos1 polynucleotides. Any modifications or variations of the antisense molecule which are known in the art to be broadly applicable to antisense technology are included within the scope of the invention. Such modifications include preparation of phosphorus-containing linkages as disclosed in U.S. Pat. Nos. 5,536,821; 5,541,306; 5,550,111; 5,563,253; 5,571,799; 5,587,361, 5,625,050 and 5,958,773.

The antisense compounds of the invention can include modified bases as disclosed in 5,958,773 and patents disclosed therein. The antisense oligonucleotides of the invention can also be modified by chemically linking the oligonucleotide to one or more moieties or conjugates to enhance the activity, cellular distribution, or cellular uptake of the antisense oligonucleotide. Such moieties or conjugates include lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567, 810, 5,574,142, 5,585,481, 5,587,371, 5,597,696 and 5,958, 773.

Chimeric antisense oligonucleotides are also within the scope of the invention, and can be prepared from the present inventive oligonucleotides using the methods described in, for example, U.S. Pat. Nos. 5,013,830, 5,149,797, 5,403, 711, 5,491,133, 5,565,350, 5,652,355, 5,700,922 and 5,958, 773.

Preferred antisense oligonucleotides in addition to those of SEQ ID NOs:2 and 3 can be selected by routine experimentation using, for example, assays described in the Examples. Although the inventors are not bound by a particular mechanism of action, it is believed that the antisense oligonucleotides achieve an inhibitory effect by binding to a complementary region of the target polynucleotide within the cell using Watson-Crick base pairing. Where the target polynucleotide is RNA, experimental evidence indicates that the RNA component of the hybrid is cleaved by RNase H (Giles et al., *Nuc. Acids Res.* 23:954-61, 1995; U.S. Pat. No. 6,001,653). Generally, a hybrid containing 10 base pairs is of sufficient length to serve as a substrate for RNase H. However, to achieve specificity of binding, it is preferable to use an antisense molecule of at least 17 nucleotides, as a sequence of this length is likely to be unique among human genes.

As disclosed in U.S. Pat. No. 5,998,383, incorporated herein by reference, the oligonucleotide is selected such that the sequence exhibits suitable energy related characteristics important for oligonucleotide duplex formation with their complementary templates, and shows a low potential for self-dimerization or self-complementation (Anazodo et al., *Biochem. Biophys. Res. Commun.* 229:305-09, 1996). The computer program OLIGO (Primer Analysis Software, Version 3.4), is used to determined antisense sequence melting temperature, free energy properties, and to estimate potential self-dimer formation and self-complimentarity properties. The program allows the determination of a qualitative estimation of these two parameters (potential self-dimer formation and self-complimentary) and provides an indication of "no potential" or "some potential" or "essentially complete potential." Segments of Sos1 polynucleotides are generally selected that have estimates of no potential in these parameters. However, segments can be used that have "some potential" in one of the categories. A balance of the parameters is used in the selection.

In the antisense art a certain degree of routine experimentation is required to select optimal antisense molecules for particular targets. To be effective, the antisense molecule preferably is targeted to an accessible, or exposed, portion of the target RNA molecule. Although in some cases information is available about the structure of target mRNA molecules, the current approach to inhibition using antisense is via experimentation. According to the invention, this experimentation can be performed routinely by transfecting cells with an antisense oligonucleotide using methods described in Example 1. mRNA levels in the cell can be measured routinely in treated and control cells by reverse transcription of the mRNA and assaying the cDNA levels. The biological effect can be determined routinely by measuring cell growth or viability as is known in the art.

Measuring the specificity of antisense activity by assaying and analyzing cDNA levels is an art-recognized method of validating antisense results. It has been suggested that RNA from treated and control cells should be reverse-transcribed and the resulting cDNA populations analyzed. (Branch, A. D., *T.I.B.S.* 23:45-50, 1998.) According to the present invention, cultures of SW620 cells were transfected with two different antisense oligonucleotides designed to target Sos 1 guanine nucleotide exchange factor. These oligonucleotides are shown in SEQ ID NOs:2 and 3. The levels of mRNA corresponding to Sos1 were measured in treated and control cells. SEQ ID NOs:2 and 3 caused decreases in Sos1 mRNA when normalized to β-actin mRNA levels.

Additional inhibitors include ribozymes, proteins or polypeptides, antibodies or fragments thereof as well as small molecules. Each of these Sos1 inhibitors share the common feature in that they reduce the expression and/or biological activity of Sos1. In addition to the exemplary Sos1 inhibitors disclosed herein, alternative inhibitors may be obtained through routine experimentation utilizing methodology either specifically disclosed herein or as otherwise readily available to and within the expertise of the skilled artisan.

Ribozymes

Sos1 inhibitors may be ribozymes. A ribozyme is an RNA molecule that specifically cleaves RNA substrates, such as mRNA, resulting in specific inhibition or interference with cellular gene expression. As used herein, the term ribozymes includes RNA molecules that contain antisense sequences for specific recognition, and an RNA-cleaving enzymatic activity. The catalytic strand cleaves a specific site in a target RNA at greater than stoichiometric concentration.

A wide variety of ribozymes may be utilized within the context of the present invention, including for example, the hammerhead ribozyme (for example, as described by Forster and Symons, *Cell* 48:211-20, 1987; Haseloff and Gerlach, *Nature* 328:596-600, 1988; Walbot and Bruening, *Nature* 334:196, 1988; Haseloff and Gerlach, *Nature* 334:585, 1988); the hairpin ribozyme (for example, as described by Haseloff et al., U.S. Pat. No. 5,254,678, issued Oct. 19, 1993 and Hempel et al., European Patent Publication No. 0 360 257, published Mar. 26, 1990); and Tetrahymena ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA/RNA).

Ribozymes can be targeted to any RNA transcript and can catalytically cleave such transcripts (see, e.g., U.S. Pat. No. 5,272,262; U.S. Pat. No. 5,144,019; and U.S. Pat. Nos. 5,168,053, 5,180,818, 5,116,742 and 5,093,246 to Cech et al.). According to certain embodiments of the invention, any such Sos1 mRNA-specific ribozyme, or a nucleic acid encoding such a ribozyme, may be delivered to a host cell to effect inhibition of Sos1 gene expression. Ribozymes and the like may therefore be delivered to the host cells by DNA encoding the ribozyme linked to a eukaryotic promoter, such as a eukaryotic viral promoter, such that upon introduction into the nucleus, the ribozyme will be directly transcribed.

RNAi

The invention also provides for the introduction of RNA with partial or fully double-stranded character into the cell or into the extracellular environment. Inhibition is specific to the Sos1 expression in that a nucleotide sequence from a portion of the target Sos1 gene is chosen to produce inhibitory RNA. This process is (1) effective in producing inhibition of gene expression, and (2) specific to the targeted Sos1 gene. The procedure may provide partial or complete loss of function for the target Sos1 gene. A reduction or loss of gene expression in at least 99% of targeted cells has been shown using comparable techniques with other target genes. Lower doses of injected material and longer times after administration of dsRNA may result in inhibition in a smaller fraction of cells. Quantitation of gene expression in a cell may show similar amounts of inhibition at the level of accumulation of target mRNA or translation of target protein. Methods of preparing and using RNAi are generally disclosed in U.S. Pat. No. 6,506,559, incorporated herein by reference.

The RNA may comprise one or more strands of polymerized ribonucleotide; it may include modifications to either the phosphate-sugar backbone or the nucleoside. The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses of double-stranded material may yield more effective inhibition. Inhibition is sequence-specific in that nucleotide sequences corresponding to the duplex region of the RNA are targeted for genetic inhibition. RNA containing a nucleotide sequences identical to a portion of the Sos1 target gene is preferred for inhibition. RNA sequences with insertions, deletions, and single point mutations relative to the target sequence have also been found to be effective for inhibition. Thus, sequence identity may optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region may be used to transcribe the RNA strand (or strands).

For RNAi, the RNA may be directly introduced into the cell (i.e., intracellularly); or introduced extracellularly into a cavity, interstitial space, into the circulation of an organism, introduced orally, or may be introduced by bathing an organism in a solution containing RNA. Methods for oral introduction include direct mixing of RNA with food of the organism, as well as engineered approaches in which a species that is used as food is engineered to express an RNA, then fed to the organism to be affected. Physical methods of introducing nucleic acids include injection directly into the cell or extracellular injection into the organism of an RNA solution.

The advantages of the method include the ease of introducing double-stranded RNA into cells, the low concentration of RNA which can be used, the stability of double-stranded RNA, and the effectiveness of the inhibition.

Inhibition of gene expression refers to the absence (or observable decrease) in the level of protein and/or mRNA product from a Sos1 target gene. Specificity refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of dsRNA may result in inhibition in a smaller fraction of cells (e.g., at least 10%, 20%, 50%, 75%, 90%, or 95% of targeted cells). Quantitation of Sos1 gene expression in a cell may show similar amounts of inhibition at the level of accumulation of Sos1 target mRNA or translation of Sos1 target protein. As an example, the efficiency of inhibition may be determined by assessing the amount of gene product in the cell: mRNA may be detected with a hybridization probe having a nucleotide sequence outside the region used for the inhibitory double-stranded RNA, or translated polypeptide may be detected with an antibody raised against the polypeptide sequence of that region.

The RNA may comprise one or more strands of polymerized ribonucleotide. It may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition while avoiding a general panic response in some organisms which is generated by dsRNA. Likewise, bases may be modified to block the activity of adenosine deaminase. RNA may be produced enzymatically or by partial/total organic synthesis, any modified ribonucleotide can be introduced by in vitro enzymatic or organic synthesis.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition.

RNA containing a nucleotide sequences identical to a portion of the Sos 1 target gene are preferred for inhibition. RNA sequences with insertions, deletions, and single point mutations relative to the target sequence may be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the Sos1 target gene is preferred. Alternatively, the duplex region of the RNA may be defined functionally as a nucleotide sequence that is capable of hybridizing with a portion of the Sos1 target gene transcript (e.g., 400 mM NaCl, 40 mM PIPES pH 6.4, 1 mM EDTA, 50° C. or 70° C. hybridization for 12-16 hours; followed by washing). The length of the identical nucleotide sequences may be at least 25, 50, 100, 200, 300 or 400 bases.

100% sequence identity between the RNA and the Sos1 target gene is not required to practice the present invention. Thus the methods have the advantage of being able to tolerate sequence variations that might be expected due to genetic mutation, strain polymorphism, or evolutionary divergence.

Sos1 RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

RNA may be directly introduced into the cell (i.e., intracellularly); or introduced extracellularly into a cavity, interstitial space, into the circulation of an organism, introduced orally, or may be introduced by bathing an organism in a solution containing the RNA. Methods for oral introduction include direct mixing of the RNA with food of the organism, as well as engineered approaches in which a species that is used as food is engineered to express the RNA, then fed to the organism to be affected. For example, the RNA may be sprayed onto a plant or a plant may be genetically engineered to express the RNA in an amount sufficient to kill some or all of a pathogen known to infect the plant. Physical methods of introducing nucleic acids, for example, injection directly into the cell or extracellular injection into the organism, may also be used. Vascular or extravascular circulation, the blood or lymph system, and the cerebrospinal fluid are sites where the RNA may be introduced. A transgenic organism that expresses RNA from a recombinant construct may be produced by introducing the construct into a zygote, an embryonic stem cell, or another multipotent cell derived from the appropriate organism.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, promote annealing of the duplex strands, stabilize the annealed strands, or other-wise increase inhibition of the target gene.

The present invention may be used alone or as a component of a kit having at least one of the reagents necessary to carry out the in vitro or in vivo introduction of RNA to test samples or subjects. Preferred components are the dsRNA and a vehicle that promotes introduction of the dsRNA. Such a kit may also include instructions to allow a user of the kit to practice the invention.

Suitable injection mixes are constructed so animals receive an average of $0.5 \times 10^6$ to $1.0 \times 10^6$ molecules of RNA. For comparisons of sense, antisense, and dsRNA activities, injections are compared with equal masses of RNA (i.e., dsRNA at half the molar concentration of the single strands). Numbers of molecules injected per adult are given as rough approximations based on concentration of RNA in the injected material (estimated from ethidium bromide staining) and injection volume (estimated from visible displacement at the site of injection). A variability of several-fold in injection volume between individual animals is possible.

Proteins and Polypeptides

In addition to the antisense molecules and ribozymes disclosed herein, Sos1 inhibitors of the present invention also include proteins or polypeptides that are effective in either reducing Sos1 gene expression or in decreasing one or more of Sos1's biological activities. A variety of methods are readily available in the art by which the skilled artisan may, through routine experimentation, rapidly identify such Sos1 inhibitors. The present invention is not limited by the following exemplary methodologies.

Literature is available to the skilled artisan that describes methods for detecting and analyzing protein-protein interactions. Reviewed in Phizicky et al., *Microbiological Reviews* 59:94-123, 1995, incorporated herein by reference. Such methods include, but are not limited to physical methods such as, e.g., protein affinity chromatography, affinity blotting, immunoprecipitation and cross-linking as well as library-based methods such as, e.g., protein probing, phage display and two-hybrid screening. Other methods that may be employed to identify protein-protein interactions include genetic methods such as use of extragenic suppressors, synthetic lethal effects and unlinked noncomplementation. Exemplary methods are described in further detail below.

Inventive Sos1 inhibitors may be identified through biological screening assays that rely on the direct interaction between the Sos1 protein and a panel or library of potential inhibitor proteins. Biological screening methodologies, including the various "n-hybrid technologies," are described in, for example, Vidal et al., *Nucl. Acids Res.* 27(4):919-29, 1999; Frederickson, R. M., *Curr. Opin. Biotechnol.* 9(1):90-96, 1998; Brachmann et al., *Curr. Opin. Biotechnol.* 8(5): 561-68, 1997; and White, M. A., *Proc. Natl. Acad. Sci. U.S.A.* 93:10001-03, 1996, each of which is incorporated herein by reference.

The two-hybrid screening methodology may be employed to search new or existing target cDNA libraries for Sos1 binding proteins that have inhibitory properties. The two-hybrid system is a genetic method that detects protein-protein interactions by virtue of increases in transcription of reporter genes. The system relies on the fact that site-specific transcriptional activators have a DNA-binding domain and a transcriptional activation domain. The DNA-binding domain targets the activation domain to the specific genes to be expressed. Because of the modular nature of transcriptional activators, the DNA-binding domain may be severed covalently from the transcriptional activation domain without loss of activity of either domain. Furthermore, these two domains may be brought into juxtaposition by protein-protein contacts between two proteins unrelated to the transcriptional machinery. Thus, two hybrids are constructed to create a functional system. The first hybrid, i.e., the bait, consists of a transcriptional activator DNA-binding domain fused to a protein of interest. The second hybrid, the target, is created by the fusion of a transcriptional activation domain with a library of proteins or polypeptides. Interaction between the bait protein and a member of the target library results in the juxtaposition of the DNA-binding domain and the transcriptional activation domain and the consequent up-regulation of reporter gene expression.

A variety of two-hybrid based systems are available to the skilled artisan that most commonly employ either the yeast Gal4 or *E. coli* LexA DNA-binding domain (BD) and the yeast Gal4 or herpes simplex virus VP 16 transcriptional activation domain. Chien et al., *Proc. Natl. Acad. Sci. U.S.A.* 88:9578-82, 1991; Dalton et al., *Cell* 68:597-612, 1992; Durfee et al., *Genes Dev.* 7:555-69, 1993; Vojtek et al., *Cell* 74:205-14, 1993; and Zervos et al., *Cell* 72:223-32, 1993. Commonly used reporter genes include the *E. coli* lacZ gene as well as selectable yeast genes such as HIS3 and LEU2. Fields et al., *Nature(London)* 340:245-46, 1989; Durfee, T. K., supra; and Zervos, A. S., supra. A wide variety of activation domain libraries is readily available in the art such that the screening for interacting proteins may be performed through routine experimentation.

Suitable bait proteins for the identification of Sos1 interacting proteins may be designed based on the Sos1 cDNA sequence presented herein as SEQ ID NO: 1. Such bait proteins include either the full-length Sos1 protein or fragments thereof.

Plasmid vectors, such as, e.g., pBTM116 and pAS2-1, for preparing Sos1 bait constructs and target libraries are readily available to the artisan and may be obtained from such commercial sources as, e.g., Clontech (Palo Alto, Calif.), Invitrogen (Carlsbad, Calif.) and Stratagene (La Jolla, Calif.). These plasmid vectors permit the in-frame fusion of cDNAs with the DNA-binding domains as LexA or Gal4BD, respectively.

Sos1 inhibitors of the present invention may alternatively be identified through one of the physical or biochemical methods available in the art for detecting protein-protein interactions.

Through the protein affinity chromatography methodology, lead compounds to be tested as potential Sos1 inhibitors may be identified by virtue of their specific retention to Sos1 when either covalently or non-covalently coupled to a solid matrix such as, e.g., Sepharose beads. The preparation of protein affinity columns is described in, for example, Beeckmans et al., *Eur J. Biochem.* 117:527-35, 1981, and Formosa et al., *Methods Enzymol.* 208:24-45, 1991. Cell lysates containing the full complement of cellular proteins may be passed through the Sos1 affinity column. Proteins having a high affinity for Sos1 will be specifically retained under low-salt conditions while the majority of cellular proteins will pass through the column. Such high affinity proteins may be eluted from the immobilized Sos1 under conditions of high-salt, with chaotropic solvents or with sodium dodecyl sulfate (SDS). In some embodiments, it may be preferred to radiolabel the cells prior to preparing the lysate as an aid in identifying the Sos1 specific binding proteins. Methods for radiolabeling mammalian cells are well known in the art and are provided, e.g., in Sopta et al., *J. Biol. Chem.* 260:10353-60, 1985.

Suitable Sos1 proteins for affinity chromatography may be fused to a protein or polypeptide to permit rapid purification on an appropriate affinity resin. For example, the Sos1 cDNA may be fused to the coding region for glutathione S-transferase (GST) which facilitates the adsorption of fusion proteins to glutathione-agarose columns. Smith et al., *Gene* 67:31-40, 1988. Alternatively, fusion proteins may include protein A, which can be purified on columns bearing immunoglobulin G; oligohistidine-containing peptides, which can be purified on columns bearing $Ni^{2+}$; the maltose-binding protein, which can be purified on resins containing amylose; and dihydrofolate reductase, which can be purified on methotrexate columns. One exemplary tag suitable for the preparation of Sos1 fusion proteins that is presented herein is the epitope for the influenza virus hemagglutinin (HA) against which monoclonal antibodies are readily available and from which antibodies an affinity column may be prepared.

Proteins that are specifically retained on a Sos1 affinity column may be identified after subjecting to SDS polyacrylamide gel electrophoresis (SDS-PAGE). Thus, where cells are radiolabeled prior to the preparation of cell lysates and passage through the Sos1 affinity column, proteins having high affinity for Sos1 may be detected by autoradiography. The identity of Sos1 specific binding proteins may be determined by protein sequencing techniques that are readily available to the skilled artisan, such as Mathews, C. K. et al., *Biochemistry*, The Benjamin/Cummings Publishing Company, Inc., 1990, pp.166-70.

Small Molecules

The present invention also provides small molecule Sos1 inhibitors that may be readily identified through routine application of high-throughput screening (HTS) methodologies. Reviewed by Persidis, A., *Nature Biotechnology* 16:488-89, 1998. HTS methods generally refer to those technologies that permit the rapid assaying of lead compounds, such as small molecules, for therapeutic potential. HTS methodology employs robotic handling of test materials, detection of positive signals and interpretation of data. Such methodologies include, e.g., robotic screening technology using soluble molecules as well as cell-based systems such as the two-hybrid system described in detail above.

A variety of cell line-based HTS methods are available that benefit from their ease of manipulation and clinical relevance of interactions that occur within a cellular context as opposed to in solution. Lead compounds may be identified via incorporation of radioactivity or through optical assays that rely on absorbance, fluorescence or luminescence as read-outs. See, e.g., Gonzalez et al., *Curr. Opin. Biotechnol.* 9(6):624-31, 1998, incorporated herein by reference.

HTS methodology may be employed, e.g., to screen for lead compounds that block one of Sos1's biological activities. By this method, Sos1 protein may be immunoprecipitated from cells expressing the protein and applied to wells on an assay plate suitable for robotic screening. Individual test compounds may then be contacted with the immunoprecipitated protein and the effect of each test compound on Sos1.

Methods for Assessing the Efficacy of Sos1 Inhibitors

Lead molecules or compounds, whether antisense molecules or ribozymes, proteins and/or peptides, antibodies and/or antibody fragments or small molecules, that are identified either by one of the methods described herein or via techniques that are otherwise available in the art, may be further characterized in a variety of in vitro, ex vivo and in vivo animal model assay systems for their ability to inhibit Sos 1 gene expression or biological activity. As discussed in further detail in the Examples provided below, Sos1 inhibitors of the present invention are effective in reducing Sos1 expression levels. Thus, the present invention further discloses methods that permit the skilled artisan to assess the effect of candidate inhibitors.

Candidate Sos1 inhibitors may be tested by administration to cells that either express endogenous Sos1 or that are made to express Sos1 by transfection of a mammalian cell with a recombinant Sos1 plasmid construct.

Effective Sos1 inhibitory molecules will be effective in reducing the exchange activity of Sos1 or inhibit the interaction with Ras. For a general description of these procedures, see, e.g., Sambrook et al., *Molecular Cloning: A Laboratory Manual*, Cold Spring Harbor Press, 1989, and Glick, B. R. and J. J. Pasternak (eds.), *Molecular Biotechnology: Principles and Applications of Recombinant DNA*, ASM Press, 1998, incorporated herein by reference. The effectiveness of a given candidate antisense molecule may be assessed by comparison with a control "antisense" molecule known to have no substantial effect on Sos1 expression when administered to a mammalian cell. Exemplary control molecules include the Sos1 oligonucleotides of SEQ ID NOs:6 and 7.

In alternate embodiments of the present invention, the effect of Sos1 inhibitors on the rate of DNA synthesis after challenge with a radiation or chemotherapeutic agent may be assessed by, e.g., the method of Young and Painter. *Hum. Genet.* 82:113-17, 1989. Briefly, culture cells may be incubated in the presence of $^{14}C$-thymidine prior to exposure to, e.g., X-rays. Immediately after irradiation, cells are incubated for a short period prior to addition of $^{3}H$-thymidine. Cells are washed, treated with perchloric acid and filtered (Whatman GF/C). The filters are rinsed with perchloric acid, 70% alcohol and then 100% ethanol; radioactivity is measured and the resulting $^{3}H/^{14}C$ ratios used to determine the rates of DNA synthesis.

Sos1 inhibitors effective in reducing Sos1 gene expression by one or more of the methods discussed above may be further characterized in vivo for efficacy in one of the readily available animal model systems. Various animal model systems for study of cancer and genetic instability associated genes are disclosed in, for example, Donehower, L. A. *Cancer Surveys* 29:329-52, 1997, incorporated herein by reference.

Pharmaceutical Compositions

The antisense oligonucleotides and ribozymes of the present invention can be synthesized by any method known in the art for ribonucleic or deoxyribonucleic nucleotides. For example, the oligonucleotides can be prepared using solid-phase synthesis such as in an Applied Biosystems 380B DNA synthesizer. Final purity of the oligonucleotides is determined as is known in the art.

The antisense oligonucleotides identified using the methods of the invention modulate tumor cell proliferation.

Therefore, pharmaceutical compositions and methods are provided for interfering with cell proliferation, preferably tumor cell proliferation, comprising contacting tissues or cells with one or more of antisense oligonucleotides identified using the methods of the invention. Preferably, an antisense oligonucleotide having one of SEQ ID NOs:2 and 3 is administered.

The methods and compositions may also be used to treat proliferative disorders including other forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, colon cancer, pancreatic cancer, head and neck cancers, and nervous system cancers, benign lesions such as papillomas, arthrosclerosis, psoriasis, primary and secondary polythemia, mastocytosis, autoimmune diseases, angiogenesis, bacterial infections, and viral infections, such as HIV infections, hepatitis or herpes infections.

The invention provides pharmaceutical compositions of antisense oligonucleotides and ribozymes complementary to the Sos1 mRNA gene sequence as active ingredients for therapeutic application. These compositions can also be used in the method of the present invention. When required, the compounds are nuclease resistant. In general the pharmaceutical composition for modulating cell proliferation or for cytotoxicity in a mammal includes an effective amount of at least one antisense oligonucleotide as described above needed for the practice of the invention, or a fragment thereof shown to have the same effect, and a pharmaceutically physiologically acceptable carrier or diluent.

In one embodiment of the invention, a method is provided for reducing metastasis in a subject comprising administering an amount of an antisense oligonucleotide of the invention effective to reduce metastasis. Most preferably the antisense oligonucleotide is one of SEQ ID NOs:2 and 3.

The pharmaceutical composition for inhibiting tumorigenicity of neoplastic cells in a mammal consists of an effective amount of at least one active ingredient selected from antisense oligonucleotides complementary to the Sos1 mRNA, including the entire Sos1 mRNA or having short sequences as set forth in SEQ ID NOs:2 and 3 and a pharmaceutically physiologically acceptable carrier or diluent. Combinations of the active ingredients can be used.

The compositions can be administered orally, subcutaneously, or parenterally including intravenous, intraarterial, intramuscular, intraperitoneally, and intranasal administration, as well as intrathecal and infusion techniques as required by the malignant cells being treated. For delivery within the CNS, intrathecal delivery can be used with, for example, an Ommaya reservoir or other methods known in the art. The pharmaceutically acceptable carriers, diluents, adjuvants and vehicles as well as implant carriers generally refer to inert, non-toxic solid or liquid fillers, diluents or encapsulating material not reacting with the active ingredients of the invention. Cationic lipids may also be included in the composition to facilitate oligonucleotide uptake. Implants of the compounds are also useful. In general, the pharmaceutical compositions are sterile.

In the method of the present invention, proliferating cells including neoplastic cells are contacted with a growth-inhibiting amount of the bioactive antisense oligonucleotide for the Sos1 mRNA or a fragment thereof shown to have substantially the same effect. In an embodiment, the mammal to be treated is human, but other mammalian species can be treated in veterinary applications.

By bioactive (expressible) is meant that the oligonucleotide is biologically active in the cell when delivered directly to the cell and/or is expressed by an appropriate promotor and active when delivered to the cell in a vector as described below. Nuclease resistance is provided by any method known in the art that does not substantially interfere with biological activity as described herein.

"Contacting the cell" refers to methods of exposing or delivering to a cell antisense oligonucleotides whether directly or by viral or non-viral vectors and where the antisense oligonucleotide is bioactive upon delivery. The method of delivery will be chosen for the particular cancer being treated. Parameters that affect delivery can include the cell type affected and tumor location, as is known in the medical art.

The treatment generally has a length proportional to the length of the disease process, and drug effectiveness, and the patient species being treated. It is noted that humans are treated generally longer than the Examples exemplified herein, which treatment has a length proportional to the length of the disease process and drug effectiveness. The doses may be single doses or multiple doses as determined by the medical practitioners and treatment courses will be repeated as necessary until diminution of the disease is achieved. Optimal dosing schedules may be calculated using measurements of drug accumulation in the body. Practitioners of ordinary skill in the art can readily determine optimum dosages, dosing methodologies, and repetition rates. Optimum dosages may vary depending on the relative potency of the antisense oligonucleotide, and can generally be determined based on values in in vitro and in vivo animal studies and clinical trials. Variations in the embodiments used may also be utilized. The amount must be effective to achieve improvement including but not limited to decreased tumor growth, or tumor size reduction or to improved survival rate or length or decreased drug resistance or other indicators as are selected as appropriate measures by those skilled in the art.

Although some antisense oligonucleotides may not completely abolish tumor cell growth in vitro, these antisense compounds may be clinically useful if they inhibit tumor growth enough to allow complementary treatments, such as chemotherapy, to be effective. The pharmaceutical compositions of the present invention therefore are administered singly or in combination with other drugs, such as cytotoxic agents, immunotoxins, alkylating agents, anti-metabolites, antitumor antibiotics and other anti-cancer drugs and treatment modalities that are known in the art. The composition is administered and dosed in accordance with good medical practice taking into account the clinical condition of the individual patient, the site and method of administration, scheduling of administration, and other factors known to medical practitioners. The "effective amount" for growth inhibition is thus determined by such considerations as are known in the art. The pharmaceutical composition may contain more than one embodiment of the present invention.

The nucleotide sequences of the present invention can be delivered either directly or with viral or non-viral vectors. When delivered directly the sequences are generally rendered nuclease resistant. Alternatively, the sequences can be incorporated into expression cassettes or constructs such that the sequence is expressed in the cell. Generally, the construct contains the proper regulatory sequence or promotor to allow the sequence to be expressed in the targeted cell.

Once the oligonucleotide sequences are ready for delivery they can be introduced into cells as is known in the art.

Transfection, electroporation, fusion, liposomes, colloidal polymeric particles, and viral vectors as well as other means known in the art may be used to deliver the oligonucleotide sequences to the cell. The method selected will depend at least on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, viral vectors, or the like.

The present invention provides vectors comprising an expression control sequence operatively linked to the oligonucleotide sequences of the invention. The present invention further provides host cells, selected from suitable eucaryotic and procaryotic cells, which are transformed with these vectors as necessary. Such transformed cells allow the study of the function and the regulation of malignancy and the treatment therapy of the present invention.

Vectors are known or can be constructed by those skilled in the art and should contain all expression elements necessary to achieve the desired transcription of the sequences. Other beneficial characteristics can also be contained within the vectors such as mechanisms for recovery of the oligonucleotides in a different form. Phagemids are a specific example of such beneficial vectors because they can be used either as plasmids or as bacteriophage vectors. Examples of other vectors include viruses such as bacteriophages, baculoviruses and retroviruses, DNA viruses, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual*, Cold Springs Harbor Laboratory, N.Y., 1989, 1992; in Ausubel et al., *Current Protocols in Molecular Biology*, John Wiley and Sons, Baltimore, Md., 1989; Chang et al., *Somatic Gene Therapy*, CRC Press, Ann Arbor, Mich., 1995; Vega et al., *Gene Targeting*, CRC Press, Ann Arbor, Mich., 1995; *Vectors: A Survey of Molecular Cloning Vectors and Their Uses*, Butterworths, Boston, Mass., 1988; and Gilboa et al., *BioTechniques* 4:504-12, 1986, and include, for example, stable or transient transfection, lipofection, electroporation and infection with recombinant viral vectors.

Recombinant methods known in the art can also be used to achieve the antisense inhibition of a target nucleic acid. For example, vectors containing antisense nucleic acids can be employed to express an antisense message to reduce the expression of the target nucleic acid and therefore its activity.

The present invention also provides a method of evaluating if a compound inhibits transcription or translation of an Sos1 gene and thereby modulates (i.e., reduces) cell proliferation comprising transfecting a cell with an expression vector comprising a nucleic acid sequence encoding Sos1, the necessary elements for the transcription or translation of the nucleic acid; administering a test compound; and comparing the level of expression of the Sos1 with the level obtained with a control in the absence of the test compound.

The present invention provides detectably labeled oligonucleotides for imaging Sos1 polynucleotides within a cell. Such oligonucleotides are useful for determining if gene amplification has occurred, and for assaying the expression levels in a cell or tissue using, for example, in situ hybridization as is known in the art.

While the present invention has been described with specificity in accordance with certain of its preferred embodiments, the following examples serve only to illustrate the invention and are not intended to limit the invention.

EXAMPLES

Example 1

Antisense Inhibition of Target RNA

A. Preparation of Oligonucleotides for Transfection

A carrier molecule, comprising either a lipitoid or cholesteroid, was prepared for transfection by diluting to 0.5 mM in water, followed by sonication to produce a uniform solution, and filtration through a 0.45 µm PVDF membrane. The lipitoid or cholesteroid was then diluted into an appropriate volume of OptiMEM™ (Gibco/BRL) such that the final concentration would be approximately 1.5-2 mmol lipitoid per µg oligonucleotide.

Antisense and control oligonucleotides were prepared by first diluting to a working concentration of 100 µM in sterile Millipore water, then diluting to 2 µM (approximately 20 mg/mL) in OptiMEM™. The diluted oligonucleotides were then immediately added to the diluted lipitoid and mixed by pipetting up and down.

Antisense oligonucleotides specific for Sos1 are shown in SEQ ID NO:2 and 3. The corresponding reverse control oligonucleotides are shown in SEQ ID NO:6 and 7, respectively.

B. Transfection

SW620 or BT474 cells were plated in growth media with serum at $2\times10^5$ cells per well in 6-well culture dishes, and allowed to incubate overnight. The cells were then transfected by adding the oligonucleotide/lipitoid mixture, immediately after mixing, to a final concentration of 300 nM oligonucleotide. The cells were then incubated with the transfection mixture overnight at 37° C., 5% $CO_2$ and the transfection mixture remained on the cells for 3-4 days.

C. Total RNA Extraction and Reverse Transcription

Total RNA was extracted from the transfected cells using the RNeasy™ kit (Qiagen Corporation, Chatsworth, Calif.), following protocols provided by the manufacturer. Following extraction, the RNA was reverse-transcribed for use as a PCR template. Generally 0.2-1 µg of total extracted RNA was placed into a sterile microfuge tube, and water was added to bring the total volume to 3 µL. 7 µL of a buffer/enzyme mixture was added to each tube. The buffer/enzyme mixture was prepared by mixing, in the order listed:

4 µL 25 mM $MgCl_2$

2 µL 10× reaction buffer

8 µL 2.5 mM dNTPs

1 µL MuLV reverse transcriptase (50 u) (Applied Biosystems)

1 µL RNase inhibitor (20 u)

1 µL oligo dT (50 pmol).

The contents of the microfuge tube were mixed by pipetting up and down, and the reaction was incubated for 1 hour at 42° C.

D. PCR Amplification and Quantification of Target Sequences

Figure 3B:
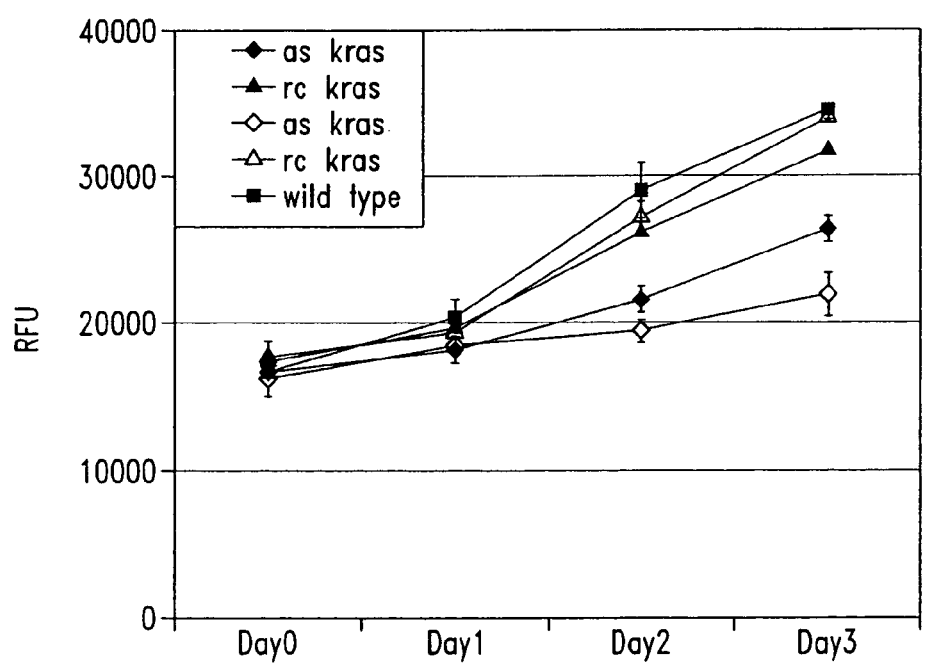
Figure 3C:
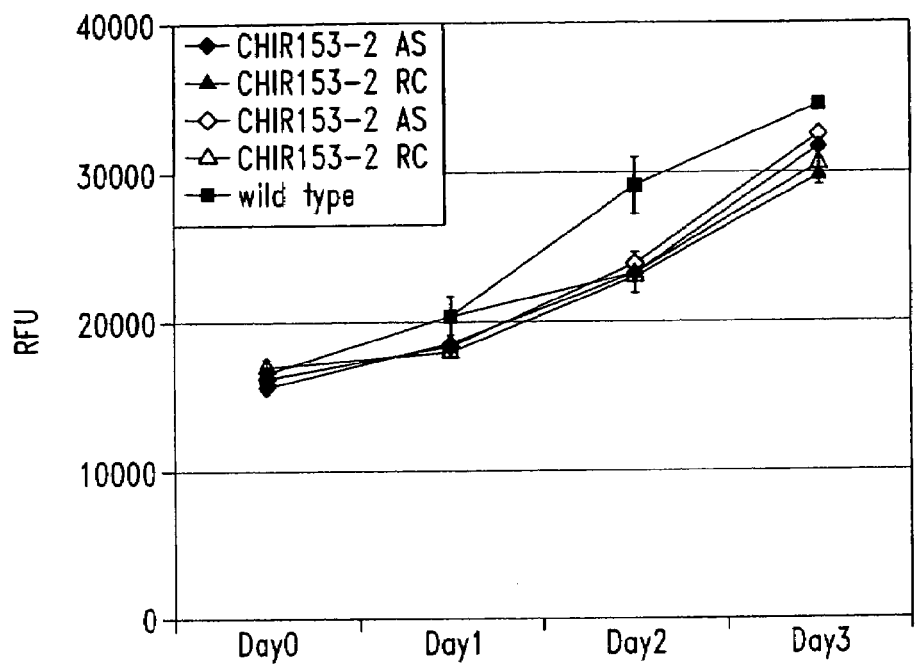
Figure 3D:
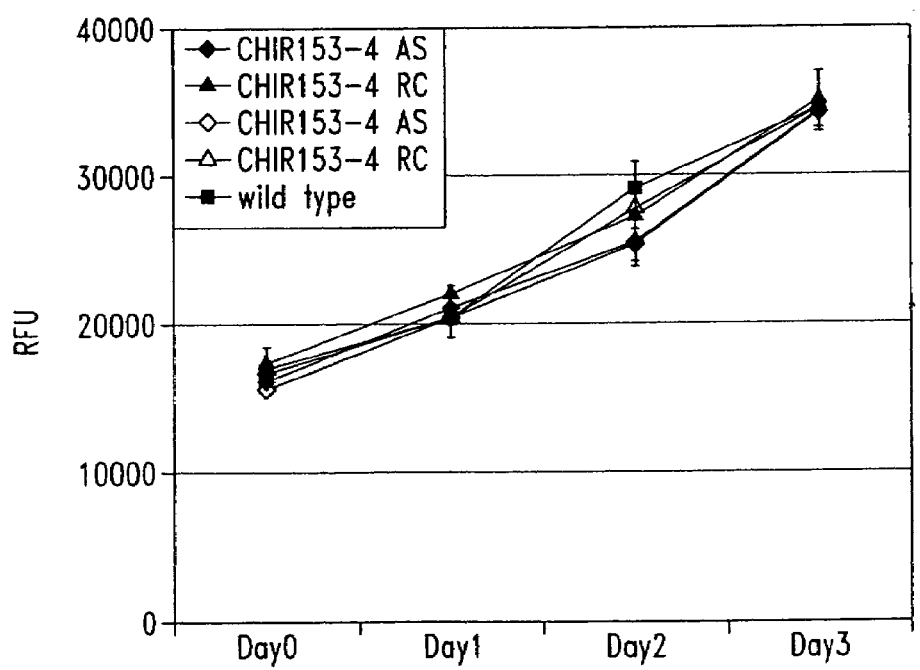
Figure 4A:
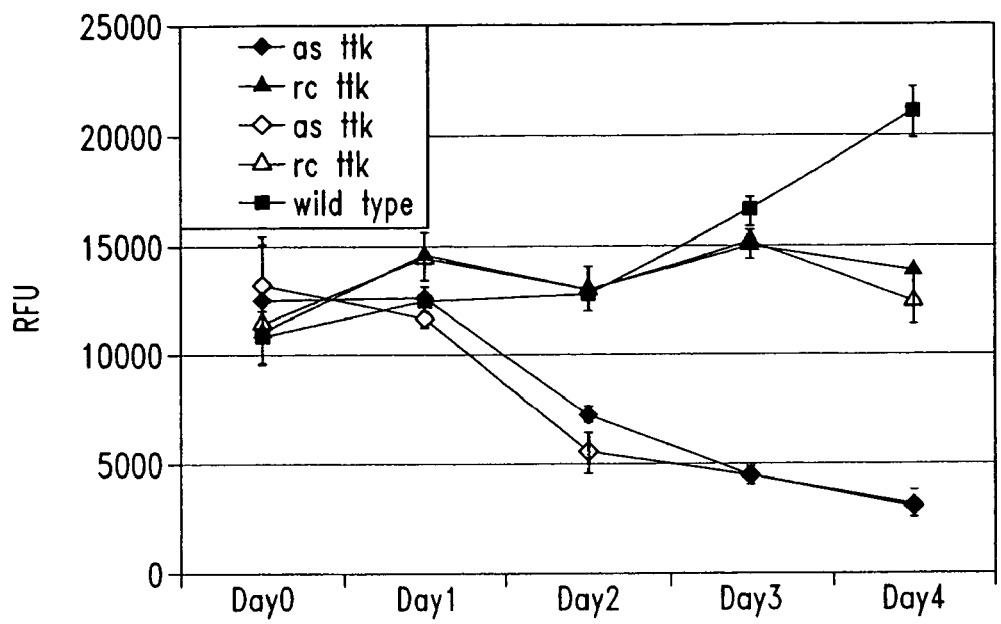
FIG. 4 shows the results of a proliferation assay of BT474 cells transfected with the following oligonucleotides: (4A) ttk antisense and reverse control (SEQ ID NO: 10 and 11); (4B) Her2/neu antisense and reverse control (SEQ ID NO:5 and 9); (4C) kras antisense and reverse control (SEQ ID NO:4 and 8); and (4D) Sos1 antisense and reverse control (SEQ ID NO:2 and 6).
Figure 4B:
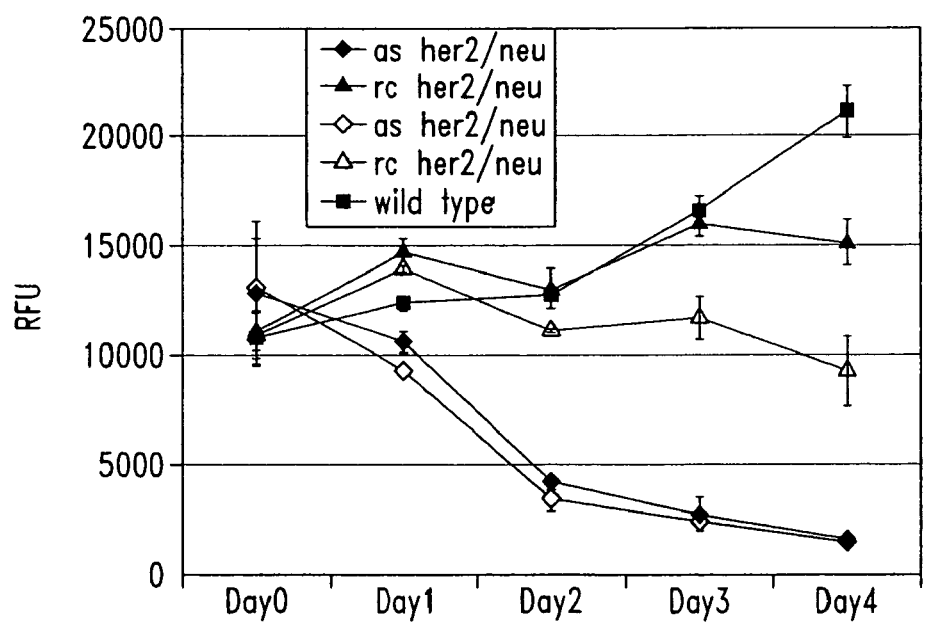
Figure 4C:
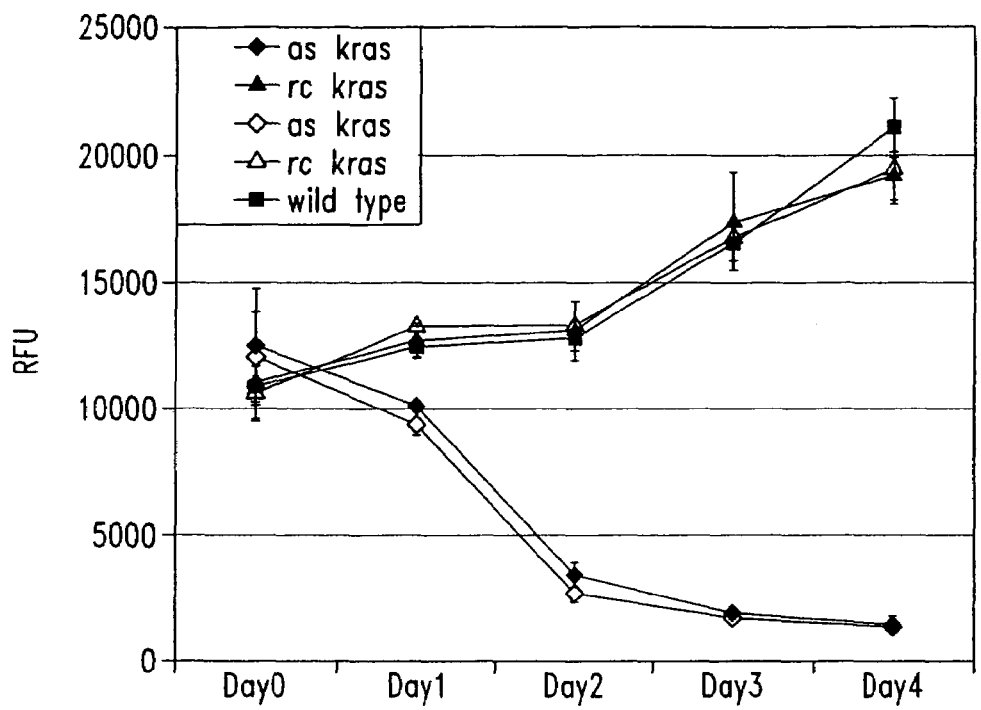
Figure 4D:
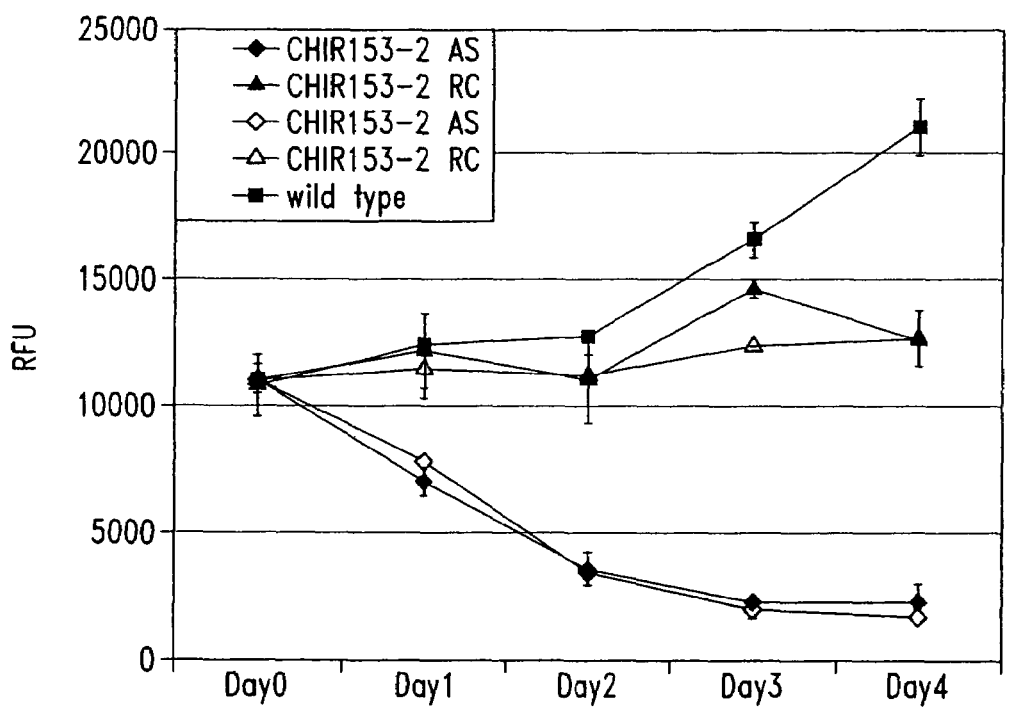

Following reverse transcription, target genes were amplified using the Roche Light Cycler™ real-time PCR machine. 20 μL aliquots of PCR amplification mixture were prepared by mixing the following components in the order listed: 2 μL 10× PCR buffer II (containing 10 mM Tris pH 8.3 and 50 mM KCl, Perkin-Elmer, Norwalk, Conn.) 3 mM MgCl$_2$, 140 μM each dNTP, 0.175 pmol of each Sos1 oligo, 1:50,000 dilution of SYBR® Green, 0.25 mg/mL BSA, 1 unit Taq polymerase, and H$_2$O to 20 μL. SYBR® Green (Molecular Probes, Eugene, Oreg.) is a dye that fluoresces when bound to double-stranded DNA, allowing the amount of PCR product produced in each reaction to be measured directly. 2 μL of completed reverse transcription reaction was added to each 20 μL aliquot of PCR amplification mixture, and amplification was carried out according to standard protocols. As shown in Table 1 below, and in FIGS. 3 and 4, antisense oligonucleotides specific for Sos1 reduced Sos1 mRNA levels in SW620 cells and in BT474 cells.

TABLE 1

| Antisense | Percent reduction in mRNA levels |
|---|---|
| SW620 akt1 (SEQ ID NO: 12) | 94.2 |
| SW620 Sos1 (SEQ ID NO: 2) | 79.8 |
| SW620 Sos1 (SEQ ID NO: 3) | 83.0 |
| SW620 Kras (SEQ ID NO: 4) | 78.9 |
| BT474 Sos1 (SEQ ID NO: 2) | 69.2 |
| BT474 kras (SEQ ID NO: 4) | 79.3 |
| BT474 Her2/neu (SEQ ID NO: 5) | 60.7 |

Example 2

Soft Agar Assay

The bottom layer consists of 2 ml of 0.6% agar in media plated fresh within a few hours of layering on the cells. For the cell layer, cells (BT474 and SW620) transfected as described in Example 1 are removed from the plate in 0.05% trypsin and washed twice in media. Cells are counted in a coulter counter, and resuspended to 10$^6$ cells per ml in media. 10 ml aliquots are placed with media in 96-well plates to check counting with WST1 (WST-1 Cell Proliferation Assay available from, for example, Panvera) or diluted further for soft agar assay. 2000 cells are plated in 800 ml 0.4% agar in duplicate wells above 0.6% agar bottom layer.

For the media layer, after the cell layer agar solidifies, 2 ml of media is bled on top and antisense or reverse control oligo is added without delivery vehicles. Fresh media and oligos are added every 3-4 days.

Colonies form in 10 days to 3 weeks. Fields of colonies are counted by eye. WST-1 metabolism values are used to compensate for small differences in starting cell number. Larger fields can be scanned for visual record of differences. Cell colonies are counted in 6 randomly-selected grids across each soft-agar well. The number of colonies is normalized by comparison with a starting WST1 value.

EXAMPLE 3

Increased Release of Lactate Dehydrogenase by Antisense-Treated Cells

BT474 cells are transformed as described in Example 1 using the antisense oligonucleotide of SEQ ID NO:2 or 3 and the reverse complement. The LDH assay is performed using a Roche LDH kit.

EXAMPLE 4

Treatment of Cells with Sos1 RNAi

Using the methods of Example 1, for antisense treatment, cells are treated with an oligonucleotide based on the Sosi sequence: AACAGAAGCTGATCGCATAGC (SEQ ID NO:15). Two complementary ribonucleotide monomers with deoxy-TT extensions at the 3' end are synthesized and annealed. Cells of the BT474 cell line are treated with 50-200 nM RNAi with 1:3 L2 lipitoid. Cells are harvested on day 1, 2, 3 and 4, and analyzed for Sosi protein by Western analysis, as is known in the art.

From the foregoing it will be appreciated that, although specific embodiments of the invention have been described herein for purposes of illustration, various modifications may be made without departing from the spirit and scope of the invention. Accordingly, the invention is not limited except as by the appended claims.

---

We claim:

1. An isolated Sos1 inhibitor of wherein said inhibitor is an antisense molecule that consists of a nucleic acid sequence selected from the group consisting of SEQ ID NOs:2 and 3.

2. A composition comprising a therapeutically effective amount of at least one Sos1 inhibitor, wherein said inhibitor is an antisense molecule that consists of a nucleic acid sequence selected from the group consisting of SEQ ID NOs:2 and 3.

* * * * *